US009090904B2

(12) United States Patent
Croughan

(10) Patent No.: US 9,090,904 B2
(45) Date of Patent: Jul. 28, 2015

(54) RESISTANCE TO ACETOHYDROXYACID SYNTHASE-INHIBITING HERBICIDES

(75) Inventor: Timothy P. Croughan, Crowley, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 1617 days.

(21) Appl. No.: 12/166,517

(22) Filed: Jul. 2, 2008

(65) Prior Publication Data

US 2009/0025108 A1    Jan. 22, 2009

Related U.S. Application Data

(63) Continuation of application No. 11/109,587, filed on Apr. 19, 2005, now Pat. No. 7,399,905, which is a continuation of application No. 10/258,842, filed as application No. PCT/US01/15072 on May 9, 2001, now Pat. No. 6,943,280.

(60) Provisional application No. 60/203,434, filed on May 10, 2000.

(51) Int. Cl.
  *C12N 15/82* (2006.01)
  *A01H 5/10* (2006.01)
  *C12N 9/88* (2006.01)

(52) U.S. Cl.
  CPC .............. *C12N 15/8278* (2013.01); *A01H 5/10* (2013.01); *C12N 9/88* (2013.01)

(58) Field of Classification Search
  None
  See application file for complete search history.

(56) References Cited

U.S. PATENT DOCUMENTS

| 4,443,971 | A | 4/1984 | Chaleff ........................... 47/58 |
| 4,761,373 | A | 8/1988 | Anderson et al. .......... 435/172.3 |
| 4,774,381 | A | 9/1988 | Chaleff et al. .................... 800/1 |
| 4,997,665 | A * | 3/1991 | Grethlein ..................... 426/542 |
| 5,013,659 | A | 5/1991 | Bedbrook et al. .......... 435/172.3 |
| 5,084,082 | A | 1/1992 | Sebastian .......................... 71/90 |
| 5,304,732 | A | 4/1994 | Anderson et al. ............. 800/235 |
| 5,331,107 | A | 7/1994 | Anderson et al. ............. 800/235 |
| 5,545,822 | A * | 8/1996 | Croughan ..................... 800/300 |
| 5,605,011 | A | 2/1997 | Bedbrook et al. ................ 47/58 |
| 5,633,437 | A | 5/1997 | Bernasconi et al. .......... 800/205 |
| RE35,661 | E | 11/1997 | Thill ............................. 800/200 |
| 5,718,079 | A | 2/1998 | Anderson et al. ................ 47/58 |
| 5,731,180 | A | 3/1998 | Dietrich ..................... 435/172.3 |
| 5,736,629 | A | 4/1998 | Croughan ..................... 800/235 |
| 5,767,361 | A | 6/1998 | Dietrich ........................ 800/205 |
| 5,767,366 | A | 6/1998 | Sathasivan et al. ........... 800/205 |
| 5,773,702 | A | 6/1998 | Penner et al. .................. 800/230 |
| 5,773,703 | A | 6/1998 | Croughan ..................... 800/235 |
| 5,773,704 | A | 6/1998 | Croughan ..................... 800/235 |
| 5,853,973 | A | 12/1998 | Kakefuda et al. .................. 435/4 |
| 5,859,348 | A | 1/1999 | Penner et al. .................. 800/230 |
| 5,928,937 | A | 7/1999 | Kakefuda et al. .......... 435/320.1 |
| 5,952,553 | A | 9/1999 | Croughan .................... 800/320.2 |
| 6,211,438 | B1 | 4/2001 | Anderson et al. ............. 800/300 |
| 6,211,439 | B1 | 4/2001 | Anderson et al. ............. 800/300 |
| 6,222,100 | B1 | 4/2001 | Anderson et al. ............. 800/300 |
| 6,274,796 | B1 | 8/2001 | Croughan .................... 800/320.2 |
| 6,943,280 | B2 * | 9/2005 | Croughan ..................... 800/300 |
| 7,019,196 | B1 | 3/2006 | Croughan ..................... 800/300 |
| 7,345,221 | B2 | 3/2008 | Croughan ..................... 800/300 |
| 7,399,905 | B2 | 7/2008 | Croughan ..................... 800/300 |
| 2004/0123343 | A1 * | 6/2004 | La Rosa et al. .............. 800/278 |
| 2006/0162016 | A1 | 7/2006 | Croughan ..................... 800/278 |

FOREIGN PATENT DOCUMENTS

| EP | 0 257 993 | 3/1988 |
| EP | 0 364 580 | 4/1990 |
| EP | 0 525 384 | 2/1993 |
| EP | 0 154 204 | 1/1994 |
| EP | 0 730 030 | 9/1996 |
| EP | 0 965 265 | 12/1999 |
| WO | WO 90/14000 | 11/1990 |
| WO | WO 92/08794 | 5/1992 |
| WO | WO 96/33270 | 10/1996 |
| WO | WO 97/41218 | 11/1997 |
| WO | WO 98/02526 | 1/1998 |

(Continued)

OTHER PUBLICATIONS

Shimizu et al, NCBI Accession No. AB049823 published Jan. 10, 2001.*
Shimizu et al, NCBI Accession No. AB049822 published Jan. 10, 2001.*
Norman et al 1997 B.R. Wells Rice Research Studies, Arkansas Agricultural Experiment Station, Fayetteville, Arkansas.*
Wright et al 1998 Weed Science 46: 13-23.*
Goulart et al 2012 Euphytica Published online Jun. 17, 2012; Identification of origin and analysis of population structure of filed-selected imidazolinone-herbicide resistant red rice (*Oryza sativa*).*
Roso et al 2010, Genbank Accession No. HM625775, NCMBI, National Library of Medicine, Bethesda Maryland USA.*
U.S. Appl. No. 12/050,448, filed Mar. 2008, Croughan.
Affidavit of Steven D. Linscombe (Nov. 8, 2004).

(Continued)

*Primary Examiner* — David H Kruse
(74) *Attorney, Agent, or Firm* — John H. Runnels

(57) ABSTRACT

Nucleotide sequences are disclosed that may be used to impart herbicide resistance to green plants. The sources of novel herbicide resistance were originally isolated in mutant rice plants. The sequences impart pre-emergence resistance, post-emergence resistance, or both pre-emergence resistance and post-emergence resistance to multiple herbicides. To date, resistance has been demonstrated against at least the following herbicides: imazethapyr, imazapic, imazapyr, imazamox, sulfometuron methyl, imazaquin, chlorimuron ethyl, metsulfuron methyl, rimsulfuron, thifensulfuron methyl, pyrithiobac sodium, tribenuron methyl, and nicosulfuron. Green plants transformed with these sequences are resistant to these herbicides and to derivatives of these herbicides, and to at least some of the other herbicides that normally inhibit acetohydroxyacid synthase (AHAS), particularly imidazolinone and sulfonylurea herbicides.

67 Claims, No Drawings

(56) References Cited

FOREIGN PATENT DOCUMENTS

| WO | WO 98/02527 | 1/1998 |
|----|----|----|
| WO | WO 00/26390 | 5/2000 |
| WO | WO 00/27182 | 5/2000 |
| WO | WO 01/65922 | 9/2001 |
| WO | WO 01/82685 | 11/2001 |

OTHER PUBLICATIONS

Bernasconi et al., J. Biological Chemistry, vol. 270, No. 29, pp. 17381-17385 (1995).
Croughan, T. et al., "Applications of Biotechnology to Rice Improvement," *Proc. 25th Rice Tech. Work. Groups*, pp. 62-63 (1994).
Croughan, T., "Application of Tissue Culture Techniques to the Development of Herbicide Resistant Rice," *Louisiana Agriculture*, vol. 37, No. 3, pp. 25-26 (1994).
Croughan, T. et al., "Imidazolidone-Resistant Rice," 90th Annual Research Report, Rice Research Station, 1998, p. 511 (Dec. 1999).
Croughan, T. et al., "Assessment of Imidazolidone-Resistant Rice," *87th Annual Research Report, Rice Research Station*, 1995, pp. 491-525 (Sep. 1996).
Croughan, T., "Herbicide Resistant Rice," *Proc. 25th Rice Tech. Work. Groups*, p. 44 (1994).
Croughan, T. et al., "Rice Biotechnology Research," 89th Annual Research Report, Rice Research Station, 1997, p. 464 (Sep. 1998).
Croughan, T. et al., "IMI-Rice Evaluations," 88th Annual Research Report, Rice Research Station, 1996, pp. 603-629 (Sep. 1997).
Croughan, T., "Improvement of Lysine Content and Herbicide Resistance in Rice Through Biotechnology," USDA CRIS Report Accession No. 0168634 (for Fiscal Year 1997—actual publication date currently unknown).
Croughan, T., "Improvement of Lysine Content and Herbicide Resistance in Rice Through Biotechnology," USDA CRIS Report Accession No. 0168634 (for Fiscal Year 1999—actual publication date currently unknown).
Croughan, T., "Improvement of Lysine Content and Herbicide Resistance in Rice Through Biotechnology," USDA CRIS Report Accession No. 0168634 (for Fiscal Year 2000—actual publication date currently unknown).
Croughan, T., "Production of Rice Resistant to AHAS-Inhibiting Herbicides," Congress on Cell and Tissue Culture, Tissue Culture Association, In Vitro, vol. 30A, p. 60, Abstract P-1009 (Jun. 4-7, 1994).
Croughan, T. et al., "Rice and Wheat Improvement through Biotechnology," *84th Annual Research Report, Rice Research Station*, 1992, pp. 100-103 (1993).
Croughan, T. et al., "Rice and Wheat Improvement through Biotechnology," *85th Annual Research Report, Rice Research Station*, 1993, pp. 116-156 (1994).
Croughan, T. et al., "Rice and Wheat Improvement through Biotechnology," USDA CRIS Report Acession No. 0150120 (for Fiscal Year 1994—actual publication date currently unknown).
Croughan, T. et al., "Rice Improvement through Biotechnology," *86th Annual Research Report, Rice Research Station*, 1994, pp. 461-482 (Sep. 1995).
Duggleby, R., "Identification of an Acetolactate Synthase Small Subunit Gene in Two Eukaryotes," Gene, vol. 190, pp. 245-249 (1997).
Hattori et al., Molecular and General Genetics, vol. 232, pp. 67-173 (1992).
Hipple, L. et al., "AHAS Characterization of Imidazolinone Resistant Rice," pp. 68-69 in Proceedings of the 27th Rice Technical Working Group Meeting (1999).
Hipple, L. et al., "AHAS Characterization of Imidazolinone Resistant Rice," pp. 45-46 in Program of the 27th Rice Technical Working Group Meeting (Mar. 1998).
Lee et al., "The Molecular Basis of Sulfonylurea Herbicide Resistance in Tobacco," The EMBO J., vol. 7, No. 5, pp. 1241-1248 (1988).
Mazur et al., "Isolation and Characterization of Plant Genes Coding for Acetolactate Synthase, the Target Enzyme for Two Classes of Herbicides," Plant Physiol., vol. 85, pp. 1110-1117 (1987).
Miki et al., "Transformation of *Brassica napus* canola cultivars with *Arabidopsis thaliana* Acetohydroxyacid Synthase Genes and Analysis of Herbicide Resistance," Theor. Appl. Genet., vol. 80, pp. 449-458 (1990).
Newhouse et al., "Mutations in corn (*Zea mays* L.) Conferring Resistance to Imidazolinone Herbicides," Theor. Appl. Genet., vol. 83, pp. 65-70 (1991).
Odell et al., "Comparison of Increased Expression of Wild-Type and Herbicide-Resistant Acetolactate Synthase Genes in Transgenic Plants, and Indication of Postranscriptional Limitation on Enzyme Activity," Plant Physiol., vol. 94, pp. 1647-1654 (1990).
Ott, K-H et al., "Rational Molecular Design and Genetic Engineering of Herbicide Resistant Crops by Structure Modeling and Site-directed Mutagenesis of Acetohydroxyacid Synthase," J.Mol. Biol., vol. 263, pp. 359-368 (1996).
Reek, G. et al., "'Homology' in Proteins and Nucleic Acids: A Terminology Muddle and a Way out of it," Cell, vol. 50, p. 667 (1987).
Rice, W. et al., "Delayed Flood for Rice Water Weevil Control using Herbicide Resistant Germplasm," p. 134 in Proceedings of the 27th Rice Technical Working Group Meeting (1999).
Rice, W. et al., "Delayed flood for management of rice water weevil (Coleopterae: Curculionidae)," Environmental Entomology, vol. 28, No. 6, pp. 1130-1135 (Dec. 1999).
Rice, W. et al., "Delayed Flood for Rice Water Weevil Control using Herbicide Resistant Germplasm," p. 61 in Program of the 27th Rice Technical Working Group Meeting (Mar. 1998).
Sathasivan et al., "Molecular Basis of Imidazolinone Herbicide Resistance in *Arabidopsis thaliana* var Columbia," Plant Physiol. vol. 97, pp. 1044-1050 (1991).
Sathasivan et al., "Nucleotide Sequence of a Mutant Acetolactate Synthase Gene from an Imidazolinone-resistant *Arabidopsis thaliana* var. Columbia," Nucleic Acids Research vol. 18, No. 8, p. 2188 (1990).
Saxena et al., "Herbicide Resistance in *Datura innoxia*," Plant Physiol., vol. 86, pp. 863-867 (1988).
Sebastian et al., "Soybean Mutants with Increased Tolerance for Sulfonylurea Herbicides," Crop. Sci., vol. 27, pp. 948-952 (1987).
Shimamoto et al., "Fertile Transgenic Rice Plants Regenerated from Transformed Protoplasts," Nature, vol. 338, pp. 274-276 (1989).
Shimizu et al., Accession No. ABO49822, NCBI, Nat'l Institute of Health (2001).
Shimizu et al., Accession No. ABO49823, NCBI, Nat'l Institute of Health (2001).
Singh, B.K. et al., "Assay of Acetohydroxyacid Synthase," *Analytical Biochemistry*, vol. 171, pp. 173-179 (1988).
Terakawa et al., "Rice Mutant Resistant to the Herbicide Bensulfuron Methyl (BSM) by in vitro Selection," Japan. J. Breed., vol. 42, pp. 267-275 (1992).
Webster, E. et al., "Weed Control Systems for Imidazolinone-Rice," p. 215 in Proceedings of the 27th Rice Technical Working Group Meeting (1999).
Webster, E. et al., "Weed Control Systems for Imi-Rice," p. 33 in Program of the 27th Rice Technical Working Group Meeting (Mar. 1998).
Wiersma et al., "Isolation, Expression and Phylogenetic Inheritance of an Acetolactate Synthase Gene from *Brassica napus*," Mol. Gen. Genet., vol. 219, pp. 413-420 (1989).
Chang, A.K. et al., "Herbicide-resistant Forms of *Arabidopsis thaliana* Acetohydroxyacid Synthase: Characterization of the Catalytic Properties and Sensitivity to Inhibitors of Four Defined Mutants," Biochem. J., vol. 333, pp. 765-777 (1998).
Chong, C-K et al., "Amino Acid Residues Conferring Herbicide Tolerance in Tobacco Acetolactate Synthase," Biochem. and Biophys. Res. Comm., vol. 279, pp. 462-467 (2000).
Lee, Y-T et al., "Effect of Mutagenesis at Serine 653 of *Arabidopsis thaliana* Acetohydroxyacid Synthase on the Sensitivity to Imidazolinone and Sulfonylurea Herbicides," FEBS Letters, vol. 452, pp. 341-345 (1999).
Shaner D. et al., "Imidazolinone-Resistant Crops: Selection, Characterization and Management," *Herbicide-Resistant Crops: Agricultural, Environmental, Economic, Regulatory, and Technical Aspects*, Lewis Publishers, pp. 144-157 (1996).

(56) References Cited

OTHER PUBLICATIONS

Zhu, Tong et al., "Engineering Herbicide-resistant Maize Using Chimeric RNA/DNA Oligonucleotides," Nature Biotech., vol. 18, pp. 555-558 (2000).
Galli, Fabrizio, "Welfare Effects of Herbicide-Tolerant Rice Adoption in Brazil," Int'l Assoc. of Agricultural Economists (IAAE) Triennial Conference, pp. 1-33 (2012).
Menezes, V.G. et al., "Arroz-vermelho (*Oryza sativa*) resistente aos herbicidas imidazolinonas," Planta Daninha, vol. 27, pp. 1047-1052 (2009) (includes machine translation by Google Translate).
Roso, A.G. et al., "Regional Scale Distribution of Imidazolinone Herbicide-Resistant Alleles in Red Rice (*Oryza sativa*. L.) Determined Through SNP Markers," Field Crops Res., vol. 119, pp. 175-182 (2010).

* cited by examiner ial application Ser. No. 11/109,
587, filed Apr. 19, 2005, now U.S. Pat. No. 7,399,905, issued
Jul. 15, 2008; which was a continuation of patent application
Ser. No. 10/258,842, 35 U.S.C. §371 date Oct. 28, 2002, now
U.S. Pat. No. 6,943,280, issued Sep. 13, 2005; which was the
United States national stage of international application PCT/
US01/15072, international filing date May 9, 2001, and published as WO 01/85970 A2 on Nov. 15, 2001; which claimed
the benefit of the May 10, 2000 filing date of U.S. provisional
application Ser. No. 60/203,434 under 35 U.S.C. §119(e); the
complete disclosures of all of which are hereby incorporated
by reference.

TECHNICAL FIELD

This invention pertains to herbicide resistant plants, and to
nucleotide sequences conferring herbicide resistance to
plants, particularly resistance to herbicides that normally
interfere with the plant enzyme acetohydroxyacid synthase
(AHAS), such herbicides including for example those of the
imidazolinone class and those of the sulfonylurea class.

BACKGROUND ART

The development of novel herbicide resistance in plants
offers significant production and economic advantages. As
one example, rice production is frequently restricted by the
prevalence of a weedy relative of rice that flourishes in commercial rice fields. The weed is commonly called "red rice,"
and belongs to the same species as cultivated rice (*Oryza
sativa* L.). The genetic similarity of red rice and commercial
rice has made herbicidal control of red rice difficult. The
herbicides Ordram™ (molinate: S-ethyl hexahydro-1-H-
azepine-1-carbothioate) and Bolero™ (thiobencarb: S-[(4-
chlorophenyl)methyl]diethylcarbamothioate) offer partial
suppression of red rice, but no herbicide that actually controls
red rice is currently used in commercial rice fields because of
the simultaneous sensitivity of existing commercial cultivars
of rice to such herbicides. The release of mutant commercial
rice lines having resistance to herbicides that are effective on
red rice will greatly increase growers' ability to control red
rice infestations. The development of herbicide resistance in
other crops and other plants will have similar benefits.

Rice producers in the southern United States typically
rotate rice crops with soybeans to help control red rice infestations. While this rotation is not usually desirable economically, it is frequently necessary because no herbicide is currently available to control red rice infestations selectively in
commercial rice crops. During the soybean rotation, the producer has a broad range of available herbicides that may be
used on red rice, so that rice may again be grown the following
year. United States rice producers can lose $200-$300 per
acre per year growing soybeans instead of rice, a potential
loss affecting about 2.5 million acres annually. Additional
losses in the United States estimated at $50 million per year
result from the lower price paid by mills for grain shipments
contaminated with red rice. Total economic losses due to red
rice in the southern United States alone are estimated to be
$500 to $750 million a year. Economic losses due to red rice
may be even greater in other rice-producing countries.

Rice producers typically use the herbicides propanil (trade
name Stam™) or molinate (trade name Ordram™) to control
weeds in rice production. Propanil has no residual activity.
Molinate is toxic to fish. Neither of these herbicides controls
red rice. Imazethapyr ((±)-2-[4,5-dihydro-4-methyl-4-(1-
methylethyl)-5-oxo-1H-imidazol-2-yl]-5-ethyl-3-pyridinecarboxylic acid) offers an environmentally acceptable alternative to molinate, has the residual weed control activity that
propanil lacks, and is a very effective herbicide on red rice.
Imazethapyr also offers excellent control of other weeds
important in rice production, including barnyardgrass. Barnyardgrass is a major weed in rice production, and is currently
controlled with propanil or molinate. However, barnyardgrass has developed resistance to propanil in some
regions.

The total potential market for rice varieties that are resistant to a herbicide that can control red rice is about 5.3 million
acres in the United States, and the potential market outside the
United States is much larger. World rice production occupies
about 400 million acres. Red rice and other weeds are major
pests in rice production in the United States, Brazil, Australia,
Spain, Italy, North Korea, South Korea, Philippines, Vietnam,
China, Taiwan, Brazil, Argentina, Colombia, India, Pakistan,
Bangladesh, Japan, Ecuador, Mexico, Cuba, Malaysia, Thailand, Indonesia, Sri Lanka, Venezuela, Myanmar, Nigeria,
Uruguay, Peru, Panama, Dominican Republic, Guatemala,
Nicaragua, and other rice-producing areas.

A number of herbicides target acetohydroxyacid synthase
(AHAS), an enzyme also known as acetolactate synthase
(ALS), and also designated as E.C. 4.1.3.18. This enzyme
catalyzes the first step in the synthesis of the amino acids
leucine, valine, and isoleucine. Inhibition of the AHAS
enzyme is normally fatal to plants. Herbicides that inhibit the
enzyme acetohydroxyacid synthase would offer a number of
advantages over currently available herbicides if they could
be used in commercial rice production, and the production of
other crops, in circumstances where they could not otherwise
be used. Potential advantages include long residual activity
against weeds, effective control of the more important weeds
in rice production, including red rice, and relative environmental acceptability. Even in regions where red rice is not
currently a problem, the availability of herbicide-resistant
rice can have a major influence on rice production practices
by providing the farmer with a new arsenal of herbicides
suitable for use in rice fields.

Total potential demand for resistance to AHAS-acting herbicides in plants other than rice is difficult to estimate, but
could be very large indeed.

U.S. Pat. No. 4,761,373 describes the development of
mutant herbicide-resistant maize plants through exposing tissue cultures to herbicide. The mutant maize plants were said
to have an altered enzyme, namely acetohydroxyacid synthase, that conferred resistance to certain imidazolinone and
sulfonamide herbicides. See also U.S. Pat. Nos. 5,304,732,
5,331,107, 5,718,079, 6,211,438, 6,211,439, and 6,222,100;
and European Patent Application 0 154 204 A2.

Lee et al., "The Molecular Basis of Sulfonylurea Herbicide
Resistance in Tobacco," *The EMBO J.*, vol. 7, no. 5, pp.
1241-1248 (1988), describe the isolation and characterization
from *Nicotiana tabacum* of mutant genes specifying herbicide resistant forms of acetolactate synthase, and the reintroduction of those genes into sensitive lines of tobacco.

Saxena et al., "Herbicide Resistance in *Datura innoxia*,"
*Plant Physiol.*, vol. 86, pp. 863-867 (1988) describe several
*Datura innoxia* lines resistant to sulfonylurea herbicides,
some of which were also found to be cross-resistant to imidazolinone herbicides.

Mazur et al., "Isolation and Characterization of Plant
Genes Coding for Acetolactate Synthase, the Target Enzyme
for Two Classes of Herbicides," *Plant Physiol.* vol. 85, pp.

1110-1117 (1987), discuss investigations into the degree of homology among acetolactate synthases from different species.

U.S. Pat. No. 5,767,366 discloses transformed plants with genetically engineered imidazolinone resistance, conferred through a gene cloned from a plant such as a mutated *Arabidopsis thaliana*. See also a related paper, Sathasivan et al., "Nucleotide Sequence of a Mutant Acetolactate Synthase Gene from an Imidazolinone-resistant *Arabidopsis thaliana* var. *Columbia*," *Nucleic Acids Research* vol. 18, no. 8, p. 2188 (1990).

Examples of resistance to AHAS-inhibiting herbicides in plants other than rice are disclosed in U.S. Pat. No. 5,013,659; K. Newhouse et al., "Mutations in corn (*Zea mays* L.) Conferring Resistance to Imidazolinone Herbicides," *Theor. Appl. Genet.*, vol. 83, pp. 65-70 (1991); K. Sathasivan et al., "Molecular Basis of Imidazolinone Herbicide Resistance in *Arabidopsis thaliana* var *Columbia*," *Plant Physiol* vol. 97, pp. 1044-1050 (1991); B. Miki et al., "Transformation of *Brassica napus* canola cultivars with *Arabidopsis thaliana* Acetohydroxyacid Synthase Genes and Analysis of Herbicide Resistance," *Theor. Appl. Genet., vol.* 80, pp. 449-458 (1990); P. Wiersma et al., "Isolation, Expression and Phylogenetic Inheritance of an Acetolactate Synthase Gene from *Brassica napus*," *Mol. Gen. Genet.*, vol. 219, pp. 413-420 (1989); J. Odell et al., "Comparison of Increased Expression of Wild-Type and Herbicide-Resistant Acetolactate Synthase Genes in Transgenic Plants, and Indication of Postranscriptional Limitation on Enzyme Activity," *Plant Physiol.*, vol. 94, pp. 1647-1654 (1990); published international patent application WO 92/08794; U.S. Pat. No. 5,859,348; published international patent application WO 98/02527; published European Patent Application EP 0 965 265 A2, and published international patent application WO 90/14000.

U.S. Pat. Nos. 5,853,973 and 5,928,937 disclose the structure-based modeling of AHAS, the presumptive binding pockets on the enzyme for AHAS-acting herbicides, and certain designed AHAS mutations to confer herbicide residence. These patents also disclose amino acid sequences for the AHAS enzymes and isozymes from several plants, including that from *Zea mays*. See also published international patent application WO 96/33270.

S. Sebastian et al., "Soybean Mutants with Increased Tolerance for Sulfonylurea Herbicides," *Crop. Sci.*, vol. 27, pp. 948-952 (1987) discloses soybean mutants resistant to sulfonylurea herbicides. See also U.S. Pat. No. 5,084,082.

K. Shimamoto et al., "Fertile Transgenic Rice Plants Regenerated from Transformed Protoplasts," *Nature*, vol. 338, pp. 274-276 (1989) discloses a genetic transformation protocol in which electroporation of protoplasts was used to transform a gene encoding β-glucuronidase into rice.

T. Terakawa et al., "Rice Mutant Resistant to the Herbicide Bensulfuron Methyl (BSM) by in vitro Selection," *Japan. J. Breed.*, vol. 42, pp. 267-275 (1992) discloses a rice mutant resistant to a sulfonylurea herbicide, derived by selective pressure on callus tissue culture. Resistance was attributed to a mutant AHAS enzyme.

Following are publications by the inventor (or the inventor and other authors) concerning research on herbicide-resistant rice varieties. These publications are T. Croughan et al., "Rice and Wheat Improvement through Biotechnology," 84*th Annual Research Report, Rice Research Station*, 1992, pp. 100-103 (1993); T. Croughan et al., "Rice and Wheat Improvement through Biotechnology," 85*th Annual Research Report, Rice Research Station*, 1993, pp. 116-156 (1994); T. Croughan, "Application of Tissue Culture Techniques to the Development of Herbicide Resistant Rice," *Louisiana Agriculture*, vol. 37, no. 3, pp. 25-26 (1994); T. Croughan et al., "Rice Improvement through Biotechnology," 86*th Annual Research Report, Rice Research Station*, 1994, pp. 461-482 (1995); T. Croughan et al., "Assessment of Imidazolinone-Resistant Rice," 87*th Annual Research Report, Rice Research Station*, 1994, pp. 491-525 (September 1996); T. Croughan et al., "IMI-Rice Evaluations," 88*th Annual Research Report, Rice Research Station*, 1996, pp. 603-629 (September 1997); T. Croughan et al., "Rice Biotechnology Research," 89*th Annual Research Report, Rice Research Station*, 1997, p. 464 (September 1998); T. Croughan et al., "Imidazolinone-Resistant Rice," 90*th Annual Research Report, Rice Research Station*, 1998, p. 511 (December 1999); T. Croughan et al., "Rice and Wheat Improvement through Biotechnology," USDA CRIS Report Accession No. 0150120 (for Fiscal Year 1994-actual publication date currently unknown); T. Croughan, "Improvement of Lysine Content and Herbicide Resistance in Rice through Biotechnology," USDA CRIS Report Accession No. 0168634 (for Fiscal Year 1997-actual publication date currently unknown); T. Croughan, "Improvement of Lysine Content and Herbicide Resistance in Rice through Biotechnology," USDA CRIS Report Accession No. 0168634 (for Fiscal Year 1999-actual publication date currently unknown); T. Croughan, "Improvement of Lysine Content and Herbicide Resistance in Rice through Biotechnology," USDA CRIS Report Accession No. 0168634 (for Fiscal Year 2000-actual publication date currently unknown); T. Croughan, "Herbicide Resistant Rice," *Proc. 25th Rice Tech. Work. Groups*, p. 44 (1994); T. Croughan et al, "Applications of Biotechnology to Rice Improvement," *Proc. 25th Rice Tech. Work. Groups*, pp. 62-63 (1994); T. Croughan, "Production of Rice Resistant to AHAS-Inhibiting Herbicides," Congress on Cell and Tissue Culture, Tissue Culture Association, *In Vitro*, vol. 30A, p. 60, Abstract P-1009 (Jun. 4-7, 1994). (Note that the Annual Research Reports of the Rice Research Station are published in the year after the calendar year for which activities are reported. For example, the 84*th Annual Research Report, Rice Research Station*, 1992, summarizing research conducted in 1992, was published in 1993.) The reports in the 87*th* and 88*th Annual Research Report, Rice Research Station* (published September 1996 and September 1997, respectively) mention the breeding line 93AS3510 in tables giving data on certain herbicide resistance trials. These reports gave no information on how the breeding line was developed. The breeding line was not publicly available at the times these reports were published. The breeding line 93AS3510 is the same as the ATCC 97523 rice that is described in greater detail in the present inventor's later-published international patent application WO 97/41218 (1997) and U.S. Pat. Nos. 5,736,629, 5,773,704, 5,952,553, and 6,274,796.

See also E. Webster et al., "Weed Control Systems for Imi-Rice," p. 33 in *Program of the 27th Rice Technical Working Group Meeting* (March 1998); L. Hipple et al., "AHAS Characterization of Imidazolinone Resistant Rice," pp. 45-46 in *Program of the 27th Rice Technical Working Group Meeting* (March 1998); W. Rice et al., "Delayed Flood for Rice Water Weevil Control using Herbicide Resistant Germplasm," p. 61 in *Program of the 27th Rice Technical Working Group Meeting* (March 1998); E. Webster et al., "Weed Control Systems for Imidazolinone-Rice," p. 215 in *Proceedings of the 27th Rice Technical Working Group Meeting* (1999); L. Hipple et al., "AHAS Characterization of Imidazolinone Resistant Rice," pp. 68-69 in *Proceedings of the 27th Rice Technical Working Group Meeting* (1999); W. Rice et al., "Delayed Flood for Rice Water Weevil Control using Herbicide Resistant Germplasm," p. 134 in *Proceedings of the 27th Rice Technical Working Group Meeting* (1999); and W. Rice et al., "Delayed flood for management of rice water weevil (Coleopterae: Curculionidae)," *Environmental Entomology*, vol. 28, no. 6, pp. 1130-1135 (December 1999).

The present inventor's U.S. Pat. No. 5,545,822 discloses a line of rice plants having a metabolically-based resistance to herbicides that interfere with the plant enzyme acetohydroxyacid synthase; i.e., the herbicide resistance of these rice plants was not due to a resistant AHAS enzyme. (See published international patent application WO 97/41218, pages 6-9.) See also the present inventor's U.S. Pat. No. 5,773,703.

The present inventor's published international patent application WO 97/41218 discloses one line of rice plants having a mutant AHAS enzyme that is resistant to herbicides that interfere with the wild-type plant enzyme acetohydroxyacid synthase. This line of rice plants was developed by exposing rice seeds to the mutagen methanesulfonic acid ethyl ester (EMS), and screening millions of progeny for herbicide resistance. See also the present inventor's U.S. Pat. Nos. 5,736,629, 5,773,704, 5,952,553, and 6,274,796.

The present inventor's published international patent application WO 00/27182 discloses additional lines of rice plants having mutant AHAS enzymes that are resistant to herbicides that interfere with the wild-type plant enzyme acetohydroxyacid synthase. These lines of rice plants were developed by exposing rice seeds to EMS, and screening millions of progeny for herbicide resistance.

U.S. Pat. No. 4,443,971 discloses a method for preparing herbicide tolerant plants by tissue culture in the presence of herbicide. U.S. Pat. No. 4,774,381 discloses sulfonylurea (sulfonamide) herbicide-resistant tobacco plants prepared in such a manner.

U.S. Pat. No. 5,773,702 discloses sugar beets with a resistant mutant AHAS enzyme, derived from cell cultures grown in the presence of herbicide. See also published international patent application WO 98/02526.

Published international patent application WO 00/26390 discloses the cloning and sequencing of the *Arabidopsis* AHAS small subunit protein, and an expression vector to transform plants with that small AHAS subunit to impart herbicide tolerance.

U.S. Pat. No. 5,633,437 discloses a herbicide resistant AHAS enzyme and gene isolated from cockleburs.

U.S. Pat. No. 5,767,361 discloses a mutant, resistant AHAS enzyme from maize. The definitions of the U.S. Pat. No. 5,767,361 are incorporated into the present disclosure by reference, to the extent that those definitions are not inconsistent with the present disclosure, as are that patent's descriptions of certain genetic transformation techniques for plants. See also U.S. Pat. No. 5,731,180 and European Patent Application 0 525 384 A2.

U.S. Pat. No. 5,605,011; European Patent Application 0 257 993 A2; and European Patent Application 0 730 030 A1 disclose resistant acetolactate synthase enzymes derived from callus culture of tobacco cells in the presence of herbicide, from spontaneous mutations of the ALS gene in yeast; EMS-induced mutations in *Arabidopsis* seeds; certain modifications of those enzymes; and the transformation of various plants with genes encoding the resistant enzymes. These patents disclose several techniques for modifying AHAS genes to produce herbicide-resistant AHAS enzymes, and for transforming plants with those genes.

U.S. Pat. Re No. 35,661 (a reissue of U.S. Pat. No. 5,198, 599) discloses lettuce plants with enhanced resistance to herbicides that target the enzyme acetolactate synthase. The initial source of herbicide resistance was a prickly lettuce weed infestation in a grower's field, an infestation that was not controlled with commercial sulfonylurea herbicides.

T. Shimizu et al., "*Oryza sativa* ALS mRNA for acetolactate synthase, complete cds, herbicide sensitive wild type," BLAST accession number AB049822 (April 2001), available through www.ncbi.nlm.nih.gov/blast, discloses the nucleotide sequence and inferred amino acid sequence for wild type ALS cDNA from *Oryza sativa* var. *Kinmaze*. These two sequences are reproduced below as SEQ ID NOS 2 and 3, respectively.

T. Shimizu et al., "*Oryza sativa* ALS mRNA for acetolactate synthase, complete cds, herbicide resistant biotype," BLAST accession number AB049823 (April 2001), available through www.ncbi.nlm.nih.gov/blast, discloses the nucleotide sequence and inferred amino acid sequence for an ALS cDNA from *Oryza sativa* var. *Kinmaze* that was reported to be herbicide resistant, although the nature of the herbicide resistance is not specified in the BLAST description. These two sequences are reproduced below as SEQ ID NOS 4 and 5, respectively.

Following are selected data taken from some of the references cited above, concerning the locations of certain imidazolinone or sulfonylurea herbicide tolerance mutations in AHAS/ALS from various species. No attempt has been made to reconcile or align the different nucleotide or amino acid numbering systems used in the different references. In describing the substitutions below (as well as in the remainder of the specification and the claims), the wild-type nucleotide or amino acid is always listed first, followed by the mutant nucleotide or amino acid. All substitutions discussed refer to the AHAS/ALS DNA coding sequence, or to the expressed or inferred AHAS/ALS amino acid sequence.

Lee et al. (1988) reported that there were two homologous ALS genes in *Nicotiana tabacum*. The sulfonylurea herbicide-resistant C3 mutant in one ALS gene had a Pro-Gln replacement at amino acid 196; while the sulfonylurea herbicide-resistant S4-Hra mutant in the other ALS gene had two amino acid changes: Pro-Ala at amino acid 196, and Trp-Leu at amino acid 573.

Sathasivan et al. (1990), Sathasivan et al. (1991), and U.S. Pat. No. 5,767,366 reported a G-A nucleotide substitution at position 1958, corresponding to a Ser-Asn substitution at position 653, in an imidazolinone herbicide-resistant *Arabidopsis thaliana*.

Wiersma et al. (1989) reported sulfonylurea herbicide resistance in tobacco plants that had been transformed with a mutant *Brassica napus* ALS gene, in which codon 173 had been altered by site-directed mutagenesis to replace Pro with Ser.

European patent application 0 257 993 A2 reported several spontaneous mutations in the yeast (*Saccharomyces cerevisiae*) ALS gene that resulted in sulfonylurea herbicide resistance: at amino acid position 121, a substitution of wild-type Gly by Ser; at amino acid position 122, a substitution of wild-type Ala by Pro, Asp, Val, or Thr; at position 197, a substitution of wild-type Pro by Ser or Arg; at position 205, a substitution of wild-type Ala by Asp or Thr; at position 256, a substitution of wild-type Lys by Glu, Thr, or Asn; at position 359, a substitution of wild-type Met by Val; at position 384, a substitution of wild-type Asp by Glu, Val, or Asn; at position 588, a substitution of wild-type Val by Ala; at position 591, a substitution of wild-type Trp by Arg, Cys, Gly, Leu, Ser, or Ala; at position 595, a substitution of wild-type Phe by Leu. The same patent application reported several site-directed mutations of the yeast ALS gene at some of the same positions to also produce sulfonylurea herbicide resistance: at amino acid position 122, a substitution of wild-type Ala by Ser, Val, Thr, Pro, Asn, Ile, His, Arg, Leu, Tyr, Cys, Phe, Glu, Met, Lys, Gln, or Trp; at position 205, a substitution of wild-type Ala by Arg, Cys, Glu, or Trp; at position 256, a substitution of wild-type Lys by Asp, Gly, Leu, Pro, or Trp; at position 359, a substitution of wild-type Met by Pro or Glu; at position 384, a substitution of wild-type Asp by Pro, Trp, Ser, Gly, Cys, or Lys; at position 591, a substitution of wild-type Trp by Asp, Glu, Phe, His, Tyr, Ile, Val, Lys, Arg, Met, Asn, Gln, or Thr. See also U.S. Pat. No. 5,605,011, which also describes experimental data for the following site-directed mutations: at amino acid 121, a substitution of wild-type Gly by Asn or Ala; at amino acid 197, a substitution of wild-type Pro by Gln, Glu, Ala, Gly, Trp, Tyr, Cys, or Val; at amino acid 205, a substitution of wild-type Ala by Tyr, Val, or Asn; at amino acid 359, a substitution of wild-type Met by Gln, Lys, Tyr, or Cys; at position 583, a substitution of wild-type Val by Ser, Asn, Trp, or Cys; and at position 595, a substitution of wild-type Phe by Gly, Asn, Arg, Cys, Pro, Ser, or Trp. Other amino substitutions at the same positions are also described prophetically, without experimental data. See also U.S. Pat. No. 5,013,659.

WO 98/02527 reported sulfonylurea and triazolopyrimidine resistance in one line of sugar beets resulting from a C-T substitution at nucleotide 562, corresponding to a Pro-Ser substitution at amino acid 188. This same reference also reported sulfonylurea, imidazolinone, and triazolopyrimidine resistance in a second line of sugar beets resulting from two mutations: The same mutation as reported in the first line (from which the second line had been derived), coupled with a G-A substitution at nucleotide 337, corresponding to an Ala-Thr substitution at amino acid 113. See also WO 98/02526, U.S. Pat. Nos. 5,859,348 and 5,773,702.

WO 96/33270 describes a number of designed or predicted mutations from a structure-based modeling method, that were said to induce imidazolinone tolerance in AHAS Experimental results confirming such tolerance in mutated *Arabidopsis* AHAS, either in vitro or in transformed tobacco plants in vivo were provided for the following substitutions: Met-Ile at amino acid position 124, Met-His at position 124, Arg-Glu at position 199, and Arg-Ala at position 199. See also U.S. Pat. Nos. 5,928,937 and 5,853,973.

WO 92/08794 reported imidazolinone resistance in two lines of maize. One had a G-A substitution at nucleotide position 171, resulting in an Ala-Thr substitution at the corresponding amino acid position. The other had a G-A substitution at position 1888, resulting in a Ser-Asn substitution at the corresponding amino acid position.

U.S. Pat. No. 5,731,180 reported imidazolinone resistance in maize resulting from a G-A substitution at nucleotide position 1898, resulting in a Ser-Asn substitution at amino acid position 621. See also U.S. Pat. No. 5,767,361 and European patent application 0 525 384.

U.S. Pat. No. 5,633,437 reported imidazolinone resistance in cockleburs, characterized by five differences between resistant ALS enzyme biotypes and sensitive biotypes: Lys-Glu at amino acid position 63, Phe-Leu at position 258, Gln-His at position 269, Asn-Ser at position 522, and Trp-Leu at position 552. The changes at positions 522 and 552 were thought to be particularly important.

T. Shimizu et al., "*Oryza sativa* ALS mRNA for acetolactate synthase, complete cds, herbicide resistant biotype," BLAST accession number AB049823 (April 2001) reported a nucleotide sequence and inferred amino acid sequence for a rice ALS that was said to be herbicide resistant, although the nature of the herbicide resistance was not specified in the BLAST entry. As compared to a contemporaneous wild type ALS for the same rice variety (Kinmaze), the inferred amino acid sequence for the resistant ALS appeared to display two differences: a Trp-Leu substitution at position 548, and a Ser-Ile substitution at position 627.

DISCLOSURE OF INVENTION

I have discovered nucleotide sequences that may be used to impart herbicide resistance to green plants. These sources of novel herbicide resistance were originally isolated in mutant rice plants. The nucleotide sequences impart pre-emergence resistance, post-emergence resistance, or both pre-emergence resistance and post-emergence resistance to multiple herbicides. To date, resistance has been demonstrated against at least the following herbicides, as well as some mixtures of the same herbicides: imazethapyr, imazapic, imazapyr, imazamox, sulfometuron methyl, imazaquin, chlorimuron ethyl, metsulfuron methyl, rimsulfuron, thifensulfuron methyl, pyrithiobac sodium, tribenuron methyl, and nicosulfuron. Green plants transformed with these nucleotide sequences are also resistant to derivatives of these herbicides, and to at least some of the other herbicides that normally inhibit acetohydroxyacid synthase (AHAS), particularly imidazolinone and sulfonylurea herbicides. The degree of herbicide resistance imparted by some of the novel nucleotide sequences is comparable to (and is possibly greater than) the highest levels of resistance to AHAS-inhibiting herbicides that have previously been found in resistant mutants of any species of green plant that is normally susceptible to this class of herbicides.

These nucleotide sequences may be used to transform green plants including, but not limited to, rice. Alternatively, analogous mutations may be introduced into green plants by site-directed mutagenesis of the plant's native AHAS coding sequence(s). As a particular example, transformation of the nucleotide sequences into rice plants, or site-directed mutagenesis of rice plants, will accelerate what could also be accomplished, perhaps more slowly, by traditional breeding techniques such as crossing and back-crossing. Since no coding sequence from another species is thereby introduced into the rice, most researchers would not consider such a transformed rice plant to be "transgenic." (Not even a marker gene is needed for such a transformation, since selection may be performed directly for the herbicide resistance trait itself.) Similarly, where site-directed mutagenesis is used to introduce an analogous point mutation into the native AHAS coding sequence of a green plant other than rice, most researchers would not consider the resulting plant to be transgenic.

Besides controlling red rice, many AHAS-inhibiting herbicides also effectively control other weeds commonly found in fields in which rice and other crops are grown. Several of these herbicides have residual activity, so that one treatment controls both existing weeds and weeds that sprout later—a significant advantage in production.

No herbicide currently labelled for use on rice has residual activity against a broad spectrum of weeds including red rice. With effective residual activity against red rice and other weeds, rice producers now have a weed control system far superior to those currently used. One role of water in rice production is in weed control—a layer of standing water in the rice field inhibits the growth of weeds. With a herbicide having residual weed control properties, producers will have much greater flexibility in water management. Flooding of fields may now be delayed, which in turn will help control the rice water weevil, a primary insect pest of rice. Alternatively, or perhaps in conjunction, pumping costs could be reduced by delaying flooding until sufficient rain falls to flood a field at no cost to the producer.

The herbicide resistance of each of the novel nucleotide sequences is attributable to mutation of the expressed rice AHAS enzyme, producing enzymes that express direct resistance to levels of herbicide that normally inhibit the wild-type AHAS enzymes. That the resistance is due to mutant AHAS enzymes (rather than another route such as gene copy number, enhanced promoter activity, metabolic degradation, etc.) has been confirmed by in vitro assays.

The following mutations have been observed in one or more of the AHAS coding sequences from the various herbicide-resistant rice lines: (1) Some of the herbicide-resistant lines have a serine-to-asparagine mutation in the codon corresponding to amino acid location 627. (2) One of the herbicide-resistant lines is believed to have a serine-to-lysine mutation in the codon corresponding to amino acid location 627, coupled with a deletion causing a frame shift, leading to a stop codon soon thereafter.

Some of the mutant rice AHAS amino acid sequences reported here show a serine-to-asparagine mutation at amino acid 627, a location near the carboxy terminus of the AHAS protein that is analogous to the location of serine-to-asparagine mutations that have been previously reported in imidazolinone herbicide-resistant AHAS from *Arabidopsis* and maize plants (see discussion above). However, the novel sequences show surprising properties that could not have been predicted from the earlier work. The degree of herbicide resistance imparted by some of the novel nucleotide sequences is comparable to (and is possibly greater than) the highest levels of resistance to AHAS-inhibiting herbicides that have previously been found in resistant mutants of any species of green plant that is normally susceptible to this class of herbicides. The underlying reason is currently unknown. Without wishing to be bound by this theory, it is possible that the rice AHAS molecule provides a particularly favorable setting for the Ser-Asn mutation. In other words, it is hypothesized that, as compared to other plants in which a Ser-Asn AHAS mutation has previously been reported, there exists a synergy between other portions of the rice AHAS molecule and the site of the mutation, leading to some very high levels of herbicide resistance. These very high levels of herbicide resistance make the novel mutant rice AHAS sequences more attractive as candidates for transforming other plants for herbicide resistance.

From the data reported here, as well as data reported in some of the references previously cited, it appears that mutations at locations homologous to the 627 serine in the rice AHAS molecule can lead to resistance to AHAS-inhibiting herbicides in green plants. Without wishing to be bound by this theory, it is hypothesized that a Ser-Asn amino substitution at this location is particularly favorable for a herbicide resistant phenotype. We also report results here for line CMC31 showing instead a Ser-Lys substitution at this location, followed by a frame-shift mutation; and we note that the Shimizu (April 2001) BLAST submissions reported herbicide resistance (of currently unknown nature) following a Ser-Ile substitution at position 627 and a Trp-Leu substitution at position 548.

Due to their chemical similarity to Asn, their steric similarity to Asn, or both, it is also expected that the following amino acid substitutions at locations homologous to the 627 serine in the rice AHAS molecule will also lead to resistance to AHAS-inhibiting herbicides: Gln, Asp, and Glu. These mutations could not, however, result from single-nucleotide substitutions in the coding sequence, and would therefore be considerably less likely to result from undirected mutation breeding efforts. However, these mutations could be induced by site-directed mutagenesis techniques known in the art. See, e.g., R. Higuchi, "Recombinant PCR," pp. 177-183 in M. Innis et al. (Eds.), PCR Protocols: A Guide to Methods and Applications, Academic Press (1990); U.S. Pat. No. 6,010,907; Kunkel, *Proc. Natl. Acad. Sci. USA*, vol. 82, pp. 488-492 (1985); Kunkel et al., *Methods Enzymol.*, vol. 154, pp. 367-382 (1987); U.S. Pat. No. 4,873,192; Walker et al. (Eds.), *Techniques in Molecular Biology* (MacMillan, New York, 1983); or the Genoplasty™ protocols of ValiGen (Newtown, Pa.).

For that matter, any of the mutations described here may be incorporated into the genome of rice or of any other green plant using site-directed mutagenesis. Doing so can, among other things, speed the process of introducing herbicide resistance into an existing cultivar, by eliminating the time needed for crossing and back-crossing through traditional breeding techniques, and without introducing a gene from another species.

Likewise, the Ser-Lys substitution at position 627, followed by a frame shift could instead be a Ser-Arg or Ser-His substitution, followed by a frame shift, since Lys, Arg, and His are chemically similar.

Thus one aspect of this invention provides green plants transformed with an oligonucleotide sequence encoding the rice AHAS molecule, in which the serine at amino acid position 627 has been replaced with asparagine.

Another aspect of this invention provides green plants having an oligonucleotide sequence encoding an AHAS molecule in which the serine homologous to that of position 627 in the rice AHAS molecule has been replaced with glutamine, glutamic acid, or aspartic acid. The AHAS molecule may otherwise be native to the same plant in which it is being expressed, or it may be derived from another plant. One embodiment of this aspect of the invention is a green plant comprising an oligonucleotide sequence encoding an AHAS molecule identical to the wild-type rice AHAS molecule, except that the serine of position 627 in the rice AHAS molecule has been replaced with glutamine, glutamic acid, or aspartic acid. If the mutant AHAS molecule is otherwise native to the plant in which it is expressed, except for the substitution at position 627, then such a plant should not be considered a "genetically modified organism," in the popular sense of an organism that has been artificially transformed with an oligonucleotide coding sequence derived from a different species. For example, such a plant could be a rice plant containing an oligonucleotide sequence encoding an AHAS molecule identical to the wild-type rice AHAS molecule, except that the serine of position 627 in the rice AHAS molecule has been replaced with glutamine, glutamic acid, or aspartic acid.

Another aspect of this invention provides green plants having an oligonucleotide sequence encoding an AHAS molecule in which the serine homologous to that of position 627 in the rice AHAS molecule has been replaced with lysine, arginine, or histidine—preferably lysine—followed by whatever amino acids may be encoded between position 627 and the carboxy terminus as the result of a frame shift in the AHAS coding sequence at or following position 627. The AHAS molecule may otherwise be native to the same plant in which it is being expressed, or it may be derived from another plant. One embodiment of this aspect of the invention is a green plant comprising an oligonucleotide sequence encoding an AHAS molecule identical to the wild-type rice AHAS molecule, except that the serine of position 627 in the rice AHAS molecule has been replaced with lysine, arginine, or histidine—preferably lysine—followed by whatever amino acids may be encoded between position 627 and the carboxy terminus as the result of a frame shift in the AHAS coding sequence at or following position 627. If the mutant AHAS molecule is otherwise native to the plant in which it is expressed, except for the substitutions at position 627 and subsequent, then such a plant should not be considered a "genetically modified organism," in the popular sense of an organism that has been artificially transformed with an oligonucleotide coding sequence derived from a different species. For example, such a plant could be a rice plant containing an oligonucleotide sequence encoding an AHAS molecule identical to the wild-type rice AHAS molecule, except that the serine of position 627 in the rice AHAS molecule has been replaced with lysine, arginine, or histidine—preferably lysine—followed by whatever amino acids may be encoded between position 627 and the carboxy terminus as the result of a frame shift in the AHAS coding sequence at or following position 627.

The procedures used below to assay the activity of the acetohydroxyacid synthases were substantially as described in B. K. Singh et al., "Assay of Acetohydroxyacid Synthase," *Analytical Biochemistry*, vol. 171, pp. 173-179 (1988), except as noted. In the first paragraph of Singh's "Materials and Methods," instead of corn suspension culture cells, shoot tissues from greenhouse-grown rice seedlings at the 3-4 leaf stage of development, or rice suspension culture cells were used. For shoot tissues, 40.0 grams (fresh weight) of tissue were extracted in the same manner for each of the breeding lines; for Cypress suspension cells, 16.0 grams of cells were used, harvested eight days after subculture. At the suggestion of the first author, B. K. Singh (personal communication), the desalting step mentioned at the bottom of Singh's first column under "Materials and Methods" was eliminated. Pursuit™ herbicide (imazethapyr) or Arsenal™ herbicide (imazapyr) was included in the "standard reaction mixture" for the AHAS assay in various concentrations. Colorimetric absorbance was measured at 520 nm. Checks were made of direct acetoin formation during the enzyme assay.

An alternative AHAS assay that could be used (but that was not used in collecting the data reported here) is that disclosed in U.S. Pat. No. 5,605,011, at col. 53, line 61 through col. 54, line 37.

MODES FOR CARRYING OUT THE INVENTION

A total of 27 new rice lines expressing resistance to AHAS-inhibiting herbicides were identified, following exposure of rice seeds to the mutagen methanesulfonic acid ethyl ester (EMS). Additional resistant rice lines will be developed and identified using similar mutation and screening techniques. Other mutagens known in the art may be substituted for EMS in generating such mutations, for example, sodium azide, N-methyl-N-nitrosourea, N-ethyl-N-nitrosourea, nitrosoquanidine, hydroxylamine, hydrazine, ionizing radiation (such as X-rays, gamma rays, or UV), or radiomimetic compounds such as bleomycins, etoposide, and teniposide. (Bleomycins, for example, are glycopeptide antibiotics isolated from strains of *Streptomyces verticillus*. One bleomycin is sold under the trademark Blenoxane® by Bristol Laboratories, Syracuse, N.Y.) The resistant AHAS nucleotide sequences from these rice lines will be cloned and used to transform other rice lines, and lines of other green plants, to impart herbicide resistance characteristics.

Examples 1-15

Approximately 52 million mutated ($M_2$) rice seed were screened. The mutated seed were developed by soaking a total of 340 pounds of seed ($M_1$), of the rice cultivars "Cypress" or "Bengal," in a 0.175% (by weight) aqueous solution of EMS. Approximately 170 lb. of rice were exposed to EMS for 16 hours; approximately 85 lb. were exposed for 24 hours; and approximately 85 lb were exposed for 35 hours. Seed from the three exposure regimens were pooled for the screening experiments described below.

Following EMS treatment, the $M_1$ seed were thoroughly rinsed with water and drained before being planted by broadcast-seeding into shallow water, water that was drained 24 hours later. The field was re-flooded three days later, and the field was maintained in a flooded condition until it was drained for harvesting. The harvested $M_2$ seed were stored over the winter, and plants grown from the $M_2$ seed were screened for herbicide resistance the following spring. Following drill-seeding of approximately 52 million $M_2$ seed, a pre-emergence application of imazethapyr at a rate of 0.125 lb ai/A (pounds of active ingredient per acre) was applied prior to the first flush. A post-emergence treatment of imazethapyr at 0.063 lb ai/A was applied when the rice reached the 3-leaf stage. The fifteen $M_2$ plants that survived the herbicide application were collected and transferred to the greenhouse.

The herbicide resistance of the progeny of these plants ($M_3$) was confirmed through a post-emergence application of 0.125 lb ai/A imazethapyr at the 3-leaf stage in the greenhouse. The 15 resistant plants of 52 million total $M_2$ plants represent a success rate of approximately 1 imidazolinone-resistant mutant identified per 3.5 million mutated seeds screened.

$M_4$ progeny seed were collected from the resistant $M_3$ plants, and were used in a field test. The field test comprised 8 replicate sets. Each of the sets contained 100 rows, each row four feet in length. Each of the sets had 74 rows of the $M_4$ resistant lines. Each set had multiple rows of each of the 15 resistant lines, with the number of rows of each of the lines varying due to the different numbers of seeds of each that were available at the time. Each of the replicate sets also contained 16 rows of the non-resistant cultivar "Cypress" as a negative control, and 10 rows of earlier-developed herbicide-resistant rice lines as positive controls. (The positive controls were either ATCC 97523 or a hybrid of ATCC 97523 and ATCC 75295.) A different herbicide treatment was applied post-emergence to each of these eight replicate sets when the rice reached the 3-leaf stage. The control set was treated with 4 quarts/acre of Arrosolo™. Arrosolo™ is a herbicide that is currently used commercially with conventional rice varieties. The remaining 7 sets were treated with imidazolinone herbicides as follows: (1) imazethapyr (trade name Pursuit™ or Newpath™) at 0.125 lb ai/A; (2) imazethapyr at 0.188 lb ai/A; (3) imazapic (trade name Cadre™) at 0.063 lb ai/A; (4) imazapic at 0.125 lb ai/A; (5) imazapyr (trade name Arsenal™) at 0.05 lb ai/A; (6) imazapyr at 0.09 lb ai/A; and (7) a mixture of 75% imazethapyr and 25% imazapyr (trade name Lightning™) at 0.052 lb ai/A.

Note that all herbicide application rates tested were equal to or greater than the recommended application rates for the use of the same herbicides on other crops.

Levels of resistance to herbicide were determined both at three weeks after spraying, and at maturity. No row was significantly injured by the control treatment with the conventional rice herbicide Arrosolo™. By contrast, each of the seven imidazolinone treatments resulted in 100% control of the rows of non-resistant Cypress rice, without a single surviving plant among any of the 112 treated rows. Each of the herbicide-resistant $M_4$ progeny rows in each of the sets, and each of the herbicide-resistant positive controls in each of the sets, displayed insignificant injury or no injury from the various imidazolinone treatments. The rows of resistant $M_4$ progeny treated with the imidazolinones, and the rows of herbicide-resistant positive controls treated with the imidazolinones, were visually indistinguishable from the Arrosolo™-treated rows with respect to height, vigor, days to maturity, and lack of visible herbicide injury.

Samples of the seed harvested from each of the fifteen lines of the $M_4$ progeny, i.e., samples of $M_5$ seed from each of the fifteen separate lines; lines designated by the inventor as SSC01, SSC02, SSC03, SSC04, SSC05, SSC06, SSC07, SSC08, SSC09, SSC10, SSC11, SSC12, SSC13, SSC14, and SSC15; were separately deposited with the American Type Culture Collection (ATCC), 10801 University Boulevard, Manassas, Va. 20110-2209 on 5 Nov. 1998; and were assigned ATCC Accession Nos. 203419, 203420, 203421, 203422, 203423, 203424, 203425, 203426, 203427, 203428, 203429, 203430, 203431, 203432, and 203433, respectively. Each of these deposits was made pursuant to a contract between ATCC and the assignee of this patent application, Board of Supervisors of Louisiana State University and Agricultural and Mechanical College. Each of the contracts with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for the availability of these seeds to one determined by the U.S. Commissioner of Patents and Trademarks (or by any counterpart to the Commissioner in any patent office in any other country) to be entitled thereto under pertinent statutes and regulations. The assignee of the present application has agreed that if any of the seeds on deposit should become nonviable or be lost or destroyed when cultivated under suitable conditions, they will be promptly replaced on notification with a viable sample of the same seeds.

Examples 16-27

Approximately 60 million additional mutated ($M_2$) rice seed were screened. The mutated seed were developed by soaking a total of 300 pounds of seed ($M_1$) of the rice cultivar "Cypress" in a 0.175% (by weight) aqueous solution of the mutagen EMS for 23 hours.

Following EMS treatment the $M_1$ seed were thoroughly rinsed with water and drained before being planted by broadcast-seeding into shallow water, water that was drained 24 hours later. The field was re-flooded three days later, and the field was maintained in a flooded condition until it was drained for harvesting. The harvested $M_2$ seed were stored over the winter, and plants grown from the $M_2$ seed were screened for herbicide resistance the following spring. Following broadcast-seeding and shallow soil incorporation of approximately 60 million $M_2$ seed, a post-emergence application of imazapic (trade name Cadre™) at 0.125 lb ai/A was sprayed on half the field, and a post-emergence application of imazapyr (trade name Arsenal™) at 0.10 lb ai/A was applied to the remaining half of the field at the three-leaf stage. The twenty-three $M_2$ plants that survived the herbicide application were collected and transferred to the greenhouse. Later testing (described below) showed that twelve of these plants represented new herbicide resistant lines; the other plants were "volunteer" seed of the ATCC 97523 line that had remained in the soil from a prior season.

The 12 resistant plants of 60 million total $M_2$ plants represent a success rate of approximately 1 imidazolinone-resistant mutant identified per 5 million mutated seeds screened.

The herbicide resistance of the progeny of these plants ($M_3$) was confirmed with the following herbicide applications in the greenhouse: 0.125 lb ai/A imazethapyr (trade name Pursuit™) as a pre-emergence application; 0.063 lb ai/A imazethapyr as a post-emergence application; 0.10 lb ai/A sulfometuron methyl (trade name Oust™) as a pre-emergence application; 0.05 lb ai/A sulfometuron methyl as a post-emergence application; 0.10 lb ai/A nicosulfuron (trade name Accent™) applied pre-emergence; and 0.05 lb ai/A nicosulfuron applied post-emergence. Two $M_3$ seed from each of the twenty-three herbicide-resistant lines were planted in each of four replicate pots for each treatment. Equivalent plantings of control lines were made with (non-resistant) Cypress and Bengal rice seeds.

Samples of the seed harvested from several of these lines of the $M_4$ progeny; namely, samples of $M_5$ seed from each of the seven separate lines designated by the inventor as PWC16, PWC23, CMC29, CMC31, WDC33, WDC37, and WDC38; were separately deposited with the American Type Culture Collection (ATCC), 10801 University Boulevard, Manassas, Va. 20110-2209 on 2 Nov. 1999; and were assigned ATCC Accession Nos. PTA-904, PTA-905, PTA-902, PTA-903, PTA-906, PTA-907, and PTA-908, respectively. Each of these deposits was made pursuant to a contract between ATCC and the assignee of this patent application, Board of Supervisors of Louisiana State University and Agricultural and Mechanical College. Each of the contracts with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for the availability of these seeds to one determined by the U.S. Commissioner of Patents and Trademarks (or by any counterpart to the Commissioner in any patent office in any other country) to be entitled thereto under pertinent statutes and regulations. The assignee of the present application has agreed that if any of the seeds on deposit should become nonviable or be lost or destroyed when cultivated under suitable conditions, they will be promptly replaced on notification with a viable sample of the same seeds.

Five other lines, designated by the inventor as PWC17, PWC19, PWC21, PWC22, and CMC27, exhibited lower levels of herbicide resistance. These lines appear to differ both from the lines that have now been deposited with ATCC, and from prior line ATCC 97523. Due to their lower levels of resistance, these lines had not been deposited with ATCC as of the 10 May 2000 priority date of the present application. However, these lines may have potential value as breeding material to cross with other sources of herbicide resistance, or with each other, in order to enhance total levels of resistance. If these five lines involve different resistance mechanisms, or different AHAS isozymes as compared to the ATCC-deposited lines, then crossing one of these lines with one of the ATCC-deposited lines could result in a hybrid with an enhanced total level of resistance. Their herbicide resistance levels would not, however, appear to make any of these five lines, standing alone, suitable candidates for breeding new herbicide resistant rice lines.

Example 28

Mutations were induced in seeds of ten rice varieties by exposure either to gamma rays or to EMS. Ten-pound lots of seed of each variety were subjected to 25 k-rad of gamma irradiation from a Cobalt-60 source at the Nuclear Science Center, Louisiana State University, Baton Rouge, La. prior to planting. An additional ten pounds of seed of each variety was divided into three equal portions; and each portion was soaked for 16 hours in either 0.1%, 0.5%, or 1% EMS immediately prior to planting. Several hundred pounds of seed were harvested from plants grown from the seeds subjected to these mutagenic treatments.

The following spring the harvested seed was planted in strips in a field planting occupying a total of about three acres. At the 3-4 leaf stage of seedling development, herbicides were applied to screen for herbicide-resistant mutants. Half of the seedlings of each variety were sprayed with a 2× treatment of nicosulfuron, and half were sprayed with a 2× treatment of imazethapyr, in both cases by a tractor-mounted sprayer. Nicosulfuron was applied at the rate of 0.063 lb active ingredient (a.i.) per acre, and imazethapyr was applied at 0.125 lb a.i. per acre. Non-ionic surfactant (0.25%) was added to each spray solution. Approximately 35 million rice seedlings were sprayed in this manner. About four weeks later a single surviving plant was identified. The surviving plant was in a strip that had been sprayed with imazethapyr, and was derived from the "parent" rice variety "AS3510," treated by exposure to 0.5% EMS. No symptoms of injury from the herbicide treatment were evident on this plant at the time it was discovered, while all the other plants were either severely injured or dead. The plant was transferred to the greenhouse for seed increase and further testing.

Subsequent testing in the greenhouse and field demonstrated that the progeny of this rice plant possessed resistance to several AHAS-inhibiting herbicides, including at least the following herbicides: imazethapyr, nicosulfuron, imazaquin, imazameth, imazapyr, and imazamox. AHAS enzyme assays indicated that this rice line possessed a mutant AHAS enzyme that was responsible for resistance to AHAS-inhibiting herbicides.

A sample of the seed from this rice line, designated 93AS3510 or SPCW-1, was deposited with the American Type Culture Collection (ATCC), current address 10801 University Boulevard, Manassas, Va. 20110-2209 on 25 Apr. 1996, and was assigned ATCC Accession No. 97523. This deposit was made pursuant to a contract between ATCC and the assignee of this patent application, Board of Supervisors of Louisiana State University and Agricultural and Mechanical College. The contract with ATCC provides that these seeds or the progeny of these seeds are now available permanently and without restriction to the public. The assignee of the present application has agreed that if any of the seeds on deposit should become nonviable or be lost or destroyed when cultivated under suitable conditions, they will be promptly replaced on notification with a viable sample of the same seeds.

Further Field Tests and Greenhouse Tests

Further field tests and greenhouse tests were conducted to evaluate the tolerance of the resistant lines. The field tests included both pre-emergence and post-emergence herbicide application studies. The same lines were included in both studies, except that line WDC37 was included in the pre-emergence study only, due to the lack of sufficient quantity of seed at the time of the study.

The herbicides applied as pre-emergence applications were imazaquin, imazethapyr, and imazapic. Each treatment was applied to each of two replicate plots. Each replicate plot contained three-foot long rows of each herbicide resistant line, along with a check row of non-resistant rice. Two plots were left unsprayed to serve as untreated controls. All herbicide-resistant lines exhibited little or no injury from the herbicide applications. All check rows of the non-resistant rice variety Cypress, by contrast, were either killed or severely injured in all plots given herbicide treatments.

Post-emergence application was studied in fifty replicate plots of the same herbicide-resistant lines, except that line WDC37 was not included in the post-emergence field study. For the post-emergence field study, each herbicide treatment was applied to each of two replicate plots. Four plots were left unsprayed to serve as untreated controls. Herbicide treatments studied post-emergence were imazethapyr (Pursuit™ or Newpath™), imazapic (Cadre™), imazamox (Raptor™), a 1:1 (by weight) mixture of imazapic and imazapyr, a 3:1 (by weight) mixture of imazapic (Cadre™) and imazapyr (Arsenal™), imazapyr (Arsenal™), chlorimuron ethyl (Classic™), metsulfuron methyl (Ally™), nicosulfuron (Accent™), rimsulfuron (Matrix™), a 2:1 mixture (by weight) (Harmony Extra™) of thifensulfuron methyl and tribenuron methyl, and pyrithiobac sodium (Staple™).

The greenhouse tests comprised two replicate studies using the same herbicides and rates as were used in the post-emergence field test. The greenhouse studies evaluated the post-emergence herbicide resistance of a few lines for which the quantity of seed then available was inadequate to include in the field tests. Seeds of the resistant lines were planted in 2 inch×2 inch peat pots, and the seedlings were then sprayed at the 3-4 leaf stage. Non-resistant check lines were included for comparison. As in the field tests, the non-resistant checks were either killed or severely injured by the herbicide treatments.

The results of these field and greenhouse studies are summarized in Tables 3 and 4.

Results and Discussion

Previous selections for imidazolinone-resistant rice by screening following seed exposure to EMS had resulted in fewer resistant rice lines. For example, screening approximately 35 million $M_2$ seed following exposure of the $M_1$ seed to 0.1%, 0.5%, or 1.0% EMS for 16 hours resulted in a single herbicide-resistant mutant plant (ATCC 97523), for a success ratio of 1 resistant mutant per 35 million mutated seed. By contrast, each of the two later series of screenings had a significantly higher rate of successfully producing herbicide-resistant mutants. It is believed, without wishing to be bound by this theory, that the improved efficiency was due to the difference in mutagen concentrations and exposure times used.

The more efficient mutation protocols described here used a relatively longer exposure to a relatively lower concentration of mutagen than had previously been used. In Examples 1-15 the average mutagen exposure time was 22.75 hours, and the EMS concentration was 0.175%. This represents a 42% longer average exposure time, and a 65% reduction in the mutagen concentration, as compared to the only successful event from the earlier screening of 35 million seeds (Example 28). The result was a ten-fold increase in the rate of resistant mutant recovery (one per 3.5 million seed versus one per 35 million seed).

Examples 16-27 used conditions similar to those for Examples 1-15, and were also more efficient in producing resistant mutants. The same EMS mutagen concentration (0.175%) was used, and only a slightly different exposure time (23 hours versus an average of 22.75 hours). The herbicide-resistant mutant production rate in this trial was 1 plant per 5 million seed. These results indicate that longer exposures to lower mutagen concentrations appear generally to produce higher rates of successful herbicide resistant mutants.

Each of the resistant mutants from these two screenings exhibited resistance to one or more imidazolinone and sulfonylurea herbicides. A summary of the herbicide applications used in the initial screening for resistance is given in Table 1. The results of the field tests for Examples 1-15 (SSC01 through SSC15) are given in Table 2. The results of the field tests for Examples 16-27 (those resistant lines having PWC, CMC, or WDC designations) are given in Tables 3 and 4. Note that the application rates in Tables 1, 2, and 3 are given in pounds of active ingredient per acre, while the rates in Table 4 are given in ounces of active ingredient per acre.

TABLE 1

Screening Herbicide Application

| Line | Imazethapyr 0.125 pre-emerge + 0.063 post-emerge (lb ai/A) | Imazapyr 0.10 post-emerge (lb ai/A) | Imazameth 0.125 post-emerge (lb ai/A) |
|---|---|---|---|
| SSC01 | X | | |
| SSC02 | X | | |
| SSC03 | X | | |
| SSC04 | X | | |
| SSC05 | X | | |
| SSC06 | X | | |
| SSC07 | X | | |
| SSC08 | X | | |
| SSC09 | X | | |
| SSC10 | X | | |
| SSC11 | X | | |
| SSC12 | X | | |
| SSC13 | X | | |
| SSC14 | X | | |
| SSC15 | X | | |
| PWC16 | | X | |
| PWC17 | | X | |
| PWC18 | | X | |
| PWC19 | | X | |
| PWC20 | | X | |
| PWC21 | | X | |
| PWC22 | | X | |
| PWC23 | | X | |
| PWC24 | | X | |
| CMC25 | | | X |
| CMC26 | | | X |
| CMC27 | | | X |
| CMC28 | | | X |
| CMC29 | | | X |
| CMC30 | | | X |
| CMC31 | | | X |
| WDC32 | | | X |
| WDC33 | | | X |
| WDC34 | | | X |
| WDC35 | | | X |
| WDC36 | | | X |
| WDC37 | | | X |
| WDC38 | | | X |

TABLE 2

Post-Screening Herbicide Testing

Herbicide Application Rate (lb ai/A); & whether applied pre-emergence or post-emergence

| Line | Imazethapyr 0.125 pre | Imazethapyr 0.063 post | Imazethapyr 0.125 post | Imazethapyr 0.188 post | Imazapyr 0.05 post | Imazapyr 0.09 post | Imazameth 0.063 post | Imazameth 0.125 post | Imazethapyr (75%) + Imazapyr (25%) 0.052 post | Sulfometuron Methyl 0.10 pre | Sulfometuron Methyl 0.05 post | Nicosulfuron 0.10 pre | Nicosulfuron 0.05 post |
|---|---|---|---|---|---|---|---|---|---|---|---|---|---|
| SSC01 | X | X | X | X | X | X | X | X | X | 0 | 0 | X | X |
| SSC02 | X | X | X | X | X | X | X | X | X | 0 | 0 | X | X |
| SSC03 | X | X | X | X | X | X | X | X | X | 0 | 0 | X | X |
| SSC04 | X | X | X | X | X | X | X | X | X | X | 0 | X | X |
| SSC05 | X | X | X | X | X | X | X | X | X | 0 | 0 | X | X |
| SSC06 | X | X | X | X | X | X | X | X | X | X | 0 | X | X |
| SSC07 | X | X | X | X | X | X | X | X | X | 0 | 0 | X | X |
| SSC08 | X | X | X | X | X | X | X | X | X | X | 0 | X | X |
| SSC09 | X | X | X | X | X | X | X | X | X | 0 | 0 | X | X |
| SSC10 | X | X | X | X | X | X | X | X | X | X | 0 | X | X |
| SSC11 | X | X | X | X | X | X | X | X | X | 0 | 0 | X | X |
| SSC12 | X | X | X | X | X | X | X | X | X | 0 | 0 | X | X |
| SSC13 | X | X | X | X | X | X | X | X | X | 0 | 0 | X | X |
| SSC14 | X | X | X | X | X | X | X | X | X | 0 | 0 | X | X |
| SSC15 | X | X | X | X | X | X | X | X | X | 0 | 0 | X | X |
| PWC16 | X | X | | | | | | | | 0 | 0 | X | X |
| PWC17 | X | X | | | | | | | | X | 0 | X | X |
| PWC18 | X | X | | | | | | | | 0 | 0 | X | X |
| PWC19 | X | X | | | | | | | | 0 | 0 | X | X |
| PWC20 | X | X | | | | | | | | 0 | 0 | X | X |
| PWC21 | X | X | | | | | | | | 0 | 0 | X | X |
| PWC22 | | X | | | | | | | | | | | |
| PWC23 | X | X | | | | | | | | X | X | X | X |
| PWC24 | X | X | | | | | | | | X | 0 | X | X |
| CMC25 | X | X | | | | | | | | X | 0 | X | X |
| CMC26 | X | X | | | | | | | | 0 | 0 | X | X |
| CMC27 | | | | | | | | | | | | | |

TABLE 2-continued

Post-Screening Herbicide Testing

Herbicide Application Rate (lb ai/A); & whether applied pre-emergence or post-emergence

| Line | Imazethapyr 0.125 pre | Imazethapyr 0.063 post | Imazethapyr 0.125 post | Imazethapyr 0.188 post | Imazapyr 0.05 post | Imazapyr 0.09 post | Imazameth 0.063 post | Imazameth 0.125 post | Imazethapyr (75%) + Imazapyr (25%) 0.052 post | Sulfometuron Methyl 0.10 pre | Sulfometuron Methyl 0.05 post | Nicosulfuron 0.10 pre | Nicosulfuron 0.05 post |
|---|---|---|---|---|---|---|---|---|---|---|---|---|---|
| CMC28 | X | X | | | | | | | | 0 | 0 | X | X |
| CMC29 | X | X | | | | | | | | 0 | 0 | X | X |
| CMC30 | X | X | | | | | | | | 0 | 0 | X | X |
| CMC31 | X | X | | | | | | | | 0 | 0 | X | X |
| WDC32 | X | X | | | | | | | | X | X | X | X |
| WDC33 | X | X | | | | | | | | 0 | 0 | X | X |
| WDC34 | X | X | | | | | | | | X | 0 | X | X |
| WDC35 | X | X | | | | | | | | 0 | 0 | X | X |
| WDC36 | X | X | | | | | | | | 0 | 0 | X | X |
| WDC37 | X | X | | | | | | | | 0 | 0 | X | X |
| WDC38 | X | X | | | | | | | | 0 | 0 | X | X |

Notes to Table 2:
X = resistant;
0 = sensitive (exhibited wild-type reaction to herbicide);
blank = not yet tested.

TABLE 3

Post-Screening Herbicide Testing

Herbicide Application Rate (lb ai/A); & whether applied pre-emergence or post-emergence

| Line | Imazethapyr 0.063 pre | Imazethapyr 0.125 pre | Imazethapyr 0.188 pre | Imazethapyr 0.063 post | Imazethapyr 0.125 post | Imazapic 0.037 pre | Imazapic 0.075 pre | Imazapic 0.15 pre | Imazapic 0.075 post | Imazapic 0.15 post | Imazaquin 0.125 pre | Imazaquin 0.25 pre | Imazaquin 0.375 pre | Imazamox 0.05 post | Imazamox 0.10 post | Imazapic 0.05 + Imazapyr 0.05 post |
|---|---|---|---|---|---|---|---|---|---|---|---|---|---|---|---|---|
| SSC01 | X | X | X | X | X | X | X | X | X | X | X | X | X | X | X | X |
| SSC02 | X | X | X | X | X | X | X | X | X | X | X | X | X | X | X | X |
| SSC03 | X | X | X | X | X | X | X | X | X | X | X | X | X | X | X | X |
| SSC04 | X | X | X | X | X | X | X | X | X | X | X | X | X | X | X | X |
| SSC05 | X | X | X | X | X | X | X | X | X | X | X | X | X | X | X | X |
| SSC06 | X | X | X | X | X | X | X | X | X | X | X | X | X | X | X | X |
| SSC07 | X | X | X | X | X | X | X | X | X | X | X | X | X | X | 0 | X |
| SSC08 | X | X | X | X | X | X | X | X | X | X | X | X | X | X | X | X |
| SSC09 | X | X | X | X | X | X | X | X | X | X | X | X | X | X | X | X |
| SSC10 | X | X | X | X | X | X | X | X | X | X | X | X | X | X | X | X |
| SSC11 | X | X | X | X | X | X | X | X | X | X | X | X | X | X | X | X |
| SSC12 | X | X | X | X | X | X | X | X | X | X | X | X | X | X | X | X |
| SSC13 | X | X | X | X | X | X | X | X | X | X | X | X | X | X | 0 | X |
| SSC14 | X | X | X | X | X | X | X | X | X | X | X | X | X | X | 0 | X |
| SSC15 | X | X | X | X | X | X | X | X | X | X | X | X | X | X | 0 | X |
| PWC16 | X | X | X | X | X | X | X | X | X | X | X | X | X | X | X | X |
| PWC23 | X | X | X | X | X | X | X | X | X | X | X | X | X | X | X | X |
| CMC29 | X | X | X | X | X | X | X | X | X | X | X | X | X | X | X | X |
| CMC31 | X | X | X | X | X | X | X | X | X | X | X | X | X | X | X | X |
| WDC33 | | | | X | X | | | | X | X | | | | X | X | X |
| WDC37 | X | X | X | | | X | X | X | | | X | X | X | | | |
| WDC38 | X | X | X | X | X | X | X | X | X | X | | | | X | X | X |

| Line | Imazapic 0.075 + Imazapyr 0.025 post | Imazapic 0.15 + Imazapyr 0.05 post | Imazapyr 0.05 post | Imazapyr 0.10 post |
|---|---|---|---|---|
| SSC01 | X | X | X | X |
| SSC02 | X | X | X | X |
| SSC03 | X | X | X | X |
| SSC04 | X | X | X | X |
| SSC05 | X | X | X | X |
| SSC06 | X | X | X | X |
| SSC07 | X | X | X | X |
| SSC08 | X | X | X | X |

TABLE 3-continued

Post-Screening Herbicide Testing

| | | | | |
|---|---|---|---|---|
| SSC09 | X | X | X | X |
| SSC10 | X | X | X | X |
| SSC11 | X | X | X | X |
| SSC12 | X | X | X | X |
| SSC13 | X | X | X | X |
| SSC14 | X | X | X | X |
| SSC15 | X | X | X | X |
| PWC16 | X | X | X | X |
| PWC23 | X | X | X | X |
| CMC29 | X | X | X | X |
| CMC31 | X | X | X | X |
| WDC33 | X | X | X | X |
| WDC37 | | | | |
| WDC38 | X | X | X | X |

Notes to Table 3:
X = resistant;
0 = sensitive (exhibited wild-type reaction to herbicide);
blank = not yet tested.

TABLE 4

Post-Screening Herbicide Testing

Herbicide Application Rate (ounces ai/A); & whether applied pre-emergence or post-emergence

| | Chlorimuron Ethyl | | Metsulfuron Methyl | | Nicosulfuron | | Rimsulfuron | | Thifensulfuron methyl (66.7%) + tribenuron methyl (33.3%) | | Pyrithiobac sodium | |
|---|---|---|---|---|---|---|---|---|---|---|---|---|
| Line | 0.125 post | 0.250 post | 0.06 post | 0.12 post | 0.5 post | 1.0 post | 0.20 post | 0.40 post | 0.45 post | 0.90 post | 1.0 post | 2.0 post |
| SSC01 | X | X | X | X | X | X | X | X | X | X | X | X |
| SSC02 | X | X | X | X | X | X | X | X | X | X | X | X |
| SSC03 | X | X | X | X | X | X | X | X | X | X | X | X |
| SSC04 | X | X | X | X | X | X | X | X | X | X | X | X |
| SSC05 | X | X | X | X | X | X | X | X | X | X | X | X |
| SSC06 | X | X | X | X | X | X | X | X | X | X | X | X |
| SSC07 | X | X | X | X | X | X | X | X | X | X | X | X |
| SSC08 | X | X | X | X | X | X | X | X | X | X | X | X |
| SSC09 | X | X | X | X | X | X | X | X | X | X | X | X |
| SSC10 | X | X | X | X | X | X | X | X | X | X | X | X |
| SSC11 | X | X | X | X | X | X | X | X | X | X | X | X |
| SSC12 | X | X | X | X | X | X | X | X | X | X | X | X |
| SSC13 | X | X | X | X | X | X | X | X | X | X | X | X |
| SSC14 | X | X | X | X | X | X | X | X | X | X | X | X |
| SSC15 | X | X | X | X | X | X | X | X | X | X | X | X |
| PWC16 | 0 | 0 | X | X | X | 0 | 0 | 0 | X | X | X | X |
| PWC23 | 0 | 0 | X | X | X | 0 | 0 | 0 | X | X | X | X |
| CMC29 | 0 | 0 | 0 | X | X | 0 | 0 | 0 | X | X | X | X |
| CMC31 | 0 | 0 | 0 | X | X | X | 0 | 0 | X | X | X | X |
| WDC33 | X | X | X | X | 0 | 0 | 0 | 0 | X | X | X | X |
| WDC37 | | | | | | | | | | | | |
| WDC38 | 0 | 0 | 0 | X | X | X | 0 | 0 | 0 | X | X | X |

Notes to Table 4:
X = resistant;
0 = sensitive (exhibited wild-type reaction to herbicide);
blank = not yet tested.
In the entries for CMC29, CMC31, and WDC38 for metsulfuron methyl, and also for WDC38 (only) for the thifensulfuron methyl-tribenuron methyl mixture, at the lower rate of application, the response was identical to that of the wild-type, with all surviving the lower rate of application; while at the higher rate of application, the wild-type plants were seriously injured, and the CMC29, CMC31, and WDC38 lines exhibited substantially less injury.

Further examination of these plants led to the conclusion that the following herbicide resistant lines appeared to be identical to prior herbicide resistant line ATCC 97523, presumably because a few seeds of ATCC 97523 from prior trials had remained dormant in the soil between growing seasons: PWC18, PWC20, PWC24, CMC25, CMC26, CMC28, CMC30, WDC32, WDC34, WDC35, and WDC36.

Germination studies have confirmed the high levels of pre-emergence resistance displayed by several of the novel rice lines. Typically, when germination of a non-resistant line occurs in concentrations of imidazolinone in solution as low as 1-2 ppm, significant injury or death occurs. For the novel lines PWC16, PWC23, CMC29, CMC31, WDC33, WDC37, and WDC38, as well as for the parental (non-resistant) Cypress line, germination studies were conducted as follows. For each line, 15 seeds per dish in three replicate Petri dishes were germinated at concentrations of 0, 10, 20, 30, 40, 50, and 60 ppm for each herbicide tested. The parental Cypress line failed to germinate at concentrations of 10 ppm and higher for each of the herbicides tested. By contrast, each of the experimental lines germinated, to varying degrees (some better than others) at herbicide concentrations of 60 ppm, except as noted. With imazapyr, all experimental lines germinated to some extent at 60 ppm. With imazethapyr, all experimental lines germinated to some extent at 60 ppm. With imazamox, all experimental lines germinated to some extent at 60 ppm, except WDC38. With imazapic, only PWC16 and PWC23 germinated at 60 ppm. Thus the novel lines germinated in concentrations of herbicide 60 times that which ordinarily kills or causes significant injury to wild-type rice plants.

Enhanced resistance will result from crossing the novel rice lines with one another. Enhanced resistance will also result from the synergy of crossing one or more of the novel rice lines, with their resistant AHAS enzymes, with the metabolic-based resistant rice lines disclosed in U.S. Pat. No. 5,545,822, as typified by the rice having ATCC accession number 75295. As disclosed in the present inventor's published international patent application WO 97/41218, such synergy has been seen in hybrids of the rice having ATCC accession number 75295 with the rice having ATCC accession number 97523, the latter having a mutant, resistant AHAS enzyme in rice.

Notes on Mutation Selection Procedures in the Field

The following procedures were used for screening large quantities of mutated rice seed for herbicide resistance in the field.

Exposure to mutagen or to conditions conducive to the induction of mutations may be performed at different stages of growth and different culture conditions, e.g., exposing to mutagen dry seed, seed sprouted in water for 24 hours, or seed sprouted in water for 48 hours, etc.; or growing cells in tissue culture, such as another culture, with or without the contemporaneous application of mutagen; and the like.

Rice to be planted for seed is ordinarily cleaned after harvest. Once cleaning is completed, any standard planting equipment can be satisfactorily used. However, this laborious and time-consuming cleaning step can be bypassed if the planting equipment will tolerate the pieces of straw and other extraneous material that typically accompany combine-harvested rice. Eliminating the cleaning step allows generations of seed to be grown, screened, and increased more rapidly. For example, using a spinner/spreader attachment on a tractor allows broadcast planting of rice that is accompanied by a moderate amount of extraneous material. Broadcast planting is also more rapid than drill-seeding, saving further time and labor. Seed planted with a spinner/spreader can either be lightly incorporated into the soil following broadcast-spreading, or allowed to remain on the soil surface, in which case it must be kept sufficiently moist by irrigation if rainfall is inadequate.

Freshly-harvested rice seed may have a degree of dormancy, which prevents some of the otherwise viable seed from sprouting immediately. This dormancy normally disappears during storage. However, if the harvested seed is to be planted for selection purposes shortly after harvest to accelerate generation time, then treatment to reduce or eliminate dormancy is beneficial. One method to eliminate dormancy is to expose the seed to a temperature of about 50° C. for about five days; but temperatures significantly higher may injure the rice seeds. Moisture should be allowed to escape from the seed during this treatment, so relatively small containers of moisture-permeable material should be used, such as cloth bags. Alternatively, stems with panicles still attached may be positioned to allow air to circulate over the panicles, for example, by standing them upright in a paper bag. As a further alternative, forced-air drying may be used, with or without storage in bags, provided that the seed is situated so that moisture is not entrapped around portions of the grain.

When spraying mutated rice seed or plants to identify resistant individuals, it is important to achieve as uniform and precise a treatment as possible. Since the number of true resistant individuals will be a very small fraction of the total number of seeds, even a small fraction of "escapes" (i.e., false positives, plants fortuitously not receiving any herbicide) can complicate and retard the screening process. Therefore the herbicide-spraying equipment should be in good condition, and should be calibrated as accurately as possible. Each spray nozzle along the spraying boom should deliver spray at the same volumetric rate. Nozzles should be accurately aligned to avoid insufficient spray overlap between nozzles. Relatively short tractor spray booms (for example, approximately 12 feet) are helpful in minimizing undesirable boom movements while spraying.

Appropriate nozzles include the following, each of which has a flat spray tip, and sprays approximately 15 gallons per acre at 40 pounds per square inch (gauge) spray pressure, with a 20-inch nozzle spacing, at the indicated ground speeds: 8001VS (2 mph), 80015VS (3 mph), 8002VS (4 mph), 8003VS (5 mph). (Spraying Systems Co., Wheaton, Ill.) To optimize the spray pattern, the nozzle height above the target (either the top of the plant canopy or the soil) should be adjusted so that the spray pattern from each nozzle overlaps the spray pattern from each adjacent spray nozzle by about 30% (as measured linearly). Using the 80 degree nozzles listed above, at a 40 psi spraying pressure, and a 20 inch spacing between nozzles, an optimum spray height above the target would be 17 to 19 inches. Holding other parameters constant, but changing the nozzle spacing to 30 inches, an optimum spray height would increase to 26 to 28 inches. Using spray pressures lower than 40 psi will typically reduce the nozzle spray angles, and adjusting to a lower spray height may be necessary to achieve proper overlap at lower pressures. All spray equipment should be precisely calibrated before use.

When spraying, carefully measured marking flags to guide the spray-rig operator are frequently beneficial, as are flags at midfield in larger fields, in addition to those at the ends of the fields. Wind speed should be essentially zero, a condition that is often seen in the early morning or late afternoon. Spraying should not be performed if rain is anticipated within about the next six hours (a time that varies, depending on the particular herbicide). Pre-emergence spraying should be applied to dry ground. If the herbicide requires moisture for activation, then irrigation or rainfall after planting is required.

Uniformity of spraying is best accomplished by dividing the herbicide to be applied equally between two consecutive sprayings, one after the other. The spray solution is prepared at half the final treatment concentration. Two passes are then made in opposite directions to achieve the desired total treatment concentration. For example, if the first pass on a particular row is made in the North-to-South direction, the second pass is made in the South-to-North direction. When spraying with a tractor, this may be accomplished by traveling in the opposite direction in the same tracks for the second application.

Complete coverage is promoted by using large spray volumes (i.e., dilute concentrations of herbicide) and small spray droplet size. Spray volumes of 30 to 40 gallons per acre have worked well, particularly with two applications of 15 to 20 gallons per acre each. Spray pressures of 30 to 40 pounds per square inch (gauge) have worked well in producing fine sprays that provide thorough coverage. Nozzles should be evenly spaced, preferably about 20 inches apart.

The total rate of herbicide application used for the selection is preferably at least twice the normal use rate for the same herbicide. For example, if 0.063 lb ai/A is the normal use rate for crops, then an appropriate concentration to select for resistant individuals would be two applications at the same rate, resulting in 0.125 lb ai/A total treatment.

The combination of two sprayings, large spray volumes, high spray pressures, and an elevated treatment concentration helps minimize the occurrence of escapes, i.e., individuals that are not truly resistant, but that survived the procedure simply because they were inadequately sprayed.

There are advantages to conducting selection with herbicides that possess both soil and foliar activities. The soil activity of the herbicide can be used directly to select for resistant individuals that grow despite the pre-emergence application. Alternatively, a pre-emergence application can be used to eliminate a large percentage of the non-resistant entities, following which a foliar application is made on the surviving individuals. This early thinning of the stand density greatly reduces the problem of spray interception that can otherwise occur within a thick stand of young seedlings, i.e., the possibility of a seedling that is physically shielded from the spray by other seedlings.

Using both soil and foliar application of a suitable herbicide also reduces the problem of "escapes," because the herbicide's soil activity will often eliminate individuals that might otherwise escape the foliar spray. When using a herbicide having primarily, or only, foliar activity, an additional spraying may be necessary for two reasons. One reason is to eliminate non-resistant individuals that escaped the foliar spray. Also important is the elimination of non-resistant individuals from late-sprouting seed. A plant that grows from a seed that sprouts after spraying will not be controlled by a herbicide having only foliar activity. Within two weeks, such a plant may reach a size that makes it appear to be a resistant mutant that survived the foliar treatment. If a second foliar spraying either is undesirable or is not feasible, an alternative is to leave a small area of the field unsprayed when applying the first application, to provide a direct standard for determining the size that resistant seedlings should achieve during the intervening period.

Using a herbicide with both soil and foliar activity also presents the opportunity to select efficiently for both pre-emergence and post-emergence resistance within the same individual plants. This selection is accomplished by applying sequential applications. If performed properly, the likelihood will then be high that individuals surviving sequential applications are resistant to both pre- and post-emergence treatments with that herbicide, rather than escapes.

As the selection procedure is in progress, care should be taken that the few surviving individuals are not eaten by birds or insects. Avoiding such predation is important for both post-emergence and pre-emergence treatments. Sound-making devices may be used to drive away birds, such as blackbirds, that consume rice seeds and small seedlings. Insects such as fall armyworms and rice water weevils also may kill small survivors, and the application of an insecticide on a preventative basis is frequently desirable. Daily monitoring of the situation should be undertaken if an investigator chooses not to use bird-discouraging devices or insecticides preventatively.

Assays for Total AHAS Activity

The procedures used to assay the activity of the acetohydroxyacid synthases from various rice lines as reported below were substantially as described in B. K. Singh et al., "Assay of Acetohydroxyacid Synthase," *Analytical Biochemistry*, vol. 171, pp. 173-179 (1988), except as noted. In the first paragraph of Singh's "Materials and Methods," instead of corn suspension culture cells, shoot tissues from greenhouse-grown rice seedlings at the 3-4 leaf stage of development, or rice suspension culture cells were used. For shoot tissues, 40.0 or 50.0 grams (fresh weight) of tissue were extracted in the same manner for each of the breeding lines; for Cypress suspension cells, 16.0 grams of cells were used, harvested eight days after subculture. At the suggestion of the first author, B. K. Singh (personal communication), the desalting step mentioned at the bottom of Singh's first column under "Materials and Methods" was eliminated. Pursuit™ herbicide (imazethapyr, also known as Newpath™) or Arsenal™ herbicide (imazapyr) was included in the "standard reaction mixture" for the AHAS assay in various concentrations. Colorimetric absorbance was measured at 520 nm. Checks were made of direct acetoin formation during the enzyme assay.

The following nine rice lines have been assayed in this manner to date: the non-resistant Cypress line (the parental line for some of the herbicide resistant lines), ATCC 97523, PTA-904, PTA-905, PTA-902, PTA-903, PTA-906, PTA-907, and PTA-908. Some assays were conducted at different times, and assays at some herbicide concentrations were repeated. Differences were noted among the lines with respect to total AHAS enzyme activity and the levels of herbicide resistance. In the modified Singh assay for total AHAS activity, using crude enzyme extract, in the absence of herbicide, most (but not all) of the herbicide-resistant lines expressed greater total AHAS activity than did the non-resistant Cypress line. Following treatment with the herbicides Pursuit™ (imazethapyr, also known as Newpath™) or Arsenal™ (imazapyr), the reduction in AHAS activity was greater in the Cypress line than in any of the resistant lines assayed. For the line that has appeared to have the highest resistance in testing to date, PWC23 (PTA-905), enzyme activity in the presence of very high herbicide levels (1000 μM of either imazethapyr or imazapyr) was similar to the enzyme activity of the nonresistant Cypress line in the absence of any herbicide. All the resistant lines assayed expressed resistance to both imazethapyr and imazapyr, while the nonresistant Cypress line was sensitive to both herbicides. Results are shown in Table 5. In Table 5, the first row ("No herbicide") is reported as absorbance at 520 nm. All other entries in a given column (i.e., for a given line of rice) are reported as a percentage of the absorbance for the same rice line in the absence of herbicide.

TABLE 5

Total AHAS Activity, Crude Enzyme Extracts, measured as absorbance at 520 nm

| | Cypress | ATCC 97523 (93AS3510) | ATCC PTA-904 (PWC16) | ATCC PTA-905 (PWC23) | ATCC PTA-902 (CMC29) | ATCC PTA-903 (CMC31) | ATCC PTA-906 (WDC33) | ATCC PTA-907 (WDC37) | ATCC PTA-908 (WDC38) |
|---|---|---|---|---|---|---|---|---|---|
| No herbicide | 0.766 | 0.837 | 0.713 | 1.107 | 0.811 | 1.038 | 0.851 | 1.226 | 0.822 |
| 50 μM imazethapyr | 63% | 101% | 95% | 99% | 92% | 84% | 89% | 92% | 95% |

TABLE 5-continued

Total AHAS Activity, Crude Enzyme Extracts,
measured as absorbance at 520 nm

| | Cypress | ATCC 97523 (93AS3510) | ATCC PTA-904 (PWC16) | ATCC PTA-905 (PWC23) | ATCC PTA-902 (CMC29) | ATCC PTA-903 (CMC31) | ATCC PTA-906 (WDC33) | ATCC PTA-907 (WDC37) | ATCC PTA-908 (WDC38) |
|---|---|---|---|---|---|---|---|---|---|
| 100 µM imazethapyr (first replicate) | 54% | 92% | 83% | 88% | 88% | 82% | 85% | 86% | 90% |
| 100 µM imazethapyr (second replicate) | 58% | 91% | 92% | 93% | 93% | 87% | 86% | — | — |
| 1000 µM imazethapyr | 56% | 78% | 78% | 80% | 84% | 81% | 82% | 64% | 66% |
| 50 µM imazapyr | 63% | 91% | 90% | 95% | 92% | 86% | 88% | 84% | 81% |
| 100 µM imazapyr | 57% | 83% | 83% | 88% | 84% | 80% | 74% | 78% | 78% |
| 1000 µM imazapyr | 45% | 68% | 76% | 75% | 75% | 68% | 73% | 66% | 66% |

The results shown in Table 5 clearly show that each of the resistant lines listed in that Table (ATCC 97523, ATCC PTA-904, etc.) contains a resistant mutant AHAS enzyme. The lowest concentrations tested, 50 µM of imazethapyr or imazapyr, reduced the activity of the non-resistant line's AHAS to about 63% of control—a reduction in activity that is more than ample to be lethal to plants in the field. By contrast, the resistant lines had AHAS activities ranging from 84% to 101% of control at these herbicide concentrations. Even at the highest herbicide concentrations tested, 1000 µM, enzyme activities in the resistant plants ranged from 64% to 84%, versus 45% or 56% for the non-resistant line. Put differently, each of the resistant plants showed higher AHAS activity at the extremely high herbicide concentration of 1000 µM than the AHAS activity of the non-resistant line at the lowest herbicide rate tested, 50 µM. In fact, the absolute activity exhibited by the most resistant line, PTA-905, at the highest 1000 µM herbicide rates tested (activities of 0.883 for imazethapyr and 0.834 for imazapyr) were higher than the AHAS activity for the non-resistant Cypress line in the absence of any herbicide (0.766).

The results given in Table 5 therefore clearly demonstrate that the herbicide resistance characteristics of at least the resistant rice lines listed in Table 1 were due to a resistant mutant AHAS enzyme.

Germination Inhibition Levels

Pre-emergence herbicide applications were tested to identify the levels of two different herbicides that would completely inhibit germination for several rice lines. Seed of each line tested was germinated in a plastic disposable petri dish containing 8 mL of herbicide solution and a layer of Whatman No. 4 filter paper. The fungicide Vitavax 200 at a concentration of 0.5 mL/L was added to the incubation solutions to inhibit fungal growth. Untreated controls were incubated in solutions containing fungicide but no herbicide. Twenty seeds were placed in each of 3 replicate dishes per treatment, and were incubated at 25° C. under 16 hour: 8 hour light/dark photoperiods at a fluorescent light intensity of 15 micro-Einsteins per square meter per second. (One Einstein=1 mole of photons.) Treatments were evaluated 11 days after incubation. The results of these pre-emergence experiments are shown in the Table 6, which indicates the herbicide concentrations, in parts per million, needed to completely inhibit the germination of the lines tested.

TABLE 6

Herbicide Concentrations (ppm) needed to completely inhibit germination.

| | Imazapic (Cadre ™) | Imazethapyr (Pursuit ™ or Newpath ™) |
|---|---|---|
| Cypress | 0.5 | 1 |
| ATCC 97523 (93AS3510) | 10 | 10 |
| ATCC PTA-904 (PWC16) | 60 | 80 |
| ATCC PTA-905 (PWC23) | 90 | 100 |
| ATCC PTA-902 (CMC29) | 50 | 90 |
| ATCC PTA-903 (CMC31) | 70 | 60 |
| ATCC PTA-906 (WDC33) | 50 | 70 |
| ATCC PTA-907 (WDC37) | 50 | 60 |
| ATCC PTA-908 (WDC38) | 30 | 30 |

As shown Table 6, each of the lines ATCC PTA-904, ATCC PTA-905, ATCC PTA-902, ATCC PTA-903, ATCC PTA-906, ATCC PTA-907, and ATCC PTA-908 exhibited substantially higher resistance to pre-emergence applications of the herbicides imazapic and imazethapyr than did ATCC 97523-higher by a factor of 3 to 10. Also note that the pre-emergence resistance characteristics of each of these seven lines to imazapic and imazethapyr clearly demonstrate that they are different from the line ATCC 97523; similarly, see also the results reported in Tables 7 and 8 below.

Further Greenhouse and Field Tests

The post-emergence resistance of the new lines has also been tested: in peat pots in a greenhouse, and on plants in the field. In the peat pot test, the tolerance of fourth generation ($M_4$) plants to various post-emergence imidazolinone herbicide treatments was tested. Individual seedlings, in 3 replicate peat pots per treatment, were sprayed at the 2-3 leaf stage with 0×, 5×, 10×, 15×, and 20× herbicide treatments. Plants were rated 42 days after treatment. The values listed in Table 7 below were the highest tested rates that were tolerated with no visible injury, in some cases accompanied by a value in parentheses giving a higher rate at which the plants survived, but with injury.

TABLE 7

Highest Rates of Post-Emergence Herbicide Treatment Tolerated without visible injury

|  | Cypress | ATCC 97523 (93AS3510) | ATCC PTA-904 (PWC16) | ATCC PTA-905 (PWC23) | ATCC PTA-902 (CMC29) | ATCC PTA-903 (CMC31) | ATCC PTA-906 (WDC33) | ATCC PTA-907 (WDC37) | ATCC PTA-908 (WDC38) |
|---|---|---|---|---|---|---|---|---|---|
| Imazethapyr (Pursuit) | All died at 5X | All died at 5X | 10X (survived 15X) | 15X (survived 20X) | 15X (survived 20X) | 10X (survived 15X) | 15X (survived 20X) | 10X (survived 15X) | All died at 5X |
| Imazamox (Raptor) | All died at 5X | All died at 5X | All died at 5X | 5X (survived 10X) | injured at 5X | 5X (survived 10X) | 5X | 5X | 10X |
| Imazapyr (Arsenal) | All died at 5X | All died at 5X | 10X | 10X | 10X | 10X | 10X | 10X | 10X |
| Imazapic (Cadre) | All died at 5X | All died at 5X | 5X | 10X | 10X | All died at 5X | 5X | 5X (survived 10X) | injured at 5X |

Notes:
(1) Except for imazamox, in each case a 10X application = 0.63 lb ai/A = 706 g ai/ha, and all other rates of application are proportional. For imazamox, a 10X application = 0.32 lb ai/A = 359 g ai/ha.
(2) Because the number of replicates in this particular experiment was low, and because the lines were still segregating, a higher degree of confidence may be aproppriate for the positive results in Table 7 (herbicide tolerance) than for the negative results (herbicide susceptibility).

Field tests were conducted to evaluate the herbicide-resistance of lines PTA-902, PTA-903, PTA-904, PTA-905, and PTA-908. The same tests were conducted on both the non-resistant rice variety Cypress, and the herbicide resistant rice line ATCC 97523. All lines were planted in 1-meter rows, with two replications of each treatment. Post-emergence treatments of various herbicides were applied when the rice was at the 2-3 leaf stage of development. Herbicide applications were made with a backpack sprayer at a spray rate of 15 gallons per acre (163 liters per hectare). Evaluations of herbicide resistance were made as the plants reached the flowering stage, and were based on relative performance as compared to the non-treated control rows of the same lines. Technical difficulties in conducting this set of experiments prevented the acquisition of good data for line PTA-907. Line PTA-906 was evaluated in greenhouse tests, rather than field tests, in order to conserve the limited amount of seed that was available for this line at the time. Individual plants in 5 cm by 5 cm peat pots were sprayed at the 2-3 leaf stage with the same herbicide applications as were used in the post-emergence field tests. Herbicide treatments were also made with a backpack sprayer at a spray rate of 15 gallons per acre (163 liters per hectare). Evaluations of herbicide resistance were made as the plants reached the flowering stage, and were based on relative performance as compared to the non-treated controls of the same lines in the greenhouse. The greenhouse evaluation was conducted twice, and each treatment was replicated. As in the field test, controls were conducted for comparison with non-resistant plants (in this case, the non-resistant Bengal variety was used) and with the earlier ATCC 97523 plants. Results are shown in Table 8. (Several additional herbicide treatments, not shown in Table 8, were also conducted.)

TABLE 8

Post-Emergence Herbicide Tolerance in Field Trials or Greenhouse Trials. Entries give percent injury as compared with untreated controls of the same lines.

|  | Imazapic (Cadre) 0.075 lb ai/A + imazapyr (Arsenal) 0.025 lb ai/A (=84 and 28 g ai/ha, respectively) | Rimsulfuron (Matrix) 0.025 lb ai/A (=28 g ai/ha) |
|---|---|---|
| Cypress (field) | 100% | 100% |
| ATCC 97523 (93AS3510) (field) | 95% | 90% |
| ATCC 203419 (SSC01) (field) | 28% | 18% |
| ATCC 203420 (SSC02) (field) | 60% | 20% |
| ATCC 203421 (SSC03) (field) | 38% | 18% |
| ATCC 203422 (SSC04) (field) | 23% | 18% |
| ATCC 203423 (SSC05) (field) | 75% | 20% |
| ATCC 203424 (SSC06) (field) | 8% | 8% |
| ATCC 203425 (SSC07) (field) | 23% | 75% |
| ATCC 203426 (SSC08) (field) | 15% | 18% |
| ATCC 203427 (SSC09) (field) | 8% | 13% |
| ATCC 203428 (SSC10) (field) | 8% | 18% |
| ATCC 203429 (SSC11) (field) | 48% | 45% |
| ATCC 203430 (SSC12) (field) | 33% | 18% |
| ATCC 203431 (SSC13) (field) | 30% | 20% |
| ATCC 203432 (SSC14) (field) | 63% | 33% |
| ATCC 203433 (SSC15) (field) | 43% | 35% |
| ATCC PTA-904 (PWC16) (field) | 0% | 100% |
| ATCC PTA-905 (PWC23) (field) | 3% | 100% |
| ATCC PTA-902 (CMC29) (field) | 0% | 100% |
| ATCC PTA-903 (CMC31) (field) | 0% | 100% |
| ATCC PTA-908 (WDC38) (field) | 5% | 100% |
| Bengal (greenhouse) | 100% | 100% |
| ATCC 97523 (93AS3510) (greenhouse) | 100% | 60% |

TABLE 8-continued

Post-Emergence Herbicide Tolerance in Field Trials or Greenhouse Trials. Entries give percent injury as compared with untreated controls of the same lines.

|  | Imazapic (Cadre) 0.075 lb ai/A + imazapyr (Arsenal) 0.025 lb ai/A (=84 and 28 g ai/ha, respectively) | Rimsulfuron (Matrix) 0.025 lb ai/A (=28 g ai/ha) |
|---|---|---|
| ATCC PTA-906 (WDC33) (greenhouse) | 3% | 100% |
| ATCC PTA-907 (WDC37) | N/A | N/A |

Sequencing, Cloning, and Plant Transformation

Repeated attempts by the inventor and his colleagues to sequence the rice AHAS coding sequence by PCR amplification of genomic rice DNA over an extended period of time had not been successful. These difficulties have now been overcome by RT-PCR amplification of RNA instead.

The resistant mutant AHAS nucleotide sequences from the rice plants having accession numbers ATCC 97523, 203419, 203420, 203421, 203422, 203423, 203424, 203425, 203426, 203427, 203428, 203429, 203430, 203431, 203432, 203433, PTA-904, PTA-905, PTA-902, PTA-903, PTA-906, PTA-907, and PTA-908 are sequenced and cloned, along with the wild-type AHAS nucleotide sequence from the parental rice varieties AS3510 and Cypress. As of the filing date of the present application, substantial portions of this work have been completed, as described below. The remaining sequencing and cloning will hereafter proceed to completion using techniques known in the art, as described generally below. The sequences that have been obtained to date show the nature and locations of some of the point mutations responsible for the observed herbicide resistant phenotypes.

The parental non-resistant line Cypress has been publicly released by the Louisiana State University Agricultural Center's Rice Research Station, and is widely available commercially. Samples of the parental non-resistant line AS3510 are available upon request without charge from the inventor, Timothy P. Croughan, c/o Louisiana State University Agricultural Center, Rice Research Station, P.O. Box 1429, Crowley, La. 70527-1429, United States. Samples of line AS3510 may also be available from other rice breeding programs or rice germplasm collections.

Example 29

CMC31 (ATCC PTA-903)

Total RNA from the CMC31 line (ATCC accession number PTA-903) was extracted from rice callus tissue culture with the RNEASY Mini Kit (Qiagen Inc., Valencia, Calif.) using ~100 mg of tissue. The manufacturer's "RNeasy Plant Mini Protocol For Isolation of Total RNA from Plant Cells and Tissues, and Filamentous Fungi" was followed. Total RNA was eluted in 50 µl of diethylpyrocarbonate—water solution, for a yield of ~100 µg.

Next, poly A+ RNA (mRNA) was purified from the total RNA with the Oligotex mRNA Mini Kit (Qiagen Inc., Valencia, Calif.) following the Oligotex mRNA Spin-Column Protocol. Buffer amounts used were those recommended by the manufacturer for a Mini Prep size. The mRNA was eluted twice with 25 µL of the OEB buffer from the kit.

Reverse transcriptase-polymerase chain reaction (RT-PCR) results were obtained using Ready-To-Go RT-PCR Beads (Amersham Pharmacia Biotech, Piscataway, N.J.), following the manufacturer's recommended Two-Step protocol for RT-PCR. The PCR primers were based on a published AHAS sequence from *Hordeum vulgare*, GenBank accession no. AF059600. Two primer pairs, HvAls-3 & HvAls-4, and HvAls-3 & HvAls-6 (HvAls-3=TGG CGA GGC ACG GCG CCC; HvAls-4=GAC GTG GCC GCT TGT AAG; HvAls-6=AGT ACG AGG TCC TGC CAT) (SEQ ID NOS 6-8, respectively) produced two products, one approximately 550 and one approximately 1100 base pairs. (The ~550 bp product was a subset of the ~1100 bp product, and confirmed the sequence of the ~1100 bp product in the region of their overlap.) These products were electrophoresed on a 1.5% agarose gel at 70 volts for 90 minutes. The bands were excised and purified with the ZymoClean™ Gel DNA Recovery Kit (Zymo Research, Orange, Calif.), and were eluted in 13 µL of 10 mM Tris buffer.

The gel-extracted PCR products were sequenced using the Big Dye™ kit (PE Applied Biosystems, Foster City, Calif.), using 5 µL of template per PCR primer. The resulting 1095 base sequence was analyzed against previously reported sequences by the Blast Search software (National Center for Biotechnology Information, available at www.ncbi.nlm.nih.gov/blast/). The sequence is given below as SEQ ID NO 1, in the conventional 5'-3' orientation. These 1095 bases represent about half of the coding portion of the AHAS gene. The inferred partial amino acid sequence is given below as SEQ ID NO 15, in the conventional amino terminus-carboxy terminus orientation.

SEQ ID NO 1 is 85% identical at the nucleotide level (902 bases of 1058) to the AHAS sequence for *Zea mays* reported as GenBank accession number X63553; 84% identical (896 bases of 1060 bases) to the AHAS sequence for *Zea mays* reported as GenBank accession number X63554; and 88% identical (603 bases of 678) to the AHAS sequence for *Hordeum vulgare* reported as GenBank accession number AF059600. It is 97% identical (1062 bases of 1088) to the AHAS sequence for *Oryza sativa* var. *Kinmaze* reported as accession number AB049822 (SEQ ID NO 2).

Until the point of the frame shift mutation, SEQ ID NO 15 is 99% identical at the inferred amino acid level (352 amino acids of 355) to the AHAS sequence for wild type *Oryza sativa* var. *Kinmaze* as reported by T. Shimizu et al., "*Oryza sativa* ALS mRNA for acetolactate synthase, complete cds, herbicide sensitive wild type," BLAST accession number AB049822 (April 2001), available through www.ncbi.nlm.nih.gov/blast, SEQ ID NO 3. At amino acid position 627, there is a Ser-Lys substitution in the inferred amino acid sequence for line CMC31, followed by a single-base deletion in the DNA, causing a frame-shift mutation that generally alters the identity of most of the subsequent amino acids (i.e., those between position 627 and the carboxy terminus), and that introduces a "stop" seven codons downstream from the codon for amino acid position 627 (Ser-Lys).

Since the presumptive source of the herbicide resistance mutation has been identified in line CMC31, it is reasonable to infer that the complete coding sequence for this line is the same as that of the "parent" wild type Cypress AHAS (SEQ ID NO 14), except for replacing the AGT codon for serine at amino acid position 627 with the substitution and deletion A-A seen at the corresponding position in SEQ ID NO 1. The inferred complete AHAS coding sequence for line CMC31 is listed below as SEQ ID NO 20. The corresponding complete inferred amino acid sequence for this herbicide resistant AHAS is listed below as SEQ ID NO 21.

Examples 30-34

PWC16, PWC23, CMC29, WDC33, and WDC38 (ATCC PTA-904, PTA-905, PTA-902, PTA-906, and PTA-908)

Partial cDNA sequences were also determined for the AHAS coding sequence from the lines PWC16, PWC23, CMC29, WDC33, and WDC38 (ATCC PTA-904, PTA-905, PTA-902, PTA-906, PTA-908.)

Leaf material from young greenhouse-grown seedlings was ground, and total RNA was extracted using the "Plant RNEASY Total RNA Midi kit" from Qiagen, following the manufacture's suggested protocols. Next mRNA was purified from the extracted total RNA using Qiagen's "Oligotex mRNA purification system," following the manufacture's suggested protocols.

PCR primers were designed based on an analysis of known AHAS coding sequences from other species. Primers were chosen to correspond to highly conserved regions with low codon degeneracy. These primers were then used in PCR amplification of segments of the sequence from RT-PCR reactions from the isolated rice mRNA.

The mRNA was reverse-transcribed using an oligo-dT primer supplied with Life Technologies' "Superscript First-Strand Synthesis System for RT-PCR." The manufacturer's suggested protocols were followed.

Two primers amplifying approximately 300-350 base pairs were used to amplify the 3' end of the AHAS coding sequence. The resulting DNA fragments were analyzed by agarose gel electrophoresis and were cloned into Topo-TA™ vectors, and a number of individual isolates were sequenced. Sequencing was conducted according to standard protocols, using a Perkin Elmer ABI Prism 310 or a Beckman CEQ2000 automated sequencer. The resulting DNA sequence information was analyzed by commercially available DNA software analysis programs such as Sequencer™.

The observed sequences for lines PWC16, PWC23, CMC29, WDC33, and WDC38 are given below as SEQ ID NOS 9 through 13, respectively. Note that in the wild-type (Cypress) AHAS sequence (SEQ ID NO 14), the codon corresponding to amino acid 627 is AGT, which encodes serine. In each of the sequences of lines PWC16, PWC23, CMC29, WDC33, WDC38 (SEQ ID NOS 9-13), the codon corresponding to amino acid 627 is AAT, which encodes asparagine. This serine-asparagine substitution is believed to be responsible for the herbicide resistance displayed by the AHAS enzyme of these lines.

Since the source of the herbicide resistance mutation has been identified in the lines PWC16, PWC23, CMC29, WDC33, and WDC38, it is reasonable to infer that the complete coding sequences for each of these lines is the same as that of the "parent" wild type Cypress AHAS (SEQ ID NO 14), except for replacing the AGT codon for serine at amino acid position 627 with an AAT codon for asparagine. The inferred complete AHAS coding sequence for each of lines PWC16, PWC23, CMC29, WDC33, and WDC38 is listed below as SEQ ID NO 18. The corresponding complete inferred amino acid sequence for this herbicide resistant AHAS is listed below as SEQ ID NO 19.

Because the different lines PWC16, PWC23, CMC29, WDC33, and WDC38 have demonstrated different levels of herbicide tolerance in the field, it was surprising that the mutations identified for these five lines were all identical. The sequencing of the AHAS coding sequences of these lines will be repeated for verification. In the event that this re-checking demonstrates that one or more of these lines in fact has a mutation in the AHAS coding sequence other than (or in addition to) that leading to the Ser-Asn substitution at amino acid 627, any such mutations are also considered to be within the scope of the present invention.

Example 35

Wild Type Parent (Cypress); and Comparison of Wild Type AHAS Sequences from Different Rice Varieties The AHAS coding sequence for the wild-type "parent" Cypress is given below as SEQ ID NO 14. The inferred amino acid sequence for the wild-type (Cypress) AHAS sequence is listed below as SEQ ID NO 17, corresponding to the translation of the open reading frame of SEQ ID NO 14.

Using BLAST to compare sequences, it was found that there is about 89% identity at the amino acid level between wild-type rice AHAS (SEQ ID NO 17) and the AHAS sequence for *Zea mays* reported as GenBank accession number X63553 (576 amino acids of 641).

It is also interesting to compare the wild type AHAS coding sequence for the rice cultivar Cypress to the wild type AHAS coding sequence reported by T. Shimizu et al., "*Oryza sativa* ALS mRNA for acetolactate synthase, complete cds, herbicide sensitive wild type," BLAST accession number AB049822. The two sequences are 98% identical at the nucleotide level (1955 bases of 1986). The inferred amino acid sequences are 99% identical (640 amino acids of 644). The vast majority of the 31 bases that differ between the two nucleotide sequences are "silent" mutations, i.e., they result in different codons that encode the same amino acids. The "non-silent" differences occur at amino acid 11 (Cypress, Thr; Kinmaze, Ala); amino acid 293 (Cypress, Arg; Kinmaze, Trp); amino acid 401 (Cypress, Asp; Kinmaze, Gln); and amino acid 643 (Cypress, Met; Kinmaze, Val).

Example 36

CMC31 (ATCC PTA-903)

The AHAS coding sequence from line CMC31 was sequenced again, by a different set of workers from those who derived SEQ ID NO 1, using the protocol described below.

1.0 g of fresh tissue from young greenhouse-grown seedlings was ground, and genomic DNA was isolated using the DNeasy Plant Maxi Kit (from Qiagen), following the manufacturer's recommended protocols. The amount of isolated DNA was measured by absorbance reading at 260 nm. 100 ng of DNA was used in a PCR reaction designed to amplify the 3' end of the AHAS coding sequence. The following primers, based on the published sequence of *Oryza sativa* var. *Kinmaze* (GenBank AB049822), were used to amplify the 3' end of the coding sequence: primer RA7, AGTGGCTGTCT-TCGGCTGGTCT (SEQ ID NO 22), and primer RA5, CCTACCACTACCGTCCTGACACAT (SEQ ID NO 23).

The Expand High Fidelity PCR kit from Roche was used to amplify the DNA. DNA from the PCR reaction was checked for correct size using 1% agarose gel electrophoresis. Bands of the expected size were cut from the gel, and the DNA was then purified using the QIAquick Gel Extraction Kit (Qiagen) according to the manufacturer's instructions. Purified DNA was ligated to pCR2.1-TOPO™ vector DNA. After ligation, the DNA was transformed into One Shot™ competent *E. coli* cells. Cells were plated, and grown overnight. The following day single colonies were picked, re-plated and numbered.

E. coli cells were lysed by adding a small quantity of cells to 20 ml of water, and heating to 95° C. for 5 minutes. PCR was then performed on the lysed cells with the primers RA7 and RA5 and Taq polymerase. Colonies that were positive for the inserted DNA were grown overnight, and DNA from these cultures was prepared using the Miniprep Plasmid kit from Qiagen. DNA was checked again by digestion with the restriction enzymes PstI and HindIII.

DNA was sequenced by the Big Dye terminator method (Applied Biosystems, Foster City, Calif.). Primer RA7 was used in the sequencing reaction (in the forward direction). Sequencing was performed on a 377 Perkin Elmer instrument. Sequences were analyzed using Vector NTI Suite 6.

The resulting sequence is given below as SEQ ID NO 16. This time, the sequence showed the same, single nucleotide G-A substitution, resulting in the same Ser-Asn substitution at amino acid position 627, as was seen for each of the lines PWC16, PWC23, CMC29, WDC33, WDC38.

The reason for the discrepancy between SEQ ID NO 1 and SEQ ID NO 16 for line CMC31 is currently unknown. As of the filing date of this application, the scenario that is considered most likely is that the deletion/frame shift mutation shown in SEQ ID NO 1 is correct, and that the Ser-Asn substitution implied by SEQ ID NO 16 resulted from some currently unknown experimental error, for example mis-labeling of a packet of seed. It is also possible, although it is currently considered less likely, that line CMC31 does have the same Ser-Asn substitution seen in the other lines. Repeated sequencing of the AHAS coding sequence from seed that is confirmed to be from line CMC31 will clarify this discrepancy.

Example 37

WDC37 (ATCCPTA-907)

DNA from line WDC37 was isolated, cloned and sequenced as described above for CMC31 (namely, the method using primers RA5 and RA7), except that the DNA from line WDC37 was sequenced by automated dideoxy sequencing, generally according to the method of Sanger et al., *Proc. Natl. Acad. Sci. USA*, vol. 74, pp. 5463-5467 (1977). Reactions were performed with the Applied Biosystems (Foster City, Calif.) Prism Big Dye terminator cycle sequencing kit with AmpliTaq DNA polymerase FS and were electrophoresed on an Applied Biosystems Prism 377 DNA sequencer.

To date, the mutation responsible for herbicide resistance in WDC37 has not been identified. The sequences obtained to date have been indistinguishable from wild type. Possible reasons for this include mis-marked seed, segregation effects causing wild type AHAS sequences to occasionally be picked up in the herbicide resistant line, or a mutation in a different part of the AHAS molecule from that targeted by the PCR primers RA5 and RA7. Repetitions of these sequencing efforts, using fresh seed confirmed to be from WDC37, and including the entire AHAS coding sequence will clarify this discrepancy.

Further Examples

The AHAS coding sequence for ATCC No. 97523 (93AS3510) is given below as SEQ ID NO 24. The inferred amino acid sequence for the ATCC No. 97523 AHAS is listed below as SEQ ID NO 25, corresponding to the translation of the open reading frame of SEQ ID NO 24. Note that in the wild-type (Cypress) AHAS sequence (SEQ ID NO 14), the codon corresponding to amino acid 628 is GGG, which encodes glycine. In the sequence of line 97523 (SEQ ID NO 24), the codon corresponding to amino acid 628 (in SEQ ID NO 25) is GAG, which encodes glutamic acid. This glycine-glutamic acid substitution is believed to be responsible for the herbicide resistance displayed by the AHAS enzyme of the ATCC No. 97523 line.

The complete DNA sequences and inferred amino acid sequences of the AHAS molecules for each of the rice plants having ATCC Accession Nos. 203419, 203420, 203421, 203422, 203423, 203424, 203425, 203426, 203427, 203428, 203429, 203430, 203431, 203432, 203433, PTA-904, PTA-905, PTA-902, PTA-906, PTA-907, and PTA-908 will also be determined (or redetermined) using generally similar protocols, or other techniques well known in the art.

Cloning into Other Green Plants.

These and other cloned, herbicide-resistant AHAS nucleotide sequences from rice plants may be used to transform herbicide resistance into other rice plants, as well as transforming other green plants generally to impart herbicide resistance. Herbicide resistance may be introduced into other rice plants, for example, either by traditional breeding, back-crossing, and selection; or by transforming cultivars with the cloned resistant AHAS nucleotide sequences. Direct transformation of rice cultivars has the potential to allow quick introduction of the herbicide resistance characteristics into a variety, without requiring multiple generations of breeding and back-crossing to attain uniformity.

Furthermore, at least in the case of rice transformed via the preferred vector of U.S. Pat. No. 5,719,055, much of the concern that some individuals have expressed over the propriety of the genetic transformation of agricultural species should be alleviated. The transformation of a rice variety with a nucleotide sequence from another rice plant would only speed up what could also be accomplished through traditional breeding techniques. No coding sequences exogenous to rice plants would be introduced, merely the efficient introduction of a rice AHAS allele from another rice plant. The use of the vector of U.S. Pat. No. 5,719,055 allows the introduction of the desired coding sequence only, without any other coding sequences being introduced into the genome. No antibiotic-resistance genes or other markers will be needed: selection for successful transformation events can be based directly on the herbicide resistance itself. As explained more fully in U.S. Pat. No. 5,719,055, the only sequences that need be introduced in addition to the nucleotide sequence of interest are flanking insertion sequences recognized by the transposase used by the vector. The insertion sequences are not themselves coding sequences, and are inert in the absence of the transposase; furthermore, the vector is designed so that the transposase is not encoded by any DNA that is inserted into the transformed chromosome. The only portion of the transformed DNA that will be active following transformation is the resistant AHAS nucleotide sequence itself. That AHAS nucleotide sequence is derived from rice, so the transformed rice plants will not be "transgenic" in the usual sense of carrying coding DNA from another species.

It will be understood by those skilled in the art that the nucleic acid sequences of the resistant mutant AHAS enzymes from ATCC Accession Nos. 97523, 203419, 203420, 203421, 203422, 203423, 203424, 203425, 203426, 203427, 203428, 203429, 203430, 203431, 203432, 203433, PTA-904, PTA-905, PTA-902, PTA-903, PTA-906, PTA-907, and PTA-908 are not the only sequences that can be used to confer resistance. Also contemplated are those nucleic acid sequences that encode identical proteins but that, because of the degeneracy of the genetic code, possess different nucleotide sequences. The genetic code may be found in numerous references concerning genetics or biology, including, for example, FIG. 9.1 on page 214 of B. Lewin, *Genes VI* (Oxford University Press, New York, 1997). FIG. 9.3 on page 216 of Lewin directly illustrates the degeneracy of the genetic code. For example, the codon for asparagine may be AAT or AAC.

The sequences may be transformed into a plant of interest with or without some or all of the native *Oryza sativa* AHAS gene's introns, which may be identified by means well known in the art. Introns can affect the regulation of gene expression.

The expression products are preferably targeted to the chloroplasts, which are believed to be the major site for wild type AHAS activity in green plants. The targeting signal sequence normally corresponds to the amino terminal end of the protein expression product, and the corresponding coding sequence should therefore appear upstream of the 5' end of the coding sequence. This targeting is preferably accomplished with the native *Oryza sativa* AHAS signal sequence, but it may also use other plant chloroplast signal sequences known in the art, such as, for example, those disclosed in Cheng et al., *J. Biol. Chem.*, vol. 268, pp. 2363-2367 (1993); see also Comai et al., *J. Biol. Chem.*, vol. 263, pp. 15104-15109 (1988).

The invention also encompasses nucleotide sequences encoding AHAS proteins having one or more silent amino acid changes in portions of the molecule not involved with resistance or catalytic function. For example, alterations in the nucleotide sequence that result in the production of a chemically equivalent amino acid at a given site are contemplated; thus, a codon for the amino acid alanine, a hydrophobic amino acid, may be substituted by a codon encoding another hydrophobic residue, such as glycine, or may be substituted with a more hydrophobic residue such as valine, leucine, or isoleucine. Similarly, changes that result in the substitution of one negatively-charged residue for another, such as aspartic acid for glutamic acid, or one positively-charged residue for another, such as lysine for arginine, can also be expected to produce a biologically equivalent product. See, e.g., FIG. 1.8 on page 10 of Lewin (1997), showing the nature of the side chains of the "standard" 20 amino acids encoded by the genetic code. (Note also a typographical error in that published figure, namely that the abbreviation for glutamine should be "Gln.")

The invention also encompasses chimeric nucleotide sequences, in which the mutated portion of a resistant rice AHAS nucleotide sequence is recombined with unaltered portions of the AHAS nucleotide sequence from another species.

This invention relates not only to a functional AHAS enzyme having the amino acid sequence encoded by a mutant, resistant AHAS nucleotide sequence described in this specification, including for example those from one of the identified rice plants deposited with ATCC, but also to an enzyme having modifications to such a sequence resulting in an amino acid sequence having the same function (i.e., a functional AHAS enzyme, with resistance to at least some herbicides that normally interfere with AHAS), and about 60-70%, preferably 90% or greater homology to the sequence of the amino acid sequence encoded by the AHAS nucleotide sequence of at least one such ATCC-deposited rice line, more preferably about 95% or greater homology, particularly in conserved regions such as, for example, a putative herbicide binding site. "Homology" means identical amino acids or conservative substitutions (e.g., acidic for acidic, basic for basic, polar for polar, nonpolar for nonpolar, aromatic for aromatic). The degree of homology can be determined by simple alignment based on programs known in the art, such as, for example, GAP and PILEUP by GCG, or the BLAST software available through the NIH internet site. Most preferably, a certain percentage of "homology" would be that percentage of identical amino acids.

A particular desired point mutation may be introduced into an AHAS coding sequence using site-directed mutagenesis methods known in the art. See, e.g., R. Higuchi, "Recombinant PCR," pp. 177-183 in M. Innis et al. (Eds.), PCR Protocols: A Guide to Methods and Applications, Academic Press (1990); U.S. Pat. No. 6,010,907; Kunkel, *Proc. Natl. Acad. Sci. USA*, vol. 82, pp. 488-492 (1985); Kunkel et al., *Methods Enzymol.*, vol. 154, pp. 367-382 (1987); U.S. Pat. No. 4,873, 192; Walker et al. (Eds.), *Techniques in Molecular Biology* (MacMillan, New York, 1983); or the Genoplasty™ protocols of ValiGen (Newtown, Pa.).

Isolated AHAS DNA sequences of the present invention are useful to transform target crop plants, and thereby confer resistance. A broad range of techniques currently exists for achieving the direct or indirect transformation of higher plants with exogenous DNA, and any method by which one of the novel sequences can be incorporated into the host genome, and stably inherited by its progeny, is contemplated by the present invention.

The cloned AHAS coding sequence should be placed under the control of a suitable promoter, so that it is appropriately expressed in cells of the transformed plant. It is expected that the most suitable promoter would be a native AHAS promoter. The native AHAS promoter could be that of any plant, for example, the native AHAS promoter from the plant that is being transformed. Alternatively, it is expected that the native rice AHAS promoter will function appropriately in other green plants generally (including, e.g., both monocots and dicots), and that for simplicity the same rice AHAS promoter may be used when transforming any plant species of interest.

The native AHAS promoter, whether that from rice or from another plant, may be isolated as follows. AHAS cDNA is isolated and amplified, for example by PCR or by cloning into a bacterium such as *E. coli* or *Agrobacterium*, and is denatured into single-stranded DNA. A genomic library is prepared for rice or other plant of interest using standard techniques, and Southern blotting is used to hybridize segments of genomic DNA to the AHAS cDNA. The hybridizing DNA segments are amplified through PCR and sequenced. The promoter will be found in segments upstream of the transcription initiation site.

Note that it is not necessary to identity the sequence of the AHAS promoter precisely. Where the upstream sequence that constitutes the promoter has not been precisely identified, the promoter will nevertheless be included by taking a sufficiently large number of bases "upstream" of the transcription initiation site. The fact that "extra" bases may also be included in addition to the promoter is acceptable. The number of upstream bases needed to encompass a particular promoter may readily be determined in a particular case, and for the reasons just given, the precise number of bases is not crucial. In general, sequences of about 500, 1000, or 1500 bases upstream from the transcription initiation site should suffice in most cases.

As a further alternative, a constitutive promoter could be used to control the expression of the transformed mutant AHAS coding sequence. Promoters that act constitutively in plants are well known in the art, and include, for example, the cauliflower mosaic virus 35S promoter.

Transformation of plant cells can be mediated by the use of vectors. A common method for transforming plants is the use of *Agrobacterium tumefaciens* to introduce a foreign nucleotide sequence into the target plant cell. For example, a mutant AHAS nucleotide sequence is inserted into a plasmid vector containing the flanking sequences in the Ti-plasmid T-DNA. The plasmid is then transformed into *E. coli*. A triparental mating is carried out among this strain, an *Agrobacterium* strain containing a disarmed Ti-plasmid containing the virulence functions needed to effect transfer of the AHAS-containing T-DNA sequences into the target plant chromosome, and a second *E. coli* strain containing a plasmid having sequences necessary to mobilize transfer of the AHAS construct from *E. coli* to *Agrobacterium*. A recombinant *Agrobacterium* strain, containing the necessary sequences for plant transformation, is used to infect leaf discs. Discs are grown on selection media and successfully transformed regenerants are identified. The recovered plants are resistant to the effects of herbicide when grown in its presence.

Plant viruses also provide a possible means for transfer of exogenous DNA.

Direct uptake of DNA by plant cells can also be used. Typically, protoplasts of the target plant are placed in culture in the presence of the DNA to be transferred, along with an agent that promotes the uptake of DNA by protoplasts. Such agents include, for example, polyethylene glycol and calcium phosphate.

Alternatively, DNA uptake can be stimulated by electroporation. In this method, an electrical pulse is used to open temporary pores in a protoplast cell membrane, and DNA in the surrounding solution is then drawn into the cell through the pores. Similarly, microinjection can be used to deliver the DNA directly into a cell, preferably directly into the nucleus of the cell.

In many of these techniques, transformation occurs in a plant cell in culture. Subsequent to the transformation event, plant cells must be regenerated to whole plants. Techniques for the regeneration of mature plants from callus or protoplast culture are known for a large number of plant species. See, e.g., Handbook of Plant Cell Culture, Vols. 1-5, 1983-1989 McMillan, N.Y.

Alternate methods are also available that do not necessarily require the use of isolated cells and plant regeneration techniques to achieve transformation. These are generally referred to as "ballistic" or "particle acceleration" methods, in which DNA-coated metal particles are propelled into plant cells by either a gunpowder charge (see Klein et al., *Nature* 327: 70-73, 1987) or by electrical discharge (see EPO 270 356). In this manner, plant cells in culture or plant reproductive organs or cells, e.g. pollen, can be stably transformed with the DNA sequence of interest.

In certain dicots and monocots, direct uptake of DNA is the preferred method of transformation. For example, in maize or rice the cell wall of cultured cells is digested in a buffer with one or more cell wall-degrading enzymes, such as cellulase, hemicellulase, and pectinase, to isolate viable protoplasts. The protoplasts are washed several times to remove the degrading enzymes, and are then mixed with a plasmid vector containing the nucleotide sequence of interest. The cells can be transformed with either PEG (e.g. 20% PEG 4000) or by electroporation. The protoplasts are placed on a nitrocellulose filter and cultured on a medium with embedded maize cells functioning as feeder cultures. After 2-4 weeks, the cultures in the nitrocellulose filter are placed on a medium containing herbicide and maintained in the medium for 1-2 months. The nitrocellulose filters with the plant cells are transferred to fresh medium with herbicide and nurse cells every two weeks. The un-transformed cells cease growing and die after a time.

Other methods of transforming plants are described in B. Jenes et al, and in S. Ritchie et al., in S.-D. Kung et al. (Eds.), *Transgenic Plants*, vol. 1, *Engineering and Utilization*, Academic Press, Inc., Harcourt Brace Jovanovich (1993); and in L. Mannonen et al., *Critical Reviews in Biotechnology*, vol. 14, pp. 287-310 (1994). See also the various references cited on pages 15-17 of published international patent application WO 00/26390, each of which is incorporated by reference.

A particularly preferred transformation vector, which may be used to transform seeds, germ cells, whole plants, or somatic cells of monocots or dicots, is the transposon-based vector disclosed in U.S. Pat. No. 5,719,055. This vector may be delivered to plant cells through one of the techniques described above or, for example, via liposomes that fuse with the membranes of plant cell protoplasts.

The present invention can be applied to transform virtually any type of green plant, both monocot and dicot. Among the crop plants and other plants for which transformation for herbicide resistance is contemplated are (for example) rice, maize, wheat, millet, rye, oat, barley, sorghum, sunflower, sweet potato, casava, alfalfa, sugar cane, sugar beet, canola and other *Brassica* species, sunflower, tomato, pepper, soybean, tobacco, melon, lettuce, celery, eggplant, carrot, squash, melon, cucumber and other cucurbits, beans, cabbage and other cruciferous vegetables, potato, tomato, peanut, pea, other vegetables, cotton, clover, cacao, grape, citrus, strawberries and other berries, fruit trees, and nut trees. The novel sequences may also be used to transform turfgrass, ornamental species, such as petunia and rose, and woody species, such as pine and poplar.

Enzyme Purification, Analysis, and Sequencing

Preliminary data (reported below) suggest that rice may produce at least three different AHAS isozymes, which would presumably be encoded by different AHAS nucleotide sequences in the rice genome, although the experiments completed as of the filing date of this application do not yet rule out the possibility that different isozymes could be encoded by a single gene, but produced by separate pathways such as alternative splicing of mRNA, or alternative post-translational processing of polypeptides. Incidentally, it is believed that the present patent application is the first published report that rice appears to have at least three different AHAS isozymes. To the inventor's knowledge, it had not previously been reported that rice had more than one form of the AHAS enzyme.

The sequence obtained for the first isozyme will be used to prepare primers for amplifying and sequencing the other isozymes, either from genomic DNA or from cDNA. Greater levels of resistance may be obtained in plants carrying resistant alleles in multiple AHAS nucleotide sequences. Such plants may readily be bred by crossing and backcrossing through means known in the art, or by site-directed mutagenesis. Even greater levels of resistance may be obtained by crossing such a "double mutant" or "triple mutant" with the metabolic-based herbicide resistant rice lines disclosed in U.S. Pat. No. 5,545,822, as typified by the rice having ATCC accession number 75295, as discussed earlier, since its metabolic resistance is based on a separate, currently unknown mechanism.

The preliminary isozyme data reported below suggests that the resistance seen in some of the novel lines may have resulted from mutations in different AHAS isozymes. For example, in the non-resistant parental Cypress line, the putative AHAS-1 isozyme (defined below) appeared to account for about 25% of the total activity, while putative AHAS-2 and putative AHAS-3 together appeared to account for about 75% of total activity. By contrast, in ATCC 97523, putative AHAS-1 appeared to account for about 75% of total activity, with putative AHAS-2 and putative AHAS-3 together appearing to account for about 25% of total activity; while in PWC23 putative AHAS-1 appeared to account for about 95% of total activity, with putative AHAS-2 and putative AHAS-3 together appearing to account for about 5% of total activity.

It is hypothesized that the amino acid end-products of the process catalyzed by AHAS-1 may cause feedback suppression of AHAS-2 and AHAS-3 in the lines with low activities in the latter two isozymes.

In addition, total AHAS activity in many of the novel resistant lines exceeded that in the non-resistant Cypress parent.

Preliminary Note:

It is believed that rice possesses multiple AHAS isozymes, perhaps two or three such isozymes. The procedures reported under the present heading ("Enzyme Purification, Analysis, and Sequencing") were conducted to attempt to separate the different isozymes. Since these experiments were conducted, it has come to the inventor's attention (B. J. Singh, private communication) that these particular isozyme separation procedures may be subject to artifacts, to experimental errors. As of the filing date of the present international Patent Cooperation Treaty application, this question had not been resolved to the inventor's satisfaction. While it is believed that rice does have multiple AHAS isozymes, the particular experimental data reported in this section, concerning enzyme purification and separation, may or may not be a reliable indication of that AHAS isozyme activity. Should these particular experimental data turn out not to be reliable, then other enzymatic purification and separation procedures known in the art may be substituted. Furthermore, it is important to note that the other results reported in this patent application do not depend upon whether the isozyme data reported in the present section are correct or incorrect.

The procedures used to separate the acetohydroxyacid synthase isozymes in rice from one another were substantially as described in B. Singh et al., "Separation and Characterization of Two Forms of Acetohydroxyacid Synthase from Black Mexican Sweet Corn Cells," *J. Chromatogr.*, vol. 444, pp. 251-261 (1988). Suspension cells, or shoot tissues from greenhouse-grown plants at the 3-4 leaf stage of development, were used for crude enzyme extraction. For extraction from suspension cells, 16 grams of cells were harvested 8 days after subculturing of Cypress suspension cultures. Following crude enzyme pelleting, the enzyme was re-suspended in 25 mM potassium phosphate buffer (pH=7.0) containing 5 mM pyruvate, 5 mM EDTA, and 5 µM FAD (flavin adenine dinucleotide). The isozymes were then separated by HPLC on a Waters 600 chromatograph (Amersham Pharmacia Biotech, Piscataway, N.J.) at an eluent flow rate of 1 mL per minute. Following filtration through a 0.45 µm Millex (Millipore, Bedford, Mass.) syringe filter, 2.00 mL of each sample was loaded onto a Mono Q HR 5/5 column (5×0.5 cm) (Amersham Pharmacia Biotech, Piscataway, N.J.) that had been pre-equilibrated with the same buffer. After injection and elution of 5 mL of eluent, a linear 20-minute gradient of 0-0.5 M potassium chloride in equilibration buffer was initiated. One-mL fractions were collected and assayed for AHAS enzyme activity. Additional purification procedures that are standard in the art may optionally be used, such as gel electrophoresis or additional HPLC separations.

Several rice lines have been assayed in this manner. The remaining resistant lines will be assayed in the same manner. Each of the sampled lines appeared to have at least three AHAS isozymes. Differences were noted among the lines with respect to total AHAS enzyme activity, the overall level of herbicide resistance, and the activity of the individual isozymes.

Table 9 depicts qualitatively the relative activities seen in several lines for the three putative isozymes that have been tentatively designated "AHAS-1," "AHAS-2," and "AHAS-3." (The numbering corresponds to the order in which the enzymes eluted from the HPLC.)

TABLE 9

Relative AHAS Isozyme Activity,
reported qualitatively on a 5-point scale, based on absorbance at 520 nm

|  | Cypress | ATCC 97523 | PWC16 | PWC23 | CMC29 | CMC31 | WDC33 |
| --- | --- | --- | --- | --- | --- | --- | --- |
| AHAS-1 | 1 | 2 | 0 | 5 | 3 | 0+ | 0+ |
| AHAS-2 | 1 | 0+ | 1 | 0 | 0+ | 1 | 0+ |
| AHAS-3 | 2 | 0+ | 1+ | 0+ | 1− | 2 | 0+ |

To prepare isolated AHAS isozymes for direct amino acid sequencing, the same protocols were used as described above, except that aliquots were combined from four separate runs through the HPLC (4 injections, 2 mL/injection). The combined aliquots were concentrated by cool evaporation of the liquid using a Savant Instruments SpeedVac (Farmingdale, N.Y.). The concentrated samples were then run through a PD-10 Sephadex G-25 (Amersham Pharmacia Biotech, Piscataway, N.J.) desalting column prior to freeze-drying. The amino acid sequence of each of the three isozymes will be determined by Edman degradation. (The 4×1.0 mL=4.0 mL combined aliquot having the highest peak for each isozyme was selected for amino acid sequencing, on the assumption that this aliquot had a relatively high and a relatively pure concentration of the particular isozyme.)

The Edman degradation technique and related protein analysis techniques are well known in the peptide art. Briefly, the amino-terminal residue of a polypeptide is labeled and cleaved from the peptide without disrupting the peptide bonds between the other amino acid residues. The Edman degradation sequentially removes one residue at a time from the amino end of a polypeptide. Phenyl isothiocyanate reacts with the uncharged terminal amino group of the peptide to form a phenylthiocarbamoyl derivative. Under acidic conditions, a cyclic derivative of the terminal amino acid is liberated, which leaves an intact peptide shortened by one amino acid. The cyclic compound is a phenylthiohydantoin (PTH)-amino acid. The PTH-amino acid is then identified by standard procedures. See generally R. Meyers (ed.), Molecular Biology and Biotechnology, pp. 731-741, and 764-773 (1995).

The polypeptide sequencing results will be used to complement the results from the mRNA RT-PCR sequencing described previously. The amino acid sequences will be confirmed by designing DNA primers from the observed amino acid partial sequences, cloning the AHAS nucleotide sequences from genomic or cDNA libraries of the wild type and mutant rice lines, and sequencing the nucleotide sequences thus cloned. The sequences will also be confirmed by comparing the complementarity of the sequences determined for the positive strands and the negative strands of each.

The amino acid sequence data will be used to design primers for PCR amplification of the putative AHAS isozymes, along with the data from the known AHAS coding sequence (e.g. SEQ ID NO. 14). Also, it is possible through standard techniques to digest the protein into smaller pieces, which are then sequenced individually to give amino acid sequences for internal regions of the protein.

Proposed Mechanisms of Action

Preliminary Note:

The discussion under the present heading ("Proposed Mechanisms of Action") is subject to the same caveats mentioned under the previous heading concerning the isozyme purification and separation protocols that have been used to date. The validity of the other data reported here do not depend on these proposed mechanisms of action.

Without wishing to be bound by the theory presented in this section, the following hypotheses are consistent with the preliminary isozyme data described under the previous heading: Rice appears to have at least three AHAS isozymes, isozymes that are normally produced by a rice plant at different activity levels. Except for ATCC 75295, the mutations discovered by the present inventor for herbicide resistance in rice appear to be mutations in the AHAS enzymes themselves, rather than mutations arising from another source such as a mutation in a metabolic pathway or a mutation in the regulation of an AHAS gene. In some of the resistant mutants, at least in the absence of herbicide, the relative activity levels of the three AHAS isozymes appear not to be substantially altered compared to wild-type, perhaps because the resistance mutation in these lines appears in the "predominant" isozyme. In at least one of the resistant mutants, the relative activities of all three isozymes appeared to be lower than wild-type.

On the other hand, there are resistant mutants in which one of the "alternate" isozymes appears to be preferentially produced, for unknown reasons. The increased activity of this mutant isozyme causes feedback inhibition of the other two isozymes; i.e., higher levels of amino acid products resulting from the activity of the mutant isozyme inhibit the expression of the other two isozymes through normal regulatory feedback mechanisms.

The herbicide appears to act by strongly (or even irreversibly) binding to the AHAS molecule. This binding does not completely eliminate AHAS activity, even in wild-type AHAS, although herbicide binding does reduce the activity (~50%) sufficiently to kill wild-type plant cells. There appears to be a "saturation" point in the herbicide concentration, e.g. ~10 µM (depending on the herbicide), above which activity of wild-type enzyme does not decrease substantially.

By contrast, even at much higher herbicide concentrations, e.g., even up to ~1000 µM, the activity of some of the mutant AHAS enzymes is still roughly comparable to the activity of wild-type enzyme in the absence of any herbicide, suggesting that the mutant AHAS enzymes do not bind the herbicides as strongly. Yet even those mutant AHAS enzymes that normally show strong resistance to AHAS-acting herbicides are nevertheless susceptible to some of the AHAS-acting herbicides. This property suggests that the resistance of that enzyme to certain herbicides is due to a weaker binding affinity between those herbicides and the mutant enzyme; and not, for example, to pre-herbicide overproduction of the AHAS-catalyzed amino acids that allows the plant cells to survive on "reserves" of those amino acids until the effect of the herbicide has worn off. Were such an overproduction responsible for the herbicide resistance, then across-the-board resistance to all AHAS-acting herbicides would be expected.

Miscellaneous

Through routine breeding practices known in the art, progeny will be bred from each of the resistant parent rice lines identified above. Once progeny are identified that are demonstrably resistant, those progeny will be used to breed varieties for commercial use. Crossing and back-crossing resistant plants with other germplasm through standard means will yield herbicide-resistant varieties and hybrids having good productivity and other agronomically desirable properties. Alternatively, direct transformation into a variety or into a parent of a hybrid having agronomically desirable properties may be employed, as direct transformation can accelerate the overall selection and breeding process.

Because red rice and commercial rice belong to the same species, the planting of a herbicide-resistant commercial rice crop entails some risk that herbicide resistance would be transferred to red rice. However, rice is self-pollinating, and the frequency of outcrossing is low, even between immediately adjacent plants flowering in synchrony. The likelihood of transferring resistance to red rice could be minimized by breeding resistant varieties that flower significantly earlier than does red rice (e.g., using conventional breeding techniques, or by tissue culture such as another culture). Maintaining an early-maturing phenotype in resistant varieties, for example, will be desirable to reduce the likelihood of outcrossing to red rice. In addition, breeding higher levels of resistance (e.g., by crossing lines with different AHAS isozymes with one another, or crossing lines with resistant AHAS enzymes with the metabolic resistance of ATCC 75295) will allow control of the outcrossed red rice by applying higher herbicide rates than the outcrossed red rice will tolerate.

If a strain of red rice should nevertheless develop that is resistant to the same herbicides as resistant commercial rice, the plants can always be treated with a broad range of other available herbicides—particularly if the resistant red rice were discovered early, before having much opportunity to propagate.

The same or analogous techniques should be employed to inhibit the out-crossing of herbicide resistance into "weedy" or wild relatives of other crop species.

Because each of the herbicides tested inhibits the activity of acetohydroxyacid synthase, and because resistance to each of these herbicides has been demonstrated in the novel lines, it is expected that the novel herbicide resistant rice will show resistance to other herbicides that normally inhibit this enzyme. In addition to those discussed above, such herbicides include others of the imidazolinone and sulfonylurea classes, including at least the following: primisulfuron, chlorsulfuron, imazamethabenz methyl, and triasulfuron. Other classes of AHAS herbicides known in the art include triazolopyrimidines, triazolopyrimidine sulfonamides, sulfamoylureas, sulfonylcarboxamides, sulfonamides, pyrimidyloxybenzoates, phthalides, pyrimidylsalicylates, carbamoylpyrazolines, sulfonylimino-triazinyl heteroazoles, N-protected valylanilides, sulfonylamide azines, pyrimidyl maleic acids, benzenesulfonyl carboxamides, substituted sulfonyldiamides, and ubiquinone-o.

As used in the specification and claims, the term "mutation-inducing conditions" refers to conditions that will cause mutations in a plant's genome at rates substantially higher than the background rate. A variety of such conditions are well-known to those in the art. They include, for example, exposing seeds to chemical mutagens or ionizing radiation as previously described. Such conditions also include growing cells in tissue culture (another culture, callus culture, suspension culture, protoplast culture, etc.), with or without deliberately exposing the cells to additional mutation-inducing conditions other than those that are inherent in tissue culture. (It is known that tissue culture is per seconducive to the production of genetic variability, including mutations.) Depending on the particular mutation-inducing conditions used, mutations may best be induced at different stages in the life cycle, e.g., with dry seeds, with pre-germinated seeds, etc.

As used in the specification and claims, the term "imidazolinone" means a herbicidal composition comprising one or more chemical compounds of the imidazolinone class, including by way of example and not limitation, 2-(2-imidazolin-2-yl)pyridines, 2-(2-imidazolin-2-yl)quinolines and 2-(2-imidazolin-2-yl)benzoates or derivatives thereof, including their optical isomers, diastereomers and/or tautomers exhibiting herbicidal activity, including by way of example and not limitation 2-[4,5-dihydro-4-methyl-4-(1-methylethyl)-5-oxo-1H-imidazol-2-yl]-3-quinolinecarboxylic acid (generic name imazaquin); 2-[4,5-dihydro-4-methyl-4-(1-methylethyl)-5-oxo-1H-imidazol-2-yl]-5-ethyl-3-pyridinecarboxylic acid (generic name imazethapyr); and 2-[4,5-dihydro-4-methyl-4-(1-methylethyl)-5-oxo-1H-imidazol-2-yl]-5-(methoxymethyl)-3-pyridinecarboxylic acid (generic name imazamox); 2-[4,5-dihydro-4-methyl-4-(1-methylethyl)-5-oxo-1H-imidazol-2-yl]-3-pyridinecarboxylic acid (generic name imazapyr); 2-[4,5-dihydro-4-methyl-4-(1-methylethyl)-5-oxo-1H-imidazol-2-yl]-5-methyl-3-pyridinecarboxylic acid) (generic name imazameth, also known as imazapic); and the other examples of imidazolinone herbicides given in the specification.

As used in the specification and claims, the term "sulfonylurea" means a herbicidal composition comprising one or more chemical compounds of the sulfonylurea class, which generally comprise a sulfonylurea bridge, —SO$_2$NHCONH—, linking two aromatic or heteroaromatic rings, including by way of example and not limitation 2-(((((4,6-dimethoxypyrimidin-2-yl) aminocarbonyl))aminosulfonyl))-N,N-dimethyl-3-pyridinecarboxamide (generic name nicosulfuron); 3-[4,6-bis(difluoromethoxy)-pyrimidin-2-yl]-1-(2-methoxycarbonylphenylsulfonyl) urea (generic name primisulfuron); 2-[[[[(4,6-dimethyl-2-pyrimidinyl)amino]carbonyl]amino]sulfonyl]benzoic acid methyl ester (generic name sulfometuron methyl); methyl 2-[[[[(4-methoxy-6-methyl-1,3,5-triazin-2-yl)amino]carbonyl]amino]sulfonyl]benzoate (generic name metsulfuron methyl); methyl-2-[[[[N-(4-methoxy-6-methyl-1,3,5-triazin-2-yl)methylamino]carbonyl]amino]sulfonyl]benzoate (generic name tribenuron methyl); methyl-3-[[[[(4-methoxy-6-methyl-1,3,5-triazin-2-yl) amino]carbonyl]amino]sulfonyl]-2-thiophenecarboxylate (generic name thifensulfuron methyl); 2-chloro-N-[(4-methoxy-6-methyl-1,3,5-triazin-2-yl)aminocarbonyl]benzenesulfonamide (generic name chlorsulfuron); ethyl 2-[[[[(4-chloro-6-methoxypyrimidin-2-yl) amino]carbonyl]amino]sulfonyl]benzoate (generic name chlorimuron ethyl); methyl 2-[[[[N-(4-methoxy-6-methyl-1, 3,5-triazin-2-yl)methylamino]carbonyl]amino]sulfonyl] benzoate (generic name tribenuron methyl); 3-(6-methoxy-4-methyl-1,3,5-triazin-2-yl)-1-[2-(2-chloroethoxy)- phenylsulfonyl]-urea (generic name triasulfuron); and the other examples of sulfonylurea herbicides given in the specification.

As used in the specification and claims, unless otherwise clearly indicated by context, the term "plant" is intended to encompass plants at any stage of maturity, as well as any cells, tissues, or organs taken or derived from any such plant, including without limitation any embryos, seeds, leaves, stems, flowers, fruits, roots, tubers, single cells, gametes, another cultures, callus cultures, suspension cultures, other tissue cultures, or protoplasts. Also, unless otherwise clearly indicated by context, the term "plant" is intended to refer to a photosynthetic organism or green plant including algae, mosses, ferns, gymnosperms, and angiosperms. The term excludes, however, both prokaryotes, and eukaryotes that do not carry out photosynthesis such as yeast, other fungi, and the so-called red plants and brown plants that do not carry out photosynthesis.

Unless otherwise clearly indicated by context, the "genome" of a plant refers to the entire DNA sequence content of the plant, including nuclear chromosomes, mitochondrial chromosomes, chloroplast chromosomes, plasmids, and other extra-nuclear or extra-chromosomal DNA. If, for example, a herbicide resistance nucleotide sequence is incorporated into the cells of a transformed plant in a plasmid or other genetic element that might not otherwise be consistently maintained and inherited by the plant and its progeny, then the herbicide resistance trait itself may be used to apply selective pressure upon such plants to maintain the herbicide resistance phenotype and genotype. Such a plant is considered to have the herbicide resistance nucleotide sequence in its "genome" within the contemplation of this definition.

Unless otherwise clearly indicated by context, the "progeny" of a plant includes a plant of any subsequent generation whose ancestry can be traced to that plant.

Unless otherwise clearly indicated by context, a "derivative" of a herbicide-resistant plant includes both the progeny of that herbicide-resistant plant, as the term "progeny" is defined above; and also any mutant, recombinant, or genetically-engineered derivative of that plant, whether of the same species or of a different species; where, in either case, the herbicide-resistance characteristics of the original herbicide-resistant plant have been transferred to the derivative plant. Thus a "derivative" of a rice plant with a resistant AHAS enzyme would include, by way of example and not limitation, any of the following plants that express the same resistant AHAS enzyme: $F_1$ progeny rice plants, $F_2$ progeny rice plants, $F_{30}$ progeny rice plants, a transgenic corn plant transformed with a herbicide resistance nucleotide sequence from the resistant rice plant, and a transgenic sweet potato plant transformed with a herbicide resistance nucleotide sequence from the resistant rice plant.

The following definitions should be understood to apply throughout the specification and claims, unless otherwise clearly indicated by context.

An "isolated" nucleic acid sequence is an oligonucleotide sequence that is located outside a living cell. A cell comprising an "isolated" nucleic acid sequence is a cell that has been transformed with a nucleic acid sequence that at one time was located outside a living cell; or a cell that is the progeny of, or a derivative of, such a cell.

A "functional" or "normal" AHAS enzyme is one that is capable of catalyzing the first step in the pathway for synthesis of the essential amino acids isoleucine, leucine, and valine; regardless of whether the enzyme expresses herbicide resistance.

A "resistant" plant is one that produces a functional AHAS enzyme, and that is capable of reaching maturity when grown in the presence of normally inhibitory levels of a herbicide that normally inhibits AHAS. The term "resistant" or "resistance," as used herein, is also intended to encompass "tolerant" plants, i.e., those plants that phenotypically evidence adverse, but not lethal, reactions to one or more AHAS herbicides. A "resistant" AHAS enzyme is a functional AHAS enzyme that retains substantially greater activity than does a wild-type AHAS enzyme in the presence of normally inhibitory levels of an AHAS herbicide, as measured by in vitro assays of the respective enzymes' activities. A "wild-type" or "sensitive" plant is one that produces a functional AHAS enzyme, where the plant is sensitive to normally inhibitory levels of a herbicide that normally inhibits AHAS. A "resistant" plant is a plant that is resistant to normally inhibitory levels of a herbicide that normally inhibits AHAS (either due to a resistant AHAS enzyme or another mechanism of resistance in the plant). Note that within the contemplation of this last definition, "wild-type" plants include cultivated varieties; the designation "wild-type" refers to the presence or absence of normal levels of herbicide sensitivity, and in the context of this specification and the claims the term "wild-type" carries no connotation as to whether a particular plant is the product of cultivation and artificial selection, or is found in nature in an uncultivated state.

A "wild-type" AHAS enzyme or "wild-type" AHAS sequence is an AHAS enzyme or a DNA sequence encoding an AHAS enzyme, respectively, that does not impart herbicide resistance. Thus, within the scope of this definition, a "wild-type" AHAS may, for example, contain one or more mutations, provided that the mutations do not impart herbicide resistance. In some species, such as rice, as was seen for example in the varieties Kinmaze and Cypress, more than one wild-type AHAS may naturally exist in different varieties. A "wild-type" AHAS includes, for example, any of these multiple AHAS enzymes from different varieties. A "wild-type" AHAS also includes, for example, a hybrid of two or more of these wild-type AHAS enzymes. (A "hybrid" of different AHAS enzymes corresponds exactly to at least one of the "parent" enzymes at every amino acid in its sequence; for example, an AHAS that is identical to the Kinmaze AHAS at amino acids 1 through 300, and that is identical to the Cypress AHAS at amino acids 301 through the carboxy terminus.)

The complete disclosures of all references cited in this specification are hereby incorporated by reference, as are the complete disclosures of the present inventor's U.S. provisional patent application Ser. No. 60/107,255, filed 5 Nov. 1998; U.S. provisional patent application Ser. No. 60/163,765, filed 5 Nov. 1999; international patent application number PCT/US99/26062, filed 5 Nov. 1999; and U.S. provisional application Ser. No. 60/203,434, filed 10 May 2000. In the event of an otherwise irreconcilable conflict, however, the present specification shall control. In particular, the preliminary nucleotide sequence data contained in these prior applications is not incorporated to the extent that it is superseded by the sequence data contained in the present specification.

Notes on herbicide nomenclature—the following listing gives trade names, generic names, and chemical names for various herbicides: Pursuit™ or Newpath™ (imazethapyr: (±)-2-[4,5-dihydro-4-methyl-4-(1-methylethyl)-5-oxo-1H-imidazol-2-yl]-5-ethyl-3-pyridinecarboxylic acid); Scepter™ (imazaquin: 2-[4,5-dihydro-4-methyl-4-(1-methylethyl)-5-oxo-1H-imidazol-2-yl]-3-quinolinecarboxylic acid); Accent™ (nicosulfuron: 2-(((((4,6-dimethoxypyrimidin-2-yl) aminocarbonyl))aminosulfonyl))-N,N-dimethyl-3-pyridinecarboxamide); Beacon™ (primisulfuron: 3-[4,6-bis (difluoromethoxy)-pyrimidin-2-yl]-1-(2-methoxycarbonylphenylsulfonyl) urea); Raptor™ (imazamox: (+)-5-methoxymethyl-2-(4-isopropyl-4-methyl-5-oxo-2-imidazolin-2-yl) nicotinic acid; Cadre™ (imazapic: (±)-2-[4,5-dihydro-4-methyl-4-(1-methyl-ethyl)-5-oxo-1H-imidazol-2-yl]-5-methyl-3-pyridinecarboxylic acid; alternate chemical name (±)-2-(4-isopropyl-4-methyl-5-oxo-2-imidazolin-2-yl)-5-methylnicotinic acid); Arsenal™ (imazapyr: 2-[4,5-dihydro-4-methyl-4-(1-methylethyl)-5-oxo-1H-imidazol-2-yl]-3-pyridinecarboxylic acid); Oust™ (sulfometuron methyl: chemical name 2-[[[[(4,6-dimethyl-2-pyrimidinyl)amino]carbonyl]amino]sulfonyl]benzoic acid methyl ester); Ally™ (metsulfuron methyl: methyl 2-[[[[(4-methoxy-6-methyl-1,3,5-triazin-2-yl)amino]carbonyl] amino]sulfonyl]benzoate); Harmony™ (mixture of thifensulfuron methyl and tribenuron methyl: mixture of methyl-3-[[[[(4-methoxy-6-methyl-1,3,5-triazin-2-yl) amino] carbonyl]amino]sulfonyl]-2-thiophenecarboxylate and methyl-2-[[[[N-(4-methoxy-6-methyl-1,3,5-triazin-2-yl)methylamino]carbonyl]amino]sulfonyl]benzoate); Pinnacle™ (thifensulfuron methyl: methyl-3-[[[[(4-methoxy-6-methyl-1,3,5-triazin-2-yl) amino]carbonyl]amino]sulfonyl]-2-thiophenecarboxylate); Glean™ or Telar™ (chlorsulfuron: 2-chloro-N-[(4-methoxy-6-methyl-1,3,5-triazin-2-yl)aminocarbonyl]benzenesulfonamide); Classic™ (chlorimuron ethyl: ethyl 2-[[[[(4-chloro-6-methoxypyrimidin-2-yl) amino]carbonyl]amino]sulfonyl]benzoate); Express™ (tribenuron methyl: methyl 2-[[[[N-(4-methoxy-6-methyl-1, 3,5-triazin-2-yl)methylamino]carbonyl]amino]sulfonyl] benzoate); Assert™ (imazamethabenz methyl: m-toluic acid, 6-(4-isopropyl-4-methyl-5-oxo-2-imidazolin-2-yl)-, methyl ester; and p-toluic acid, 2-(4-isopropyl-4-methyl-5-oxo-2-imidazolin-2-yl)-, methyl ester); and Amber™ (triasulfuron: 3-(6-methoxy-4-methyl-1,3,5-triazin-2-yl)-1-[2-(2-chloroethoxy)-phenylsulfonyl]-urea); Staple™ (pyrithiobac sodium: sodium 2-chloro-6-[(4,6-dimethoxy pyrimidin-2-yl) thio]benzoate); and Matrix™ (rimsulfuron: N-((4,6-dimethoxypyrimidin-2-yl)aminocarbonyl)-3-(ethylsulfonyl)-2-pyridinesulfonamide).

Note on amino acid numbering convention used in the specification and claims: As used in the Claims, and as used in the specification unless context clearly indicates otherwise, the amino acids of rice AHAS are numbered as corresponding to the numbering shown for the wild-type (Cypress) AHAS sequence (SEQ ID NO 17), or the corresponding position in other AHAS coding sequences where variations exist (such as were seen here for the variety Kinmaze). In particular, amino acid position 627 is the amino acid corresponding to amino acid 627 in SEQ ID NO 17, which is the serine residue near the carboxy terminus in the wild type rice AHAS. Nucleotide positions are generally indicated indirectly, by reference to the number of the amino acid encoded by a particular codon. For example, the codon in the wild-type (Cypress) AHAS coding sequence that corresponds to amino acid 627 is the AGT codon appearing in SEQ ID NO 14 at nucleotides 1879-1881. By contrast, in the wild-type (Kinmaze) sequence of SEQ ID NO 2, this codon appears at nucleotides 1926-1928. Amino acid positions and corresponding nucleotide positions for other species are determined by homology—for example, the amino acid or codon that is in the position that is homologous to amino acid 627 (wild type serine) in rice, or to the corresponding codon. Such homology may be determined through software commonly used in the art, such as GAP, PILEUP, or BLAST.

What is claimed:

1. An isolated, recombinant, mutagenized, or synthetic polynucleotide encoding an acetohydroxyacid synthase (AHAS) polypeptide, wherein the sequence of the encoded AHAS polypeptide has about 95% or greater sequence identity with SEQ ID NO:25, wherein the encoded AHAS polypeptide has a glutamic acid at the position equivalent to amino acid position 628 of SEQ ID NO:25, and wherein said polynucleotide is operatively linked to a heterologous promoter.

2. The polynucleotide of claim 1, wherein the sequence of said polynucleotide has about 95% or greater sequence identity with SEQ ID NO:24.

3. A transformation vector comprising the polynucleotide of claim 1.

4. A host cell comprising the polynucleotide of claim 1.

5. A method for producing a plant having tolerance to a herbicide, said method comprising transforming plant cells with the polynucleotide of claim 1, wherein the plants cells are capable of regenerating a plant.

6. A plant produced by the method of claim 5, wherein cells of said plant express the encoded AHAS polypeptide.

7. A derivative plant of the plant of claim 6, wherein cells of said derivative plant express the encoded AHAS polypeptide.

8. A seed of the plant of claim 6, or a seed capable of producing said plant, wherein cells of said seed comprise said polynucleotide.

9. A seed of the derivative plant of claim 7, or a seed capable of producing said derivative plant, wherein cells of said seed comprise said polynucleotide.

10. A plant product prepared from the plant of claim 6, wherein said plant product comprises said polynucleotide.

11. A plant product prepared from the derivative plant of claim 7, wherein said plant product comprises said polynucleotide.

12. A method for producing a herbicide-tolerant plant, said method comprising crossing or back-crossing the plant of claim 6 with other germplasm to produce a progeny plant, wherein cells of said progeny plant express the encoded AHAS polypeptide.

13. A plant produced by the method of claim 12, wherein cells of said herbicide-tolerant plant express the encoded AHAS polypeptide.

14. A derivative plant prepared from the plant of claim 13, wherein cells of said derivative plant express the encoded AHAS polypeptide.

15. A seed of the plant of claim 13, or a seed capable of producing said plant, wherein cells of said seed comprise said polynucleotide.

16. A seed of the derivative plant of claim 14, or a seed capable of producing said derivative plant, wherein cells of said seed comprise said polynucleotide.

17. A plant product prepared from the plant of claim 13, wherein said plant product comprises said polynucleotide.

18. A plant product prepared from the derivative plant of claim 14, wherein said plant product comprises said polynucleotide.

19. A method for controlling weeds in the vicinity of the plant of claim 6, said method comprising applying a herbicide in the vicinity of the plant, at a level of the herbicide that would normally inhibit the growth of a wild-type plant of the same species, wherein the herbicide normally inhibits acetohydroxyacid synthase.

20. The method of claim 19, wherein said applying step comprises applying the herbicide at a pre-emergence stage, a post-emergence stage, or both.

21. The method of claim 19, wherein the herbicide comprises a herbicidally effective imidazolinone.

22. The method of claim 19, wherein the herbicide comprises a herbicidally effective sulfonylurea.

23. The method of claim 19, wherein the herbicide is selected from the group consisting of imazethapyr, imazapic, imazapyr, imazamox, and imazaquin.

24. An isolated, recombinant, mutagenized, or synthetic acetohydroxyacid synthase (AHAS) polypeptide, wherein the sequence of said polypeptide is SEQ ID NO:19 or SEQ ID NO:25.

25. The polynucleotide of claim 1, wherein the sequence of said polynucleotide comprises SEQ ID NO:24.

26. A host rice cell comprising the polynucleotide of claim 1.

27. A method for producing a rice plant having tolerance to a herbicide, said method comprising transforming rice cells with the polynucleotide of claim 1, wherein the rice cells are capable of regenerating a rice plant.

28. A rice plant produced by the method of claim 27, wherein cells of said rice plant express the encoded AHAS polypeptide.

29. A derivative rice plant of the plant of claim 28, wherein cells of said derivative rice plant express the encoded AHAS polypeptide.

30. A seed of the rice plant of claim 28, or a seed capable of producing said rice plant, wherein cells of said seed comprise said polynucleotide.

31. A seed of the derivative rice plant of claim 29, or a seed capable of producing said derivative rice plant, wherein cells of said seed comprise said polynucleotide.

32. A plant product prepared from the rice plant of claim 28, wherein said plant product comprises said polynucleotide.

33. A plant product prepared from the derivative rice plant of claim 29, wherein said plant product comprises said polynucleotide.

34. A method for producing a herbicide-tolerant rice plant, said method comprising crossing or back-crossing the rice plant of claim 28 with other germplasm to produce a progeny rice plant, wherein cells of said progeny rice plant express the encoded AHAS polypeptide.

35. A herbicide-tolerant rice plant produced by the method of claim 34, wherein cells of said herbicide-tolerant rice plant express the encoded AHAS polypeptide.

36. A derivative rice plant prepared from the rice plant of claim 35, wherein cells of said derivative rice plant express the encoded AHAS polypeptide.

37. A seed of the rice plant of claim 35, or a seed capable of producing said rice plant, wherein cells of said seed comprise said polynucleotide.

38. A seed of the derivative rice plant of claim 36, or a seed capable of producing said derivative rice plant, wherein cells of said seed comprise said polynucleotide.

39. A plant product prepared from the rice plant of claim 35, wherein said plant product comprises said polynucleotide.

40. A plant product prepared from the derivative rice plant of claim 36, wherein said plant product comprises said polynucleotide.

41. A method for controlling weeds in the vicinity of the plant of claim 28, said method comprising applying a herbicide in the vicinity of the plant, at a level of the herbicide that would normally inhibit the growth of a wild-type plant of the same species, wherein the herbicide normally inhibits acetohydroxyacid synthase.

42. The method of claim 41, wherein said applying step comprises applying the herbicide at a pre-emergence stage, a post-emergence stage, or both.

43. The method of claim 41, wherein the herbicide comprises a herbicidally effective imidazolinone.

44. The method of claim 41, wherein the herbicide comprises a herbicidally effective sulfonylurea.

45. The method of claim 41, wherein the herbicide is selected from the group consisting of imazethapyr, imazapic, imazapyr, imazamox, and imazaquin.

46. A rice plant, wherein the cells of said rice plant comprise the polynucleotide of claim 1.

47. A derivative rice plant of the plant of claim 46, wherein the cells of said derivative rice plant comprise said polynucleotide.

48. A seed of the rice plant of claim 46, or a seed capable of producing said rice plant, wherein cells of said seed comprise said polynucleotide.

49. A seed of the derivative rice plant of claim 47, or a seed capable of producing said derivative rice plant, wherein cells of said seed comprise said polynucleotide.

50. A plant product prepared from the rice plant of claim 46, wherein said plant product comprises said polynucleotide.

51. A plant product prepared from the derivative rice plant of claim 47, wherein said plant product comprises said polynucleotide.

52. A method for producing a herbicide-tolerant rice plant, said method comprising crossing or back-crossing the rice plant of claim 46 with other germplasm to produce a progeny rice plant, wherein cells of said progeny rice plant express the encoded AHAS polypeptide.

53. A herbicide-tolerant rice plant produced by the method of claim 52, wherein cells of said herbicide-tolerant rice plant express the encoded AHAS polypeptide.

54. A derivative rice plant prepared from the rice plant of claim 53, wherein cells of said derivative rice plant express the encoded AHAS polypeptide.

55. A seed of the rice plant of claim 53, or a seed capable of producing said rice plant, wherein cells of said seed comprise said polynucleotide.

56. A seed of the derivative rice plant of claim 54, or a seed capable of producing said derivative rice plant, wherein cells of said seed comprise said polynucleotide.

57. A plant product prepared from the rice plant of claim 53, wherein said plant product comprises said polynucleotide.

58. A plant product prepared from the derivative rice plant of claim 54, wherein said plant product comprises said polynucleotide.

59. A method for controlling weeds in the vicinity of the plant of claim 46, said method comprising applying a herbicide in the vicinity of the plant, at a level of the herbicide that would normally inhibit the growth of a wild-type plant of the same species, wherein the herbicide normally inhibits acetohydroxyacid synthase.

60. The method of claim 59, wherein said applying step comprises applying the herbicide at a pre-emergence stage, a post-emergence stage, or both.

61. The method of claim 59, wherein the herbicide comprises a herbicidally effective imidazolinone.

62. The method of claim 59, wherein the herbicide comprises a herbicidally effective sulfonylurea.

63. The method of claim 59, wherein the herbicide is selected from the group consisting of imazethapyr, imazapic, imazapyr, imazamox, and imazaquin.

64. A rice plant, wherein the cells of said rice plant comprise the polynucleotide of claim 25.

65. A rice plant, wherein the cells of said rice plant comprise the polynucleotide of claim 1.

66. The polypeptide of claim 24, wherein the sequence of said polypeptide is SEQ ID NO:19.

67. The polypeptide of claim 24, wherein the sequence of said polypeptide is SEQ ID NO:25.

* * * * *

UNITED STATES PATENT AND TRADEMARK OFFICE
CERTIFICATE OF CORRECTION

PATENT NO. : 9,090,904 B2
APPLICATION NO. : 12/166517
DATED : July 28, 2015
INVENTOR(S) : Timothy P. Croughan It is certified that error appears in the above-identified patent and that said Letters Patent is hereby corrected as shown below:

Title Page

Page 1, Item (56) under the heading "OTHER PUBLICATIONS," first column, fifth entry, in the Goulart et al. (2012) citation, "filed" should read –field–

Page 2, Item (56) under the heading "OTHER PUBLICATIONS," first column, fourth entry, in the Croughan et al. (Dec. 1999) citation, "Imidazolidone" should read –Imidazolinone–

Page 2, Item (56) under the heading "OTHER PUBLICATIONS," first column, fifth entry, in the Croughan et al. (Sept. 1996) citation, "Imidazolidone" should read –Imidazolinone–

Page 2, Item (56) under the heading "OTHER PUBLICATIONS," first column, fifteenth entry, in the Croughan CRIS Report No. 0150120 citation, "Acession" should read –Accession–

In the Specification

Column 5, line 44, delete second occurrence of "the"

Column 7, line 34, after "AHAS" insert a --.--

Column 7, line 36, after "vivo" insert a --,--

Column 9, line 49, after "amino" insert --acid--

Column 23, line 32, "another" should read –anther–

Columns 29 and 30, Table 7, in the row "Imazapic (Cadre)" and column "ATCC PTA-902 CMC29," the entry that reads "10X" should read –5X–

Signed and Sealed this
Twenty-first Day of June, 2016

Michelle K. Lee
*Director of the United States Patent and Trademark Office*

Columns 29 and 30, Table 7, Note (2), second line, "aproppriate" should read –appropriate–

Column 33, in each of lines 14 and 16, "manufacture's" should read –manufacturer's–

Column 35, line 35, "(ATCCPTA-907)" should read –(ATCC PTA-907)–

Column 38, line 46, "identity" should read –identify–

Column 44, line 25, "another" should read –anther–

Column 45, line 2, "another" should read –anther–

Column 45, line 6, "seconducive" should read –se conducive–

Column 46, line 10, "another" should read –anther–

SEQUENCE LISTING

<160> NUMBER OF SEQ ID NOS: 25

<210> SEQ ID NO 1
<211> LENGTH: 1095
<212> TYPE: DNA
<213> ORGANISM: Oryza sativa
<220> FEATURE:
<221> NAME/KEY: misc_feature
<223> OTHER INFORMATION: Partial AHAS sequence, line CMC31

<400> SEQUENCE: 1

```
ggcacggcgc ccgattctct atgtcggtgg tggctgctct gcatctggtg atgaattgcg      60
ccggtttgtt gagctgaccg gcatcccagt tacaaccact ctgatgggcc tcggcaattt     120
ccccagtgat gatccgttgt ccctgcgcat gcttgggatg catggcacgg tgtacgcaaa     180
ttatgcggtg gataaggctg acctgttgct tgcatttggc gtgcggtttg atgatcgtgt     240
gacagggaaa attgaggctt ttgcaagcag ggccaagatt gtgcacattg acattgatcc     300
agcggagatt ggaaagaaca agcaaccaca tgtgtcaatt tgcgcagatg ttaagcttgc     360
tttacagggc ttgaatgctc tgctagacca gagcacaaca aagacaagtt ctgattttag     420
tgcatggcac aatgagttgg accagcagaa gagggagttt cctctggggt acaagacttt     480
tggtgaagag atcccaccgc aatatgctat tcaggtgctg gatgagctga cgaaagggga     540
ggcaatcatc gctactggtg ttggacagca ccagatgtgg gcggcacaat attaccccta     600
caagcggcca cggcagtggc tgtcttcggc tggtctgggc gcaatgggat ttgggctgcc     660
tgctgcagct ggtgcttctg tggctaaccc aggtgtcaca gttgttgata ttgatgggga     720
tggtagcttc ctcatgaaca ttcaggagtt ggcattgatc cgcattgaga acctcccggt     780
gaaggtgatg gtgttgaaca accaacattt gggtatggtt gtgcaatggg aggataggtt     840
ttacaaggca aatagggcgc atacatactt gggcaaccca gaatgtgaga gcagatatta     900
tccagatttt gtgactattg ctaaagggtt caatattcct gcagtccgtg taacaaagaa     960
gagtgaagtc cgtgccgcca tcaagaagat gctcgagacc ccagggccat acttgttgga    1020
tatcatcgtc ccacaccagg agcatgtgct gcctatgatc ccaaggggg cgcattcaag    1080
gacatgatct ggagg                                                      1095
```

<210> SEQ ID NO 2
<211> LENGTH: 2301
<212> TYPE: DNA
<213> ORGANISM: Oryza sativa
<220> FEATURE:
<221> NAME/KEY: misc_feature
<223> OTHER INFORMATION: Wild type AHAS sequence, variety Kinmaze
<300> PUBLICATION INFORMATION:
<308> DATABASE ACCESSION NUMBER: BLAST / AB049822
<309> DATABASE ENTRY DATE: 2000-04-14

<400> SEQUENCE: 2

```
cccaaaccca gaaaccctcg ccgccgccgc cgccgccacc acccaccatg gctacgaccg      60
ccgcggccgc ggccgccgcc ctgtccgccg ccgcgacggc caagaccggc cgtaagaacc     120
accagcgaca ccacgtcctt cccgctcgag gccgggtggg ggcggcggcg gtcaggtgct     180
cggcggtgtc cccggtcacc ccgccgtccc cggccgcc ggcacgccg ctccggccgt     240
gggggccggc cgagccccgc aagggcgcgg acatcctcgt ggaggcgctg gagcggtgcg     300
gcgtcagcga cgtgttcgcc tacccgggcg gcgcgtccat ggagatccac caggcgctga     360
cgcgctcccc ggtcatcacc aaccacctct ccgccacga gcagggcgag gcgttcgcgg     420
```

| | |
|---|---|
| cgtccgggta cgcgcgcgcg tccggccgcg tcggggtctg cgtcgccacc tccggccccg | 480 |
| gggcaaccaa cctcgtgtcc gcgctcgccg acgcgctgct cgactccgtc ccgatggtcg | 540 |
| ccatcacggg ccaggtcccc cgccgcatga tcggcaccga cgccttccag gagacgccca | 600 |
| tagtcgaggt cacccgctcc atcaccaagc acaattacct tgtccttgat gtggaggaca | 660 |
| tcccccgcgt catacaggaa gccttcttcc tcgcgtcctc gggccgtcct ggcccggtgc | 720 |
| tggtcgacat ccccaaggac atccagcagc agatggccgt gccggtctgg gacacctcga | 780 |
| tgaatctacc agggtacatc gcacgcctgc ccaagccacc cgcgacagaa ttgcttgagc | 840 |
| aggtcttgcg tctggttggc gagtcacggc gcccgattct ctatgtcggt ggtggctgct | 900 |
| ctgcatctgg tgacgaattg cgctggtttg ttgagctgac tggtatccca gttacaacca | 960 |
| ctctgatggg cctcggcaat ttccccagtg acgacccgtt gtccctgcgc atgcttggga | 1020 |
| tgcatggcac ggtgtacgca aattatgccg tggataaggc tgacctgttg cttgcgtttg | 1080 |
| gtgtgcggtt tgatgatcgt gtgacaggga aaattgaggc ttttgcaagc agggccaaga | 1140 |
| ttgtgcacat tgacattgat ccagcagaga ttggaaagaa caagcaacca catgtgtcaa | 1200 |
| tttgcgcaga tgttaagctt gctttacagg cttgaatgc tctgctacaa cagagcacaa | 1260 |
| caaagacaag ttctgatttt agtgcatggc acaatgagtt ggaccagcag aagagggagt | 1320 |
| ttcctctggg gtacaaaact tttggtgaag agatcccacc gcaatatgcc attcaggtgc | 1380 |
| tggatgagct gacgaaaggt gaggcaatca tcgctactgg tgttgggcag caccagatgt | 1440 |
| gggcggcaca atattacacc tacaagcggc cacggcagtg gctgtcttcg gctggtctgg | 1500 |
| gcgcaatggg atttgggctg cctgctgcag ctggtgcttc tgtggctaac ccaggtgtca | 1560 |
| cagttgttga tattgatggg gatggtagct tcctcatgaa cattcaggag ctggcattga | 1620 |
| tccgcattga gaacctccct gtgaaggtga tggtgttgaa caaccaacat ttgggtatgg | 1680 |
| tggtgcaatg ggaggatagg ttttacaagg cgaatagggc gcatacatac ttgggcaacc | 1740 |
| cggaatgtga gagcgagata tatccagatt ttgtgactat tgctaagggg ttcaatattc | 1800 |
| ctgcagtccg tgtaacaaag aagagtgaag tccgtgccgc catcaagaag atgctcgaga | 1860 |
| ctccagggcc atacttgttg gatatcatcg tcccgcacca ggagcatgtg ctgcctatga | 1920 |
| tcccaagtgg gggcgcattc aaggacatga tcctggatgg tgatggcagg actgtgtatt | 1980 |
| aatctataat ctgtatgttg gcaaagcacc agcccggcct atgtttgacc tgaatgaccc | 2040 |
| ataaagagtg gtatgcctat gatgtttgta tgtgctctat caataactaa ggtgtcaact | 2100 |
| atgaaccata tgctcttctg ttttacttgt ttgatgtgct tggcatggta atcctaatta | 2160 |
| gcttcctgct gtctaggttt gtagtgtgtt gttttctgta ggcatatgca tcacaagata | 2220 |
| tcatgtaagt ttcttgtcct acatatcaat aataagagaa taaagtactt ctatgcaaaa | 2280 |
| aaaaaaaaaa aaaaaaaaa a | 2301 |

```
<210> SEQ ID NO 3
<211> LENGTH: 644
<212> TYPE: PRT
<213> ORGANISM: Oryza sativa
<220> FEATURE:
<221> NAME/KEY: misc_feature
<223> OTHER INFORMATION: Wild type AHAS sequence, variety Kinmaze
<300> PUBLICATION INFORMATION:
<308> DATABASE ACCESSION NUMBER: BLAST / AB049822
<309> DATABASE ENTRY DATE: 2000-04-14

<400> SEQUENCE: 3
```

Met Ala Thr Thr Ala Ala Ala Ala Ala Ala Ala Leu Ser Ala Ala Ala

```
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
            35                  40                  45

Pro Val Thr Pro Pro Ser Pro Ala Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
            130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
            195                 200                 205

Ile Gln Glu Ala Phe Phe Leu Ala Ser Ser Gly Arg Pro Gly Pro Val
210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
            245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
            275                 280                 285

Asp Glu Leu Arg Trp Phe Val Glu Leu Thr Gly Ile Pro Val Thr Thr
            290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
            325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
            370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
            405                 410                 415

Glu Leu Asp Gln Gln Lys Arg Glu Phe Pro Leu Gly Tyr Lys Thr Phe
            420                 425                 430
```

```
Gly Glu Glu Ile Pro Pro Gln Tyr Ala Ile Gln Val Leu Asp Glu Leu
        435                 440                 445
Thr Lys Gly Glu Ala Ile Ile Ala Thr Gly Val Gly Gln His Gln Met
450                 455                 460
Trp Ala Ala Gln Tyr Tyr Thr Tyr Lys Arg Pro Arg Gln Trp Leu Ser
465                 470                 475                 480
Ser Ala Gly Leu Gly Ala Met Gly Phe Gly Leu Pro Ala Ala Ala Gly
        485                 490                 495
Ala Ser Val Ala Asn Pro Gly Val Thr Val Val Asp Ile Asp Gly Asp
        500                 505                 510
Gly Ser Phe Leu Met Asn Ile Gln Glu Leu Ala Leu Ile Arg Ile Glu
        515                 520                 525
Asn Leu Pro Val Lys Val Met Val Leu Asn Asn Gln His Leu Gly Met
        530                 535                 540
Val Val Gln Trp Glu Asp Arg Phe Tyr Lys Ala Asn Arg Ala His Thr
545                 550                 555                 560
Tyr Leu Gly Asn Pro Glu Cys Glu Ser Glu Ile Tyr Pro Asp Phe Val
        565                 570                 575
Thr Ile Ala Lys Gly Phe Asn Ile Pro Ala Val Arg Val Thr Lys Lys
        580                 585                 590
Ser Glu Val Arg Ala Ala Ile Lys Lys Met Leu Glu Thr Pro Gly Pro
        595                 600                 605
Tyr Leu Leu Asp Ile Ile Val Pro His Gln Glu His Val Leu Pro Met
        610                 615                 620
Ile Pro Ser Gly Gly Ala Phe Lys Asp Met Ile Leu Asp Gly Asp Gly
625                 630                 635                 640
Arg Thr Val Tyr

<210> SEQ ID NO 4
<211> LENGTH: 2279
<212> TYPE: DNA
<213> ORGANISM: Oryza sativa
<220> FEATURE:
<221> NAME/KEY: misc_feature
<223> OTHER INFORMATION: Herbicide resistant AHAS sequence, variety
      Kinmaze
<300> PUBLICATION INFORMATION:
<308> DATABASE ACCESSION NUMBER: BLAST / AB049823
<309> DATABASE ENTRY DATE: 2001-04-14

<400> SEQUENCE: 4
ctcgccgccg ccgccgccgc caccacccac catggctacg accgccgcgg ccgcggccgc      60
cgccctgtcc gccgccgcga cggccaagac cggccgtaag aaccaccagc gacaccacgt     120
ccttcccgct cgaggccggg tggggcggc ggcggtcagg tgctcggcgg tgtcccggt      180 caccccgccg tccccggcgc cgccggccac gccgctccgg ccgtgggggc cggccgagcc     240
ccgcaagggc gcggacatcc tcgtggaggc gctggagcgg tgcggcgtca gcgacgtgtt     300
cgcctacccg ggcggcgcgt ccatggagat ccaccaggcg ctgacgcgct ccccggtcat     360
caccaaccac ctcttccgcc acgagcaggg cgaggcgttc gcggcgtccg ggtacgcgcg     420
cgcgtccggc gcgtcggggg tctgcgtcgc cacctccggc cccgggggcaa ccaacctcgt     480 gtccgcgctc gccgacgcgc tgctcgactc cgtcccgatg gtcgccatca cgggccaggt     540 cccccgccg atgatcggca ccgacgccct ccaggagacg cccatagtcg aggtcacccg     600
ctccatcacc aagcacaatt accttgtcct tgatgtggag gacatccccc gcgtcataca     660
```

```
ggaagccttc ttcctcgcgt cctcgggccg tcctggcccg gtgctggtcg acatccccaa    720
ggacatccag cagcagatgg ccgtgccggt ctgggacacc tcgatgaatc taccagggta    780
catcgcacgc ctgcccaagc cacccgcgac agaattgctt gagcaggtct tgcgtctggt    840
tggcgagtca cggcgcccga ttctctatgt cggtggtggc tgctctgcat ctggtgacga    900
attgcgctgg tttgttgagc tgactggtat cccagttaca accactctga tgggcctcgg    960
caatttcccc agtgacgacc cgttgtccct gcgcatgctt gggatgcatg gcacggtgta   1020
cgcaaattat gccgtggata aggctgacct gttgcttgcg tttggtgtgc ggtttgatga   1080
tcgtgtgaca gggaaaattg aggcttttgc aagcagggcc aagattgtgc acattgacat   1140
tgatccagca gagattggaa agaacaagca accacatgtg tcaatttgcg cagatgttaa   1200
gcttgcttta cagggcttga atgctctgct acaacagagc acaacaaaga caagttctga   1260
ttttagtgca tggcacaatg agttggacca gcagaagagg gagtttcctc tggggtacaa   1320
aactttggt gaagagatcc caccgcaata tgccattcag gtgctggatg agctgacgaa   1380
aggtgaggca atcatcgcta ctggtgttgg gcagcaccag atgtgggcgg cacaatatta   1440
cacctacaag cggccacggc agtggctgtc ttcggctggt ctgggcgcaa tgggatttgg   1500
gctgcctgct gcagctggtg cttctgtggc taacccaggt gtcacagttg ttgatattga   1560
tggggatggt agcttcctca tgaacattca ggagctggca ttgatccgca ttgagaacct   1620
ccctgtgaag gtgatggtgt tgaacaacca acatttgggt atggtggtgc aattggagga   1680
taggttttac aaggcgaata gggcgcatac atacttgggc aacccggaat gtgagagcga   1740
gatatatcca gattttgtga ctattgctaa ggggttcaat attcctgcag tccgtgtaac   1800
aaagaagagt gaagtccgtg ccgccatcaa gaagatgctc gagactccag gccatactt    1860
gttggatatc atcgtcccgc accaggagca tgtgctgcct atgatcccaa ttgggggcgc    1920
attcaaggac atgatcctgg atggtgatgg caggactgtg tattaatcta taatctgtat   1980
gttggcaaag caccagcccg gcctatgttt gacctgaatg acccataaag agtggtatgc   2040
ctatgatgtt tgtatgtgct ctatcaataa ctaaggtgtc aactatgaac catatgctct   2100
tctgttttac ttgtttgatg tgcttggcat ggtaatccta attagcttcc tgctgtctag   2160
gtttgtagtg tgttgttttc tgtaggcata tgcatcacaa gatatcatgt aagtttcttg   2220
tcctacatat caataataag agaataaagt acttctatgt aaaaaaaaaa aaaaaaaa    2279
```

<210> SEQ ID NO 5
<211> LENGTH: 644
<212> TYPE: PRT
<213> ORGANISM: Oryza sativa
<220> FEATURE:
<221> NAME/KEY: misc_feature
<223> OTHER INFORMATION: Herbicide resistant AHAS sequence, variety
      Kinmaze
<300> PUBLICATION INFORMATION:
<308> DATABASE ACCESSION NUMBER: BLAST / AB049823
<309> DATABASE ENTRY DATE: 2001-04-14

<400> SEQUENCE: 5

Met Ala Thr Thr Ala Ala Ala Ala Ala Ala Leu Ser Ala Ala
1               5                   10                  15

Thr Ala Lys Thr Gly Arg Lys Asn His Gln Arg His Val Leu Pro
            20                  25                  30

Ala Arg Gly Arg Val Gly Ala Ala Ala Val Arg Cys Ser Ala Val Ser
        35                  40                  45

Pro Val Thr Pro Pro Ser Pro Ala Pro Pro Ala Thr Pro Leu Arg Pro

-continued

```
                50                  55                  60
Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
                100                 105                 110

His Leu Phe Arg His Glu Gln Gly Ala Phe Ala Ala Ser Gly Tyr
                115                 120                 125

Ala Arg Ala Ser Gly Arg Val Gly Val Cys Val Ala Thr Ser Gly Pro
130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
                180                 185                 190

Thr Lys His Asn Tyr Leu Val Leu Asp Val Glu Asp Ile Pro Arg Val
                195                 200                 205

Ile Gln Glu Ala Phe Phe Leu Ala Ser Ser Gly Arg Pro Gly Pro Val
210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
                260                 265                 270

Ser Arg Arg Pro Ile Leu Tyr Val Gly Gly Gly Cys Ser Ala Ser Gly
                275                 280                 285

Asp Glu Leu Arg Trp Phe Val Glu Leu Thr Gly Ile Pro Val Thr Thr
                290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
                340                 345                 350

Thr Gly Lys Ile Glu Ala Phe Ala Ser Arg Ala Lys Ile Val His Ile
                355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
                420                 425                 430

Gly Glu Glu Ile Pro Pro Gln Tyr Ala Ile Gln Val Leu Asp Glu Leu
                435                 440                 445

Thr Lys Gly Glu Ala Ile Ile Ala Thr Gly Val Gly Gln His Gln Met
                450                 455                 460

Trp Ala Ala Gln Tyr Tyr Thr Tyr Lys Arg Pro Arg Gln Trp Leu Ser
465                 470                 475                 480
```

```
Ser Ala Gly Leu Gly Ala Met Gly Phe Gly Leu Pro Ala Ala Ala Gly
            485                 490                 495
Ala Ser Val Ala Asn Pro Gly Val Thr Val Val Asp Ile Asp Gly Asp
        500                 505                 510
Gly Ser Phe Leu Met Asn Ile Gln Glu Leu Ala Leu Ile Arg Ile Glu
    515                 520                 525
Asn Leu Pro Val Lys Val Met Val Leu Asn Asn Gln His Leu Gly Met
530                 535                 540
Val Val Gln Leu Glu Asp Arg Phe Tyr Lys Ala Asn Arg Ala His Thr
545                 550                 555                 560
Tyr Leu Gly Asn Pro Glu Cys Glu Ser Glu Ile Tyr Pro Asp Phe Val
                565                 570                 575
Thr Ile Ala Lys Gly Phe Asn Ile Pro Ala Val Arg Val Thr Lys Lys
            580                 585                 590
Ser Glu Val Arg Ala Ala Ile Lys Lys Met Leu Glu Thr Pro Gly Pro
        595                 600                 605
Tyr Leu Leu Asp Ile Ile Val Pro His Gln Glu His Val Leu Pro Met
    610                 615                 620
Ile Pro Ile Gly Gly Ala Phe Lys Asp Met Ile Leu Asp Gly Asp Gly
625                 630                 635                 640
Arg Thr Val Tyr

<210> SEQ ID NO 6
<211> LENGTH: 18
<212> TYPE: DNA
<213> ORGANISM: Artificial sequence
<220> FEATURE:
<221> NAME/KEY: misc_feature
<223> OTHER INFORMATION: HvAls 3 primer

<400> SEQUENCE: 6
tggcgaggca cggcgccc                                                18

<210> SEQ ID NO 7
<211> LENGTH: 18
<212> TYPE: DNA
<213> ORGANISM: Artificial Sequence
<220> FEATURE:
<221> NAME/KEY: misc_feature
<223> OTHER INFORMATION: HvAls 4 primer

<400> SEQUENCE: 7
gacgtggccg cttgtaag                                                18

<210> SEQ ID NO 8
<211> LENGTH: 18
<212> TYPE: DNA
<213> ORGANISM: Artificial Sequence
<220> FEATURE:
<221> NAME/KEY: misc_feature
<223> OTHER INFORMATION: HvAls 6 primer

<400> SEQUENCE: 8
agtacgaggt cctgccat                                                18

<210> SEQ ID NO 9
<211> LENGTH: 208
<212> TYPE: DNA
<213> ORGANISM: Oryza sativa
<220> FEATURE:
<221> NAME/KEY: misc_feature
```

<223> OTHER INFORMATION: Partial AHAS sequence, line PWC16

<400> SEQUENCE: 9

| | | |
|---|---|---|
| gtgagagcga gatatatcca gattttgtga ctattgctaa agggttcaat attcctgcag | 60 |
| tccgtgtaac aaagaagagt gaagtccgtg ccgccatcaa gaagatgctc gagaccccag | 120 |
| ggccatactt gttggatatc atcgtcccac accaggagca tgtgctgcct atgatcccaa | 180 |
| atgggggcgc attcaaggac atgatcct | 208 |

<210> SEQ ID NO 10
<211> LENGTH: 182
<212> TYPE: DNA
<213> ORGANISM: Oryza sativa
<220> FEATURE:
<221> NAME/KEY: misc_feature
<223> OTHER INFORMATION: Partial AHAS sequence, line PWC23

<400> SEQUENCE: 10

| | | |
|---|---|---|
| gtgactattg ctaaagggtt caatattcct gcagtccgtg taacaaagaa gagtgaagtc | 60 |
| cgtgccgcca tcaagaagat gctcgagacc ccagggccat acttgttgga tatcatcgtc | 120 |
| ccacaccagg agcatgtgct gcctatgatc ccaaatgggg gcgcattcaa ggacatgatc | 180 |
| ct | 182 |

<210> SEQ ID NO 11
<211> LENGTH: 208
<212> TYPE: DNA
<213> ORGANISM: Oryza sativa
<220> FEATURE:
<221> NAME/KEY: misc_feature
<223> OTHER INFORMATION: Partial AHAS sequence, line CMC29

<400> SEQUENCE: 11

| | | |
|---|---|---|
| gtgagagcga gatatatcca gattttgtga ctattgctaa agggttcaat attcctgcag | 60 |
| tccgtgtaac aaagaagagt gaagtccgtg ccgccatcaa gaagatgctc gagaccccag | 120 |
| ggccatactt gttggatatc atcgtcccac accaggagca tgtgctgcct atgatcccaa | 180 |
| atgggggcgc attcaaggac atgatcct | 208 |

<210> SEQ ID NO 12
<211> LENGTH: 182
<212> TYPE: DNA
<213> ORGANISM: Oryza sativa
<220> FEATURE:
<221> NAME/KEY: misc_feature
<223> OTHER INFORMATION: Partial AHAS sequence, line WDC33

<400> SEQUENCE: 12

| | | |
|---|---|---|
| gtgactattg ctaaagggtt caatattcct gcagtccgtg taacaaagaa gagtgaagtc | 60 |
| cgtgccgcca tcaagaagat gctcgagacc ccagggccat acttgttgga tatcatcgtc | 120 |
| ccacaccagg agcatgtgct gcctatgatc ccaaatgggg gcgcattcaa ggacatgatc | 180 |
| ct | 182 |

<210> SEQ ID NO 13
<211> LENGTH: 188
<212> TYPE: DNA
<213> ORGANISM: Oryza sativa
<220> FEATURE:
<221> NAME/KEY: misc_feature
<223> OTHER INFORMATION: Partial AHAS sequence, line WDC38

<400> SEQUENCE: 13

```
gattttgtga ctattgctaa agggttcaat attcctgcag tccgtgtaac aaagaagagt      60
gaagtccgtg ccgccatcaa gaagatgctc gagaccccag gcccatactt gttggatatc     120
atcgtcccac accaggagca tgtgctgcct atgatcccaa atggggggcgc attcaaggac     180 atgatcct                                                              188

<210> SEQ ID NO 14
<211> LENGTH: 1986
<212> TYPE: DNA
<213> ORGANISM: Oryza sativa
<220> FEATURE:
<221> NAME/KEY: misc_feature
<223> OTHER INFORMATION: Complete AHAS sequence, wild type, cultivar
      Cypress

<400> SEQUENCE: 14
atggctacga ccgccgcggc cgcggccgcc accttgtccg ccgccgcgac ggccaagacc      60
ggccgtaaga ccaccagcg acaccacgtc cttcccgctc gaggccgggt ggggggcggcg     120 gcggtcaggt gctcggcggt gtccccggtc accccgccgt ccccggcgcc gccggccacg     180
ccgctccggc cgtgggggcc ggccgagccc cgcaagggcg cggacatcct cgtggaggcg     240
ctggagcggt gcggcgtcag cgacgtgttc gcctacccgg gcggcgcgtc catggagatc     300
caccaggcgc tgacgcgctc cccggtcatc accaaccacc tcttccgcca cgagcagggc     360
gaggcgttcg cggcgtccgg gtacgcgcgc gcgtccggcc gcgtcgggct ctgcgtcgcc     420
acctccggcc ccggggcaac caacctcgtg tccgcgctcg ccgacgcgct gctcgactcc     480
gtcccgatgg tcgccatcac gggccaggtc ccccgccgca tgatcggcac cgacgccttc     540
caggagacgc ccatagtcga ggtcacccgc tccatcacca agcacaatta ccttgtcctt     600
gatgtggagg acatcccccg cgtcatacag gaagccttct tcctcgcgtc ctcgggccgt     660
cctggcccgg tgctggtcga catccccaag gacatccagc agcagatggc tgtgccagtc     720
tgggacacct cgatgaatct accggggtac attgcacgcc tgcccaagcc acccgcgaca     780
gaattgcttg agcaggtctt gcgtctggtt ggcgagtcac ggcgcccgat tctctatgtc     840
ggtggtggct gctctgcatc tggtgatgaa ttgcgccggt tgttgagct gaccggcatc     900 ccagttacaa ccactctgat gggcctcggc aatttcccca gtgatgatcc gttgtccctg     960
cgcatgcttg gatgcatgg cacggtgtac gcaaattatg cggtggataa ggctgacctg    1020
ttgcttgcat ttggcgtgcg gtttgatgat cgtgtgacag ggaaaattga ggcttttgca    1080
agcagggcca agattgtgca cattgacatt gatccagcgg agattggaaa gaacaagcaa    1140
ccacatgtgt caatttgcgc agatgttaag cttgctttac agggcttgaa tgctctgcta    1200
gaccagagca caacaaagac aagttctgat tttagtgcat ggcacaatga gttggaccag    1260
cagaagaggg agtttcctct ggggtacaag acttttggtg aagagatccc accgcaatat    1320
gctattcagg tgctggatga gctgacgaaa gggaggcaa tcatcgctac tggtgttgga    1380
cagcaccaga tgtgggcggc acaatattac acctacaagc ggccacggca gtggctgtct    1440
tcggctggtc tgggcgcaat gggatttggg ctgcctgctg cagctggtgc ttctgtggct    1500
aacccaggtg tcacagttgt tgatattgat gggdatggta gcttcctcat gaacattcag    1560
gagttggcat tgatccgcat tgagaacctc ccggtgaagg tgatggtgtt gaacaaccaa    1620 catttggta tggttgtgca atgggaggat aggttttaca aggcaaatag gcgcataca     1680 tacttgggca acccagaatg tgagagcgag atatatccag attttgtgac tattgctaaa    1740
```

```
gggttcaata ttcctgcagt ccgtgtaaca aagaagagtg aagtccgtgc cgccatcaag    1800
aagatgctcg agaccccagg gccatacttg ttggatatca tcgtcccaca ccaggagcat    1860
gtgctgccta tgatcccaag tgggggcgca ttcaaggaca tgatcctgga tggtgatggc    1920
aggactatgt attaatctat aatctgtatg ttggcaaagc accagcccgg cctatgtttg    1980
acctga                                                               1986
```

```
<210> SEQ ID NO 15
<211> LENGTH: 360
<212> TYPE: PRT
<213> ORGANISM: Oryza sativa
<220> FEATURE:
<221> NAME/KEY: misc_feature
<223> OTHER INFORMATION: Partial AHAS sequence, line CMC31

<400> SEQUENCE: 15
```

```
Arg Arg Pro Ile Leu Tyr Val Gly Gly Gly Cys Ser Ala Ser Gly Asp
1               5                   10                  15

Glu Leu Arg Arg Phe Val Glu Leu Thr Gly Ile Pro Val Thr Thr Thr
            20                  25                  30

Leu Met Gly Leu Gly Asn Phe Pro Ser Asp Asp Pro Leu Ser Leu Arg
        35                  40                  45

Met Leu Gly Met His Gly Thr Val Tyr Ala Asn Tyr Ala Val Asp Lys
    50                  55                  60

Ala Asp Leu Leu Leu Ala Phe Gly Val Arg Phe Asp Asp Arg Val Thr
65                  70                  75                  80

Gly Lys Ile Glu Ala Phe Ala Ser Arg Ala Lys Ile Val His Ile Asp
                85                  90                  95

Ile Asp Pro Ala Glu Ile Gly Lys Asn Lys Gln Pro His Val Ser Ile
            100                 105                 110

Cys Ala Asp Val Lys Leu Ala Leu Gln Gly Leu Asn Ala Leu Leu Asp
        115                 120                 125

Gln Ser Thr Thr Lys Thr Ser Ser Asp Phe Ser Ala Trp His Asn Glu
    130                 135                 140

Leu Asp Gln Gln Lys Arg Glu Phe Pro Leu Gly Tyr Lys Thr Phe Gly
145                 150                 155                 160

Glu Glu Ile Pro Pro Gln Tyr Ala Ile Gln Val Leu Asp Glu Leu Thr
                165                 170                 175

Lys Gly Glu Ala Ile Ile Ala Thr Gly Val Gly Gln His Gln Met Trp
            180                 185                 190

Ala Ala Gln Tyr Tyr Thr Tyr Lys Arg Pro Arg Gln Trp Leu Ser Ser
        195                 200                 205

Ala Gly Leu Gly Ala Met Gly Phe Gly Leu Pro Ala Ala Gly Ala
    210                 215                 220

Ser Val Ala Asn Pro Gly Val Thr Val Asp Ile Asp Gly Asp Gly
225                 230                 235                 240

Ser Phe Leu Met Asn Ile Gln Glu Leu Ala Leu Ile Arg Ile Glu Asn
                245                 250                 255

Leu Pro Val Lys Val Met Val Leu Asn Asn Gln His Leu Gly Met Val
            260                 265                 270

Val Gln Trp Glu Asp Arg Phe Tyr Lys Ala Asn Arg Ala His Thr Tyr
        275                 280                 285

Leu Gly Asn Pro Glu Cys Glu Ser Glu Ile Tyr Pro Asp Phe Val Thr
    290                 295                 300

Ile Ala Lys Gly Phe Asn Ile Pro Ala Val Arg Val Thr Lys Lys Ser
```

```
                305                 310                 315                 320
        Glu Val Arg Ala Ala Ile Lys Lys Met Leu Glu Thr Pro Gly Pro Tyr
                        325                 330                 335

Leu Leu Asp Ile Ile Val Pro His Gln Glu His Val Leu Pro Met Ile
                        340                 345                 350

Pro Lys Gly Ala His Ser Arg Thr
                        355                 360

<210> SEQ ID NO 16
<211> LENGTH: 528
<212> TYPE: DNA
<213> ORGANISM: Oryza sativa
<220> FEATURE:
<221> NAME/KEY: misc_feature
<223> OTHER INFORMATION: Partial AHAS sequence, line CMC31

<400> SEQUENCE: 16
atgggatttg ggctgcctgc tgcagctggt gcttctgtgg ctaacccagg tgtcacagtt     60
gttgatattg atgggatgg tagcttcctc atgaacattc aggagttggc attgatccgc    120
attgagaacc tcccggtgaa ggtgatggtg ttgaacaacc aacatttggg tatggttgtg    180
caatgggagg ataggtttta caaggcaaat agggcgcata catacttggg caacccagaa    240
tgtgagagcg agatatatcc agattttgtg actattgcta aagggttcaa tattcctgca    300
gtccgtgtaa caaagaagag tgaagtccgt gccgccatca agaagatgct cgagacccca    360
gggccatact tgttggatat catcgtccca caccaggagc atgtgctgcc tatgatccca    420
aatgggggcg cattcaagga catgatcctg gatggtgatg caggactat gtattaatct    480 ataatctgta tgttggcaaa gcaccagccc ggcctatgtt tgacctga                 528

<210> SEQ ID NO 17
<211> LENGTH: 644
<212> TYPE: PRT
<213> ORGANISM: Oryza sativa
<220> FEATURE:
<221> NAME/KEY: misc_feature
<223> OTHER INFORMATION: Inferred complete AHAS sequence, wild type var.
      Cypress

<400> SEQUENCE: 17

Met Ala Thr Thr Ala Ala Ala Ala Ala Thr Leu Ser Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
                35                  40                  45

Pro Val Thr Pro Pro Ser Pro Ala Pro Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
                115                 120                 125

Ala Arg Ala Ser Gly Arg Val Gly Val Cys Val Ala Thr Ser Gly Pro
        130                 135                 140
```

-continued

```
Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
            165                 170                 175

Thr Asp Ala Phe Gln Glu Thr Pro Ile Val Glu Val Thr Arg Ser Ile
        180                 185                 190

Thr Lys His Asn Tyr Leu Val Leu Asp Val Glu Asp Ile Pro Arg Val
    195                 200                 205

Ile Gln Glu Ala Phe Phe Leu Ala Ser Ser Gly Arg Pro Gly Pro Val
210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
            245                 250                 255

Pro Pro Ala Thr Glu Leu Leu Glu Gln Val Leu Arg Leu Val Gly Glu
        260                 265                 270

Ser Arg Arg Pro Ile Leu Tyr Val Gly Gly Gly Cys Ser Ala Ser Gly
    275                 280                 285

Asp Glu Leu Arg Arg Phe Val Glu Leu Thr Gly Ile Pro Val Thr Thr
290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
            325                 330                 335

Lys Ala Asp Leu Leu Leu Ala Phe Gly Val Arg Phe Asp Asp Arg Val
        340                 345                 350

Thr Gly Lys Ile Glu Ala Phe Ala Ser Arg Ala Lys Ile Val His Ile
    355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
            405                 410                 415

Glu Leu Asp Gln Gln Lys Arg Glu Phe Pro Leu Gly Tyr Lys Thr Phe
        420                 425                 430

Gly Glu Glu Ile Pro Pro Gln Tyr Ala Ile Gln Val Leu Asp Glu Leu
    435                 440                 445

Thr Lys Gly Glu Ala Ile Ile Ala Thr Gly Val Gly Gln His Gln Met
450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
            485                 490                 495

Ala Ser Val Ala Asn Pro Gly Val Thr Val Val Asp Ile Asp Gly Asp
        500                 505                 510

Gly Ser Phe Leu Met Asn Ile Gln Glu Leu Ala Leu Ile Arg Ile Glu
    515                 520                 525

Asn Leu Pro Val Lys Val Met Val Leu Asn Asn Gln His Leu Gly Met
530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
```

```
                565                 570                 575
Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ser Gly Gly Ala Phe Lys Asp Met Ile Leu Asp Gly Asp Gly
625                 630                 635                 640

Arg Thr Met Tyr

<210> SEQ ID NO 18
<211> LENGTH: 1986
<212> TYPE: DNA
<213> ORGANISM: Oryza sativa
<220> FEATURE:
<221> NAME/KEY: misc_feature
<223> OTHER INFORMATION: Inferred complete AHAS sequence, lines PWC16,
      PWC23, CMC29, WDC33 and WDC38

<400> SEQUENCE: 18
atggctacga ccgccgcggc cgcggccgcc accttgtccg ccgccgcgac ggccaagacc      60
ggccgtaaga accaccagcg acaccacgtc cttcccgctc gaggccgggt gggggcggcg     120
gcggtcaggt gctcggcggt gtccccggtc accccgccgt ccccggcgcc gcggccacg     180 ccgctccggc cgtgggggcc ggccgagccc cgcaagggcg cggacatcct cgtggaggcg     240
ctggagcggt gcgcgtcag cgacgtgttc gcctacccgg gcgcgcgtc catgagatc      300 caccaggcgc tgacgcgctc cccggtcatc accaaccacc tcttccgcca cgagcagggc     360
gaggcgttcg cggcgtccgg gtacgcgcgc gtccggcc cgtcgggt ctgcgtcgcc      420 acctccggcc ccggggcaac caacctcgtg tccgcgctcg ccgacgcgct gctcgactcc     480
gtcccgatgg tcgccatcac gggccaggtc ccccgccgca tgatcggcac cgacgccttc     540
caggagacgc ccatagtcga ggtcacccgc tccatcacca gcacaatta ccttgtcctt     600 gatgtggagg acatccccg cgtcatacag gaagccttct tcctcgcgtc ctcgggccgt     660
cctggcccgg tgctggtcga catccccaag gacatccagc agcagatggc tgtgccagtc     720
tgggacacct cgatgaatct accggggtac attgcacgcc tgcccaagcc acccgcgaca     780
gaattgcttg agcaggtctt gcgtctggtt ggcgagtcac ggcgcccgat tctctatgtc     840
ggtggtggct gctctgcatc tggtgatgaa ttgcgccgt ttgttgagct gaccggcatc     900
ccagttacaa ccactctgat gggcctcggc aatttcccca gtgatgatcc gttgtccctg     960
cgcatgcttg gatgcatgg cacggtgtac gcaaattatg cggtggataa ggctgacctg    1020
ttgcttgcat ttggcgtgcg gtttgatgat cgtgtgacag ggaaaattga ggcttttgca    1080
agcagggcca agattgtgca cattgacatt gatccagcgg agattggaaa gaacaagcaa    1140
ccacatgtgt caatttgcgc agatgttaag cttgctttac agggcttgaa tgctctgcta    1200
gaccagagca acaaagac aagttctgat tttagtgcat ggcacaatga gttggaccag    1260
cagaagaggg agtttcctct ggggtacaag acttttggtg aagagatccc accgcaatat    1320
gctattcagg tgctggatga gctgacgaaa ggggaggcaa tcatcgctac tggtgttgga    1380
cagcaccaga tgtgggcggc acaatattac acctacaagc ggccacggca gtggctgtct    1440
tcggctggtc tgggcgcaat gggatttggg ctgcctgctg cagctggtgc ttctgtggct    1500
aacccaggtg tcacagttgt tgatattgat ggggatggta gcttcctcat gaacattcag    1560
```

-continued

```
gagttggcat tgatccgcat tgagaacctc ccggtgaagg tgatggtgtt gaacaaccaa    1620
catttgggta tggttgtgca atgggaggat aggttttaca aggcaaatag ggcgcataca    1680
tacttgggca acccagaatg tgagagcgag atatatccag attttgtgac tattgctaaa    1740
gggttcaata ttcctgcagt ccgtgtaaca aagaagagtg aagtccgtgc cgccatcaag    1800
aagatgctcg agaccccagg gccatacttg ttggatatca tcgtcccaca ccaggagcat    1860
gtgctgccta tgatcccaaa tggggggcgca ttcaaggaca tgatcctgga tggtgatggc    1920
aggactatgt attaatctat aatctgtatg ttggcaaagc accagcccgg cctatgtttg    1980
acctga                                                                1986
```

<210> SEQ ID NO 19
<211> LENGTH: 644
<212> TYPE: PRT
<213> ORGANISM: Oryza sativa
<220> FEATURE:
<221> NAME/KEY: misc_feature
<223> OTHER INFORMATION: Inferred complete AHAS sequence, lines PWC16,
      PWC23, CMC29, WDC33 & WDC38

<400> SEQUENCE: 19

```
Met Ala Thr Thr Ala Ala Ala Ala Ala Thr Leu Ser Ala Ala
1               5                   10                  15

Thr Ala Lys Thr Gly Arg Lys Asn His Gln Arg His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270
```

-continued

```
Ser Arg Arg Pro Ile Leu Tyr Val Gly Gly Cys Ser Ala Ser Gly
    275                 280                 285

Asp Glu Leu Arg Arg Phe Val Glu Leu Thr Gly Ile Pro Val Thr Thr
290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                    325                 330                 335

Lys Ala Asp Leu Leu Leu Ala Phe Gly Val Arg Phe Asp Asp Arg Val
                340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
                    405                 410                 415

Glu Leu Asp Gln Gln Lys Arg Glu Phe Pro Leu Gly Tyr Lys Thr Phe
                420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                    485                 490                 495

Ala Ser Val Ala Asn Pro Gly Val Thr Val Val Asp Ile Asp Gly Asp
                500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                    565                 570                 575

Thr Ile Ala Lys Gly Phe Asn Ile Pro Ala Val Arg Val Thr Lys Lys
                580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
610                 615                 620

Ile Pro Asn Gly Gly Ala Phe Lys Asp Met Ile Leu Asp Gly Asp Gly
625                 630                 635                 640

Arg Thr Met Tyr

<210> SEQ ID NO 20
<211> LENGTH: 1985
<212> TYPE: DNA
<213> ORGANISM: Oryza sativa
<220> FEATURE:
<221> NAME/KEY: misc_feature
```

<223> OTHER INFORMATION: Inferred complete AHAS sequence, line CMC31

<400> SEQUENCE: 20

```
atggctacga ccgccgcggc cgcggccgcc accttgtccg ccgccgcgac ggccaagacc      60
ggccgtaaga accaccagcg acaccacgtc cttcccgctc gaggccgggt ggggcggcg     120
gcggtcaggt gctcggcggt gtccccggtc accccgccgt ccccggcgcc gccggccacg     180
ccgctccggc cgtgggggcc ggccgagccc gcaagggcg cggacatcct cgtgaggcg      240
ctggagcggt gcggcgtcag cgacgtgttc gcctacccgg gcggcgcgtc catggagatc     300
caccaggcgc tgacgcgctc cccggtcatc accaaccacc tcttccgcca cgagcagggc     360
gaggcgttcg cggcgtccgg gtacgcgcgc gcgtccggcc gcgtcggggt ctgcgtcgcc     420
acctccggcc ccggggcaac caacctcgtg tccgcgctcg ccgacgcgct gctcgactcc     480
gtcccgatgg tcgccatcac gggccaggtc ccccgccgca tgatcggcac cgacgccttc     540
caggagacgc ccatagtcga ggtcaccgc tccatcacca agcacaatta ccttgtcctt     600
gatgtggagg acatccccg cgtcatacag gaagccttct tcctcgcgtc ctcgggccgt     660
cctggcccgg tgctggtcga catccccaag gacatccagc agcagatggc tgtgccagtc     720
tgggacacct cgatgaatct accggggtac attgcacgcc tgcccaagcc acccgcgaca     780
gaattgcttg agcaggtctt gcgtctggtt ggcgagtcac ggcgcccgat tctctatgtc     840
ggtggtggct gctctgcatc tggtgatgaa ttgcgccggt tgttgagct gaccggcatc     900
ccagttacaa ccactctgat gggcctcggc aatttcccca gtgatgatcc gttgtccctg     960
cgcatgcttg gatgcatgg cacggtgtac gcaaattatg cggtggataa ggctgacctg    1020
ttgcttgcat ttggcgtgcg gtttgatgat cgtgtgacag gaaaattga ggcttttgca    1080
agcagggcca agattgtgca cattgacatt gatccagcgg agattggaaa gaacaagcaa    1140
ccacatgtgt caatttgcgc agatgttaag cttgctttac agggcttgaa tgctctgcta    1200
gaccagagca acaaaagac aagttctgat tttagtgcat ggcacaatga gttggaccag    1260
cagaagaggg agtttcctct ggggtacaag acttttggtg aagagatccc accgcaatat    1320
gctattcagg tgctggatga gctgacgaaa ggggaggcaa tcatcgctac tggtgttgga    1380
cagcaccaga tgtgggcggc acaatattac acctacaagc ggccacggca gtggctgtct    1440
tcggctggtc tgggcgcaat gggatttggg ctgcctgctg cagctggtgc ttctgtggct    1500
aacccaggtg tcacagttgt tgatattgat ggggatggta gcttcctcat gaacattcag    1560
gagttggcat tgatccgcat tgagaacctc ccggtgaagg tgatggtgtt gaacaaccaa    1620
catttgggta tggttgtgca atgggaggat aggttttaca aggcaaatag gcgcatacaa    1680
tacttgggca acccagaatg tgagagcgag atatatccag attttgtgac tattgctaaa    1740
gggttcaata ttcctgcagt ccgtgtaaca aagaagagtg aagtccgtgc cgccatcaag    1800
aagatgctcg agaccccagg gccatacttg ttggatatca tcgtcccaca ccaggagcat    1860
gtgctgccta tgatcccaaa ggggggcgcat tcaaggacat gatcctggat ggtgatggca    1920
ggactatgta ttaatctata atctgtatgt tggcaaagca ccagcccggc ctatgtttga    1980
cctga                                                                 1985
```

<210> SEQ ID NO 21
<211> LENGTH: 633
<212> TYPE: PRT
<213> ORGANISM: Oryza sativa
<220> FEATURE:
<221> NAME/KEY: misc_feature
<223> OTHER INFORMATION: Inferred complete AHAS sequence, line CMC31

<400> SEQUENCE: 21

```
Met Ala Thr Thr Ala Ala Ala Ala Ala Thr Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
            35                  40                  45

Pro Val Thr Pro Pro Ser Pro Ala Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
            130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
            195                 200                 205

Ile Gln Glu Ala Phe Phe Leu Ala Ser Ser Gly Arg Pro Gly Pro Val
            210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
            275                 280                 285

Asp Glu Leu Arg Arg Phe Val Glu Leu Thr Gly Ile Pro Val Thr Thr
            290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
            370                 375                 380

Ile Cys Ala Asp Val Lys Leu Ala Leu Gln Gly Leu Asn Ala Leu Leu
385                 390                 395                 400
```

-continued

Asp Gln Ser Thr Thr Lys Thr Ser Ser Asp Phe Ser Ala Trp His Asn
            405                 410                 415

Glu Leu Asp Gln Gln Lys Arg Glu Phe Pro Leu Gly Tyr Lys Thr Phe
        420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
        450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
            485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
        530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
            565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
        610                 615                 620

Ile Pro Lys Gly Ala His Ser Arg Thr
625                 630

<210> SEQ ID NO 22
<211> LENGTH: 22
<212> TYPE: DNA
<213> ORGANISM: Artificial sequence
<220> FEATURE:
<221> NAME/KEY: misc_feature
<223> OTHER INFORMATION: RA 7 primer

<400> SEQUENCE: 22
agtggctgtc ttcggctggt ct                                          22

<210> SEQ ID NO 23
<211> LENGTH: 24
<212> TYPE: DNA
<213> ORGANISM: Artificial sequence
<220> FEATURE:
<221> NAME/KEY: misc_feature
<223> OTHER INFORMATION: RA 5 primer

<400> SEQUENCE: 23
cctaccacta ccgtcctgac acat                                        24

<210> SEQ ID NO 24
<211> LENGTH: 1986
<212> TYPE: DNA
<213> ORGANISM: Oryza sativa
<220> FEATURE:
<221> NAME/KEY: misc_feature
<223> OTHER INFORMATION: Complete AHAS sequence, line 93AS3510

<400> SEQUENCE: 24

```
atggctacga ccgccgcggc cgcggccgcc accttgtccg ccgccgcgac ggccaagacc    60
ggccgtaaga accaccagcg acaccacgtc cttcccgctc gaggccgggt ggggcggcg    120
gcggtcaggt gctcggcggt gtccccggtc accccgccgt ccccggcgcc gccggccacg    180
ccgctccggc cgtgggggcc ggccgagccc cgcaagggcg cggacatcct cgtggaggcg    240
ctggagcggt gcgcgtcag cgacgtgttc gcctacccgg cgcgcgtc catggagatc    300
caccaggcgc tgacgcgctc cccggtcatc accaaccacc tcttccgcca cgagcagggc    360
gaggcgttcg cggcgtccgg gtacgcgcgc cgtccggcc cgtcggggt ctgcgtcgcc    420
acctccggcc ccggggcaac caacctcgtg tccgcgctcg ccgacgcgct gctcgactcc    480
gtcccgatgg tcgccatcac gggccaggtc ccccgccgca tgatcggcac cgacgccttc    540
caggagacgc ccatagtcga ggtcacccgc tccatcacca agcacaatta ccttgtcctt    600
gatgtggagg acatccccg cgtcatacag gaagccttct tcctcgcgtc ctcgggccgt    660
cctggcccgg tgctggtcga catccccaag gacatccagc agcagatggc tgtgccagtc    720
tgggacacct cgatgaatct accggggtac attgcacgcc tgcccaagcc acccgcgaca    780
gaattgcttg agcaggtctt cgtctggtt ggcgagtcac ggcgcccgat tctctatgtc    840
ggtggtggct gctctgcatc tggtgatgaa ttgcgccggt ttgttgagct gaccggcatc    900
ccagttacaa ccactctgat gggcctcggc aatttcccca gtgatgatcc gttgtccctg    960
cgcatgcttg ggatgcatgg cacggtgtac gcaaattatg cggtggataa ggctgacctg   1020
ttgcttgcat ttggcgtgcg gtttgatgat cgtgtgacag gaaaattga ggcttttgca   1080
agcagggcca agattgtgca cattgacatt gatccagcgg agattggaaa gaacaagcaa   1140
ccacatgtgt caatttgcgc agatgttaag cttgctttac agggcttgaa tgctctgcta   1200
gaccagagca caacaaagac aagttctgat tttagtgcat ggcacaatga gttggaccag   1260
cagaagaggg agtttcctct ggggtacaag actttggtg aagagatccc accgcaatat   1320
gctattcagg tgctggatga gctgacgaaa gggaggcaa tcatcgctac tggtgttgga   1380
cagcaccaga tgtgggcggc acaatattac acctacaagc ggccacggca gtggctgtct   1440
tcggctggtc tgggcgcaat gggatttggg ctgcctgctg cagctggtgc ttctgtggct   1500
aacccaggtg tcacagttgt tgatattgat gggatggta gcttcctcat gaacattcag   1560
gagttggcat tgatccgcat tgagaacctc ccggtgaagg tgatggtgtt gaacaaccaa   1620
catttgggta tggttgtgca atgggaggat aggttttaca aggcaaatag ggcgcataca   1680
tacttgggca acccagaatg tgagagcgag atatatccag attttgtgac tattgctaaa   1740
gggttcaata ttcctgcagt ccgtgtaaca aagaagagtg aagtccgtgc cgccatcaag   1800
aagatgctcg agacccccagg gccatacttg ttggatatca tcgtcccaca ccaggagcat   1860
gtgctgccta tgatcccaag tgaggcgca ttcaaggaca tgatcctgga tggtgatggc   1920
aggactatgt attaatctat aatctgtatg ttggcaaagc accagcccgg cctatgtttg   1980
acctga                                                             1986
```

<210> SEQ ID NO 25
<211> LENGTH: 644
<212> TYPE: PRT
<213> ORGANISM: Oryza sativa
<220> FEATURE:
<221> NAME/KEY: misc_feature
<223> OTHER INFORMATION: Inferred complete AHAS sequence, line 93AS3510

<400> SEQUENCE: 25

```
Met Ala Thr Thr Ala Ala Ala Ala Ala Thr Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Ala Thr Pro Leu Arg Pro
50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
            245                 250                 255

Pro Pro Ala Thr Glu Leu Leu Glu Gln Val Leu Arg Leu Val Gly Glu
        260                 265                 270

Ser Arg Arg Pro Ile Leu Tyr Val Gly Gly Gly Cys Ser Ala Ser Gly
    275                 280                 285

Asp Glu Leu Arg Arg Phe Val Glu Leu Thr Gly Ile Pro Val Thr Thr
290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
```

-continued

```
                    405                 410                 415
Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
            485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
    530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
            565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
    610                 615                 620

Ile Pro Ser Glu Gly Ala Phe Lys Asp Met Ile Leu Asp Gly Asp Gly
625                 630                 635                 640

Arg Thr Met Tyr
```